(12) United States Patent
Edman et al.

(10) Patent No.: US 6,326,173 B1
(45) Date of Patent: Dec. 4, 2001

(54) ELECTRONICALLY MEDIATED NUCLEIC ACID AMPLIFICATION IN NASBA

(75) Inventors: Carl F. Edman, San Diego; Michael I. Nerenberg, La Jolla, both of CA (US)

(73) Assignee: Nanogen/Becton Dickinson Partnership, San Diego, CA (US)

( * ) Notice: Subject to any disclaimer, the term of this patent is extended or adjusted under 35 U.S.C. 154(b) by 0 days.

(21) Appl. No.: 09/290,338

(22) Filed: Apr. 12, 1999

(51) Int. Cl.[7] .............................. C12P 19/34; C12Q 1/68; C12M 1/00; C12M 1/34; C07H 21/04

(52) U.S. Cl. .......................... 435/91.1; 436/6; 436/91.2; 436/283.1; 436/285.2; 436/285.1; 436/287.2; 530/22.1; 530/23.1; 530/25.32; 530/24.3; 530/24.31; 530/24.32

(58) Field of Search .................. 435/6, 91.1, 91.2, 435/283.1, 285.1, 285.2; 536/287.2, 22.1, 23.1, 25.32, 24.3, 24.31, 24.32, 24.33

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 4,800,159 | 1/1989 | Mullis et al. | 435/172.3 |
| 4,988,617 | 1/1991 | Landegren et al. | 435/6 |
| 5,130,238 | 7/1992 | Malek et al. | 435/91 |
| 5,202,231 | 4/1993 | Drmanac et al. | 435/6 |
| 5,270,184 * | 12/1993 | Walker et al. | 435/91.2 |
| 5,380,489 | 1/1995 | Sutton et al. | 422/68.1 |
| 5,422,252 | 6/1995 | Walker et al. | 435/91.2 |
| 5,455,166 | 10/1995 | Walker | 435/91.2 |
| 5,470,723 | 11/1995 | Walker et al. | 435/91.2 |
| 5,474,895 | 12/1995 | Ishii et al. | 435/6 |
| 5,516,663 | 5/1996 | Backman et al. | 435/91.2 |
| 5,545,531 | 8/1996 | Rava et al. | 435/6 |
| 5,573,907 | 11/1996 | Carrino et al. | 435/6 |
| 5,594,111 | 1/1997 | Stolowitz | 530/391.1 |
| 5,594,151 | 1/1997 | Stolowitz | 548/542 |
| 5,605,662 | 2/1997 | Heller et al. | 422/68.1 |
| 5,623,055 | 4/1997 | Stolowitz | 530/391.1 |
| 5,624,825 | 4/1997 | Walker et al. | 435/91.2 |
| 5,641,658 | 6/1997 | Adams et al. | 435/91.2 |
| 5,648,211 | 7/1997 | Fraiser et al. | 435/6 |
| 5,648,470 | 7/1997 | Stolowitz | 530/391.1 |
| 5,668,257 | 9/1997 | Stolowitz | 530/391.1 |
| 5,668,258 | 9/1997 | Stolowitz | 530/391.1 |
| 5,677,431 | 10/1997 | Stolowitz | 530/391.1 |
| 6,017,696 * | 1/2000 | Heller et al. | 435/6 |
| 6,066,461 | 5/2000 | McMillan et al. | |

FOREIGN PATENT DOCUMENTS

| | | |
|---|---|---|
| 0 320 308A2 | 6/1989 | (EP) . |
| 95/35390 | 12/1995 | (WO) . |
| 96/01836 | 1/1996 | (WO) . |
| 96/15271 | 5/1996 | (WO) . |
| 96/30546 | 10/1996 | (WO) . |

OTHER PUBLICATIONS

Guo et al NAR vol. 22 No. 24 pp. 5456–5464 1994.*
Bertina et al., "Mutation in blood coagulation factor V associated with resistance to activated protein C,"*Nature* 369:64–67 (1994).
Chee et al., "Accessing Genetic Information with HighDensity DNA Arrays," *Science* 274:610–614 (1996).
DeRisi et al., "Exploring the Metabolic and Genetic Control of Gene Expression on a Genomic Scale," *Science* 278:680–686 (1997).
DeRisi et al., "Use of a cDNA microarray to analyse gene expression patterns in human cancer," *Nature genetics* 14(4):457–460 (1996).
Edman et al., "Electric field directed nucleic acid hybridization on microchips," *Nucleic Acids Research* 25(24):4907–4914 (1997).
Guo et al., "Enhanced discrimination of single nucleotide polymorphisms by artificial mismatch hybridization," *Nature Biotechnology* 15(4):331–335 (1997).
Heller et al., Discovery and analysis of inflammatory disease–related genes using cDNA microarrays, *Proc. Natl. Acad. Sci. USA* 94:2150–2155 (1997).
Hughes et al., "Determination of the Etiology of presumptive Feline Leprosy by 16S rRNA Gene Analysis," *Journal of Clinical Microbiology* 35(10):2464–2471 (1997).
Linton et al., "PCR Detection, Identification to Species level, and Fingerprinting of *Campylobacter jejuni* and *Campylobacter coli* Direct from Diarrheic Samples," *Journal of Clinical Microbiology* 35(10):2568–2572 (1997).
Liu et al., "Molecular Detection of a Common Mutation in Coagulation Factor V Causing Thrombosis via Hereditary Resistance to Activated Protein C," *Diagnostic Molecular Pathology* 4(3):191–197 (1995).
Lockhart et al., "Expression monitoring by hybridization to high–density oligonucleotide arrays," *Nature Biotechnology* 14(13):1675–1680 (1996).
Malek et al., "Nucleic Acid Sequence–Based Amplification (NASBA™)", Protocols for Nucleic Acid Analysis By Nonradioactive Probes, *Methods in Molecular Biology* 28:253–260 (1994).
Milla et al., Use of the Restriction Enzyme AvaI and Exo—Bst Polymerase in Strand Displacement Amplification, *Bio Techniques* 24(3):392–395 (1998).
Robinson et al., "Molecular Recognition Mediated by Bound Water; A Mechanism for Star Activity of the Restriction Endonuclease EcoRI," *J. Mol. Biol.* 234:302–306 (1993).

(List continued on next page.)

*Primary Examiner*—Kenneth R. Horlick
*Assistant Examiner*—Jeffrey Siew
(74) *Attorney, Agent, or Firm*—Lyon & Lyon LLP

(57) ABSTRACT

A method of improving amplification of nucleic acids using a nucleic acid sequence-based amplification ("NASBA") method is provided wherein target nucleic acids and NASBA primers are electronically addressed to electronically addressable capture sites of a microchip. This improvement uses electronically induced hybridization of the target nucleic acids to the primers. The primers may be solution-based or immobilized on the capture sites of the microchip.

64 Claims, 34 Drawing Sheets

OTHER PUBLICATIONS

Robinson et al., "Hydrostatic Pressure Reverses Osmotic Pressure Effects on the Specificity of EcoRI–DNA interactions," *Biochemistry* 33(13):3787–3793 (1994).

Robinson et al., "Heterogeneity in molecular recognition by restriction endonucleases: Osmotic and hydrostatic pressure effects on BamHI, Pvu II, and EcoRV specificity," *Proc. Natl. Acad. Sci. USA* 92:3444–3448 (1995).

Schena et al., "Quantitative Monitoring of Gene Expression Patterns with a Complementary DNA Microarray," *Science* 270:467–470 (1995).

Schena et al., "Parallel human genome analysis: Microarray–based expression monitoring of 1000 genes," *Proc. Natl. Acad. Sci USA* 93:10614–10619 (1996).

Sosnowski et al., "Rapid determination of single base mismatch mutations in DNA hybrids by direct electric field control," *Proc. Nat. Acad. Sci. USA* 94:1119–1123 (1997).

Southern et al., "Analyzing and Comparing Nucleic Acid Sequences by Hybridization to Arrays of Oligonucleotides: Evaluation Using Expreimental Models," *Genomics* 13:1008–1017 (1992).

Southern et al., "Detection of Specific Sequences Among Dna Fragments Separated by Gel Electrophroesis," *J. Mol. Biol.* 98:503–517 (1975).

Southern et al., "DNA chips: analysing sequence by hybridization to oligonucleotides on a large scale," *TIG* 12(3):110–115 (1996).

Spargo et al., "Detection of *M. tuberculosis* DNA using Thermophilic Strand Displacement Amplification," *Molecular and Cellular Probes* 10:247–256 (1996).

Walker, "Empirical Aspects of Strand Displacement Amplification," *PCR Methods and Applications* 3(1):1–6 (1993).

Woese, "Bacterial Evolution," *Microbiological Reviews* 51(2):221–271 (1987).

* cited by examiner

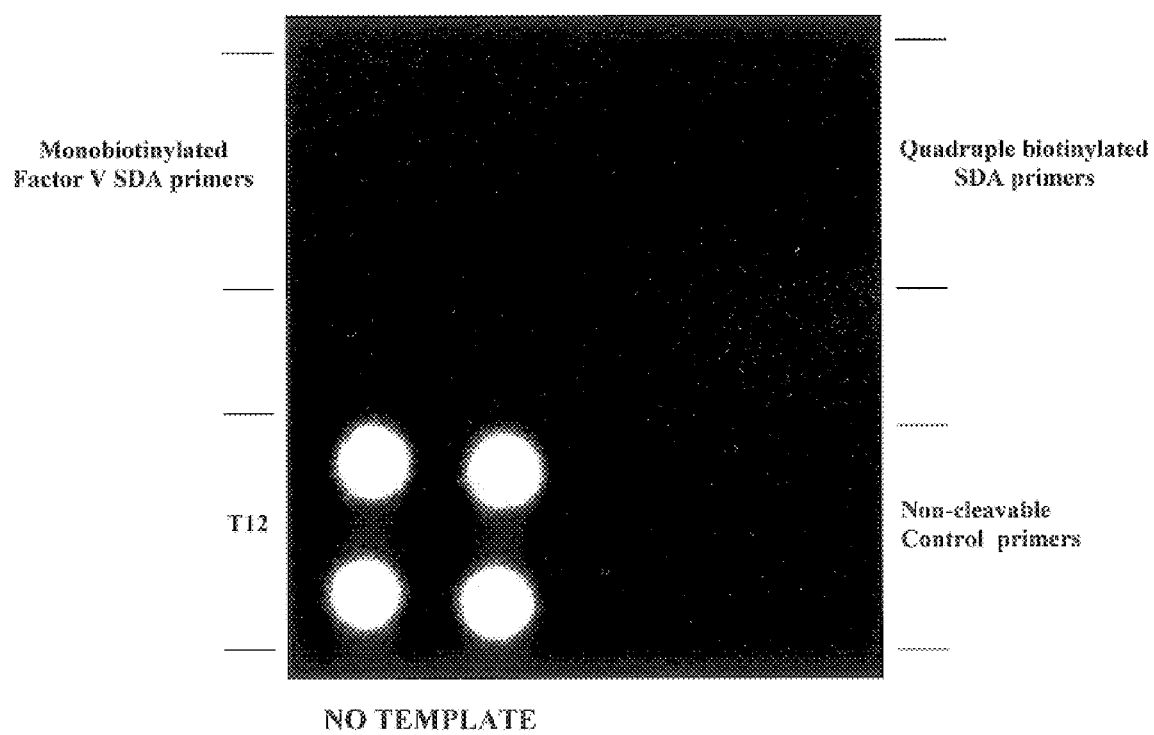

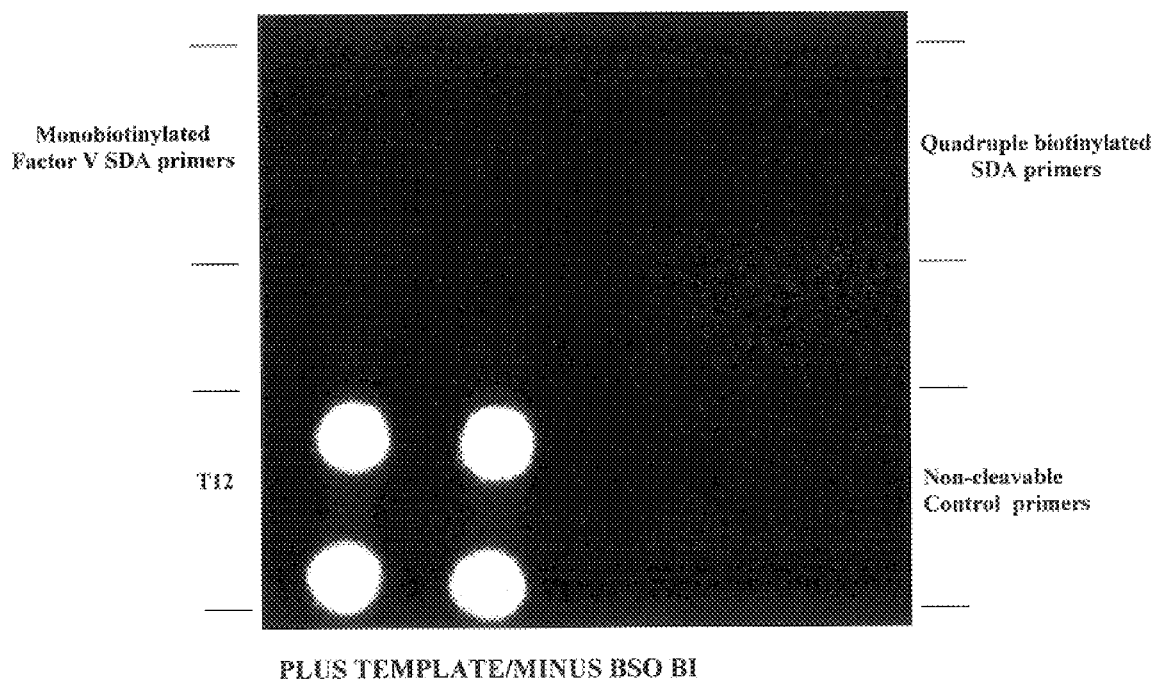

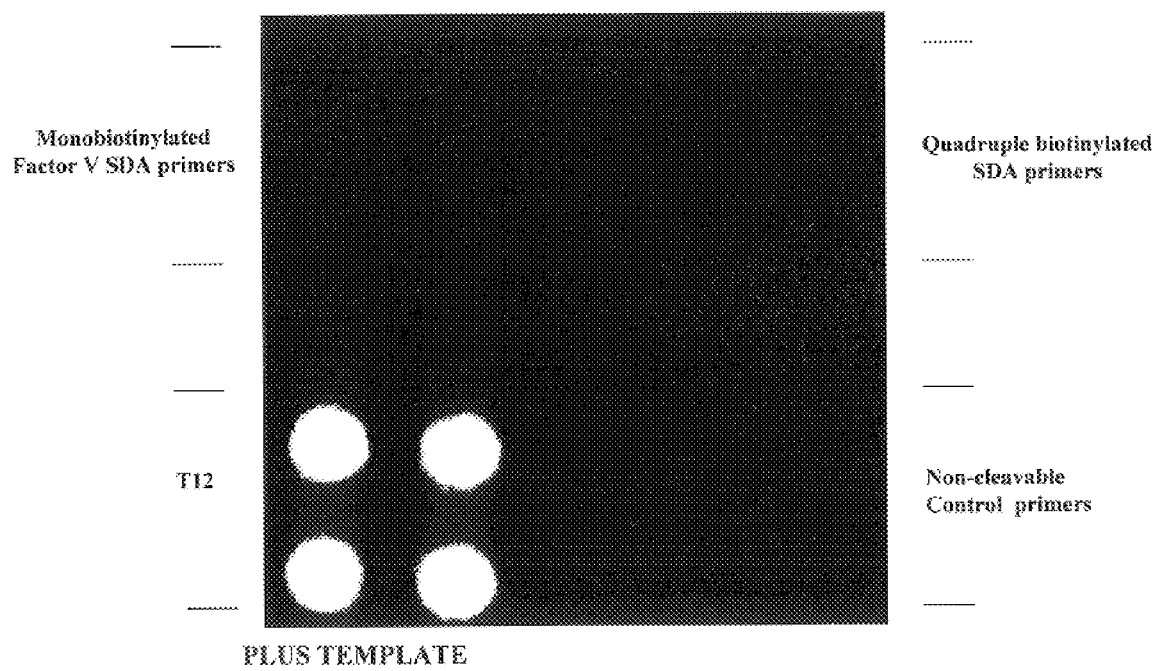

Lane
1. mol wt markers
2. PCR amplification
3. NASBA 1X template
4. NASBA 1,000X diluted template
5. NASBA 1,000,000X diluted template
6. NASBA - no template Experimental Layout Control - No template + all reporter oligos All templates + Factor V Reporter oligo All templates + Factor V, Chlamydia Reporter Oligos All templates + Factor V, Chlamydia and Hemachromatosis reporter oligos Control Solution SDA reactions

LIGATION-DEPENDENT DETECTION OF THE SALMONELLA spaQ GENE

LIGATION PROBES LP1 AND LP2:

```
spaQ¹    TEMPLATE       5-nnnnncaacatgacatcattacgagacgggatagtaaatgatgattagtgnnnnn-3'
                                    |||||||||||||||||||||||||||||||||||
LP1²                 3-*aattcccgcatgagctgggtaatgttgtactgtagtaatgctctgc*-5'

3'-cctatcaattacctactaaatcacgattatccctagagtcatgtgggctc    LP2³
                                                              |||||||||||||||||||||||||||||||||||||||||||||||||||
                                                                                                                 ttcagacctcgccttagc-5'
```

AMPLIFICATION PRIMER SEQUENCES S1 AND S2:

```
                   LP1       3-*aattcccgcatgagctgggtaatgttgtactgtagtaatgctctgc*-5'
                                 ||||||||||||
S1⁴      5'-accgcatcgaatgcatgtctcgggtaaggcgtactcgacc LP2       3'-cctatcaattacctactaaatcacgattatccctagagtcatgtgggctcttcagacctcgccttagc-5'
                                                                                                    |——————————————————|
                                                                                                            S2⁵
```

FIG. 23D

SEQUENCE LISTING

<160> NUMBER OF SEQ ID NOS: 62

<210> SEQ ID NO 1
<211> LENGTH: 20
<212> TYPE: DNA
<213> ORGANISM: conserved 16S bacterial sequence

<400> SEQUENCE: 1
caaatgaatt gacgggggcc                                           20

<210> SEQ ID NO 2
<211> LENGTH: 15
<212> TYPE: DNA
<213> ORGANISM: conserved 16S bacterial sequence

<400> SEQUENCE: 2
aagggttgcg ctcgt                                                15

<210> SEQ ID NO 3
<211> LENGTH: 40
<212> TYPE: DNA
<213> ORGANISM: conserved 16S bacterial sequence

<400> SEQUENCE: 3
accgcatcga atgcatgtcc tcgggtgcat gtggtttaat                     40

<210> SEQ ID NO 4
<211> LENGTH: 41
<212> TYPE: DNA
<213> ORGANISM: conserved 16S bacterial sequence

<400> SEQUENCE: 4
acgattcagc tccagacttc tcgggtaaca tttcacaaca c         41

<210> SEQ ID NO 5
<211> LENGTH: 20
<212> TYPE: DNA
<213> ORGANISM: human

<400> SEQUENCE: 5
actacagtga cgtggacatc                                 20

<210> SEQ ID NO 6
<211> LENGTH: 20
<212> TYPE: DNA
<213> ORGANISM: human

<400> SEQUENCE: 6
tgttatcaca ctggtgctaa                                 20

<210> SEQ ID NO 7
<211> LENGTH: 42
<212> TYPE: DNA
<213> ORGANISM: human

<400> SEQUENCE: 7
accgcatcga atgcatgtcc tcgggtctct gggctaatag ga        42

<210> SEQ ID NO 8
<211> LENGTH: 42
<212> TYPE: DNA
<213> ORGANISM: human

<400> SEQUENCE: 8
acgattcagc tccagacttc tcgggtaata cctgtattcc tc        42

<210> SEQ ID NO 9
<211> LENGTH: 42
<212> TYPE: DNA
<213> ORGANISM: human

<400> SEQUENCE: 9
acgattcagc tccagacttc tcgggtaata cctgtattcc tt        42

<210> SEQ ID NO 10
<211> LENGTH: 18
<212> TYPE: DNA
<213> ORGANISM: human

<400> SEQUENCE: 10
ctgtattcct cgcctgtc                                   18

<210> SEQ ID NO 11
<211> LENGTH: 18
<212> TYPE: DNA
<213> ORGANISM: E. coli

<400> SEQUENCE: 11

```
ctcatctctg aaaacttc                                                    18
```

<210> SEQ ID NO 12
<211> LENGTH: 18
<212> TYPE: DNA
<213> ORGANISM: Shigella dysenteriae

<400> SEQUENCE: 12

```
cgtatctcta caaggttc                                                    18
```

<210> SEQ ID NO 13
<211> LENGTH: 18
<212> TYPE: DNA
<213> ORGANISM: Salmonella typhimurium

<400> SEQUENCE: 13

```
tccatctctg gattcttc                                                    18
```

<210> SEQ ID NO 14
<211> LENGTH: 18
<212> TYPE: DNA
<213> ORGANISM: Camphylobacter Jejuni

<400> SEQUENCE: 14

```
catatctcta taaggttc                                                    18
```

<210> SEQ ID NO 15
<211> LENGTH: 27
<212> TYPE: DNA
<213> ORGANISM: conserved 16S bacterial sequence

<400> SEQUENCE: 15

```
ggatgtcaag accaggtaag gttcttc                                          27
```

<210> SEQ ID NO 16
<211> LENGTH: 50
<212> TYPE: DNA
<213> ORGANISM: human T-cell leukemia virus-1

<400> SEQUENCE: 16

```
aattctaata cgactcacta tagggagagg tgatctgatg tctggacagg                 50
```

<210> SEQ ID NO 17
<211> LENGTH: 23
<212> TYPE: DNA
<213> ORGANISM: human T-cell leukemia virus-1

<400> SEQUENCE: 17

```
acttcccagg gtttggacag agt                                              23
```

<210> SEQ ID NO 18
<211> LENGTH: 30
<212> TYPE: DNA
<213> ORGANISM: human T-cell leukemia virus-1

<400> SEQUENCE: 18

```
ttcttttcgg atacccagtc tacgtgtttg                                       30
```

<210> SEQ ID NO 19
<211> LENGTH: 23
<212> TYPE: DNA
<213> ORGANISM: human T-cell leukemia virus-1

<400> SEQUENCE: 19

```
acttcccagg gtttggacag agt                                          23

<210> SEQ ID NO 20
<211> LENGTH: 42
<212> TYPE: DNA
<213> ORGANISM: human

<400> SEQUENCE: 20
accgcatcga atgcatgtcc tcgggtctct gggctaatag ga                     42

<210> SEQ ID NO 21
<211> LENGTH: 42
<212> TYPE: DNA
<213> ORGANISM: human

<400> SEQUENCE: 21
acgattcagc tccagacttc tcgggtcaga atttctgaaa gg                     42

<210> SEQ ID NO 22
<211> LENGTH: 20
<212> TYPE: DNA
<213> ORGANISM: human

<400> SEQUENCE: 22
actacagtga cgtggacatc                                              20

<210> SEQ ID NO 23
<211> LENGTH: 20
<212> TYPE: DNA
<213> ORGANISM: human

<400> SEQUENCE: 23
tgttatcaca ctggtgctaa                                              20

<210> SEQ ID NO 24
<211> LENGTH: 18
<212> TYPE: DNA
<213> ORGANISM: human

<400> SEQUENCE: 24
ctgtattcct cgcctgtc                                                18

<210> SEQ ID NO 25
<211> LENGTH: 42
<212> TYPE: DNA
<213> ORGANISM: Chlamydia trachomatis

<400> SEQUENCE: 25
cacgtagtca atgcatgtcc tcgggtacaa catcaacacc tg                     42

<210> SEQ ID NO 26
<211> LENGTH: 42
<212> TYPE: DNA
<213> ORGANISM: Chlamydia trachomatis

<400> SEQUENCE: 26
acgattcagc tccagacttc tcgggtgaga ctgttaaaga ta                     42

<210> SEQ ID NO 27
<211> LENGTH: 17
<212> TYPE: DNA
<213> ORGANISM: Chlamydia trachomatis
```

-continued

```
<400> SEQUENCE: 27
cagcaaataa tccttgg                                                    17

<210> SEQ ID NO 28
<211> LENGTH: 19
<212> TYPE: DNA
<213> ORGANISM: Chlamydia trachomatis

<400> SEQUENCE: 28
cattggttga tggattatt                                                  19

<210> SEQ ID NO 29
<211> LENGTH: 15
<212> TYPE: DNA
<213> ORGANISM: Chlamydia trachomatis

<400> SEQUENCE: 29
gtcgcagcca aaatg                                                      15

<210> SEQ ID NO 30
<211> LENGTH: 16
<212> TYPE: DNA
<213> ORGANISM: Chlamydia trachomatis

<400> SEQUENCE: 30
ttccatcaga agctgt                                                     16

<210> SEQ ID NO 31
<211> LENGTH: 42
<212> TYPE: DNA
<213> ORGANISM: human

<400> SEQUENCE: 31
cacgtagtca atgcatgtcc tcgggtataa ccttggctgt ac                        42

<210> SEQ ID NO 32
<211> LENGTH: 42
<212> TYPE: DNA
<213> ORGANISM: human

<400> SEQUENCE: 32
acgattcagc tccagacttc tcgggtgctc tcatcagtca ca                        42

<210> SEQ ID NO 33
<211> LENGTH: 19
<212> TYPE: DNA
<213> ORGANISM: human

<400> SEQUENCE: 33
tgaaggataa gcagccaat                                                  19

<210> SEQ ID NO 34
<211> LENGTH: 19
<212> TYPE: DNA
<213> ORGANISM: human

<400> SEQUENCE: 34
ctcctctcaa cccccaata                                                  19

<210> SEQ ID NO 35
<211> LENGTH: 18
<212> TYPE: DNA
<213> ORGANISM: human
```

```
<400> SEQUENCE: 35
agatatacgt gccaggtg                                                18

<210> SEQ ID NO 36
<211> LENGTH: 18
<212> TYPE: DNA
<213> ORGANISM: human

<400> SEQUENCE: 36
ctgatccagg cctgggtg                                                18

<210> SEQ ID NO 37
<211> LENGTH: 45
<212> TYPE: DNA
<213> ORGANISM: Salmonella

<400> SEQUENCE: 37
aattccgcat gagctgggta atgttgtact gtagtaatgc tctgc                  45

<210> SEQ ID NO 38
<211> LENGTH: 70
<212> TYPE: DNA
<213> ORGANISM: Salmonella

<400> SEQUENCE: 38
cctatcaatt tacctactaa atcacgatta tccccctagag tcatgtgggc tcttcagacc 60
tcgccttagc                                                         70

<210> SEQ ID NO 39
<211> LENGTH: 40
<212> TYPE: DNA
<213> ORGANISM: synthetic

<400> SEQUENCE: 39
accgcatcga atgcatgtct cgggtaaggc gtactcgacc                        40

<210> SEQ ID NO 40
<211> LENGTH: 40
<212> TYPE: DNA
<213> ORGANISM: synthetic

<400> SEQUENCE: 40
cgattccgct ccagacttct cgggtgtact gagatcccct                        40

<210> SEQ ID NO 41
<211> LENGTH: 48
<212> TYPE: DNA
<213> ORGANISM: synthetic

<400> SEQUENCE: 41
caacatgaca tcattacgag acgggatagt taaatggatg atttagtg               48

<210> SEQ ID NO 42
<211> LENGTH: 42
<212> TYPE: DNA
<213> ORGANISM: human

<400> SEQUENCE: 42
accgcatcga atgcatgtcc tccggtctct gggctaatag ga                     42

<210> SEQ ID NO 43
```

```
<211> LENGTH: 42
<212> TYPE: DNA
<213> ORGANISM: human

<400> SEQUENCE: 43
acgattcagc tccagacttc tccggtcaga atttctgaaa gg              42

<210> SEQ ID NO 44
<211> LENGTH: 21
<212> TYPE: DNA
<213> ORGANISM: human

<400> SEQUENCE: 44
acttctaatc tgtaagagca g                                     21

<210> SEQ ID NO 45
<211> LENGTH: 41
<212> TYPE: DNA
<213> ORGANISM: synthetic

<400> SEQUENCE: 45
gagggcggtt taataatcta cggtggtcga gtacgcctta a               41

<210> SEQ ID NO 46
<211> LENGTH: 63
<212> TYPE: DNA
<213> ORGANISM: synthetic

<400> SEQUENCE: 46
cgattccgct ccagacttct cgggtgtact gagatcccct tgtcagaggg atagatccag    60
agg                                                                  63

<210> SEQ ID NO 47
<211> LENGTH: 43
<212> TYPE: DNA
<213> ORGANISM: synthetic

<400> SEQUENCE: 47
gatggagttc agtggtaata caatgtggtc gagtacgcct taa             43

<210> SEQ ID NO 48
<211> LENGTH: 61
<212> TYPE: DNA
<213> ORGANISM: synthetic

<400> SEQUENCE: 48
cgattccgct ccagacttct cgggtgtact gagatccccc ggtttcatca tatctggcgt    60
t                                                                    61

<210> SEQ ID NO 49
<211> LENGTH: 39
<212> TYPE: DNA
<213> ORGANISM: synthetic

<400> SEQUENCE: 49
gacgctgctc actagatgtc taggtcgagt acgccttaa                  39

<210> SEQ ID NO 50
<211> LENGTH: 64
<212> TYPE: DNA
<213> ORGANISM: synthetic

<400> SEQUENCE: 50
```

```
cgattccgct ccagacttct cgggtgtact gagatcccct ggttataagt gcttgatact    60
ccag                                                                 64
```

<210> SEQ ID NO 51
<211> LENGTH: 41
<212> TYPE: DNA
<213> ORGANISM: synthetic

<400> SEQUENCE: 51

```
gatgatgtca tgttgcaatg tcctggtcga gtacgcctta a                        41
```

<210> SEQ ID NO 52
<211> LENGTH: 61
<212> TYPE: DNA
<213> ORGANISM: synthetic

<400> SEQUENCE: 52

```
cgattccgct ccagacttct cgggtgtact gagatcccct catttaacta tcccgtctcg    60
t                                                                    61
```

<210> SEQ ID NO 53
<211> LENGTH: 44
<212> TYPE: DNA
<213> ORGANISM: synthetic

<400> SEQUENCE: 53

```
gagtaattac cgtcttcatc tttttttggt cgagtacgcc ttaa                     44
```

<210> SEQ ID NO 54
<211> LENGTH: 65
<212> TYPE: DNA
<213> ORGANISM: synthetic

<400> SEQUENCE: 54

```
cgattccgct ccagacttct cgggtgtact gagatcccct ggcttcatca agaataacat    60
ctatc                                                                65
```

<210> SEQ ID NO 55
<211> LENGTH: 40
<212> TYPE: DNA
<213> ORGANISM: synthetic

<400> SEQUENCE: 55

```
gatttacgga ctggttctcc cttggtcgag tacgccttaa                          40
```

<210> SEQ ID NO 56
<211> LENGTH: 61
<212> TYPE: DNA
<213> ORGANISM: synthetic

<400> SEQUENCE: 56

```
cgattccgct ccagacttct cgggtgtact gagatcccct tcagaagccg tgaagagaat    60
g                                                                    61
```

<210> SEQ ID NO 57
<211> LENGTH: 39
<212> TYPE: DNA
<213> ORGANISM: synthetic

<400> SEQUENCE: 57

-continued

```
gaccaaaacc atcctgaacc atggtcgagt acgccttaa                        39

<210> SEQ ID NO 58
<211> LENGTH: 67
<212> TYPE: DNA
<213> ORGANISM: synthetic

<400> SEQUENCE: 58
cgattccgct ccagacttct cgggtgtact gagatcccct ttctagtttt tgatttttag  60
tattata                                                           67

<210> SEQ ID NO 59
<211> LENGTH: 42
<212> TYPE: DNA
<213> ORGANISM: synthetic

<400> SEQUENCE: 59
gagtagaggt atgtgatgag ccaatggtcg agtacgcctt aa                    42

<210> SEQ ID NO 60
<211> LENGTH: 61
<212> TYPE: DNA
<213> ORGANISM: synthetic

<400> SEQUENCE: 60
cgattccgct ccagacttct cgggtgtact gagatcccct ctttggctaa actcggtttt  60
c                                                                 61

<210> SEQ ID NO 61
<211> LENGTH: 39
<212> TYPE: DNA
<213> ORGANISM: synthetic

<400> SEQUENCE: 61
gattagctga gcttaccgcc gtggtcgagt acgccttaa                        39

<210> SEQ ID NO 62
<211> LENGTH: 60
<212> TYPE: DNA
<213> ORGANISM: synthetic

<400> SEQUENCE: 62
cgattccgct ccagacttct cgggtgtact gagatcccct ccgtagcaag ttgcgtgaag  60
```

ELECTRONICALLY MEDIATED NUCLEIC ACID AMPLIFICATION IN NASBA

FIELD OF THE INVENTION

This invention relates to devices, methods, and compositions of matter for performing active, multi-step, and multiplex nucleic acid sequence separation, amplification and diagnostic analyses. Generally, it relates to devices, methods, and compositions of matter for amplification and analysis of nucleic acid sequences in a sample. More specifically, the invention relates to methods, devices, and compositions of matter for amplifying and analyzing nucleic acids using novel strand displacement amplification technologies in combination with bioelectronic microchip technology. The devices and methods of the invention are useful in a variety of applications, including, for example, disease diagnostics (infectious and otherwise), genetic analyses, agricultural and environmental applications, drug discovery, pharmacogenomics, and food and/or water monitoring and analysis.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to that invention.

Definitions

The following descriptions of the inventions contained herein use numerous technical terms specific to the field of the invention. Generally, the meaning of these terms are known to those having skill in the art and are further described as follows:

As used herein, "sample" refers to a substance that is being assayed for the presence of one or more nucleic acids of interest. The nucleic acid or nucleic acids of interest may be present in a mixture of other nucleic acids. A sample, containing the nucleic acids of interest, may be obtained in numerous ways. It is envisioned that the following could represent samples: cell lysates, purified genomic DNA, body fluids such as from a human or animal, clinical samples, food samples, etc.

As used herein, the phrases "target nucleic acid" and "target sequence" are used interchangeably. Both phrases refer to a nucleic acid sequence, the presence or absence of which is desired to be detected. Target nucleic acid can be single-stranded or double-stranded and, if it is double-stranded, it may be denatured to single-stranded form prior to its detection using methods, as described herein, or other well known methods. Additionally, the target nucleic acid may be nucleic acid in any form most notably DNA or RNA.

As used herein, "amplification" refers to the increase in the number of copies of a particular nucleic acid target of interest wherein said copies are also called "amplicons" or "amplification products".

As used herein, "amplification components" refers to the reaction materials such as enzymes, buffers, and nucleic acids necessary to perform an amplification reaction to form amplicons or amplification products of a target nucleic acid of interest.

As used herein, the phrase "multiplex amplification" refers to the amplification of more than one nucleic acid of interest. For example, it can refer to the amplification of multiple sequences from the same sample or the amplification of one of several sequences in a sample, as described in U.S. Pat. Nos. 5,422,252 and 5,470,723 which are incorporated herein by reference. The phrase also refers to the amplification of one or more sequences present in multiple samples either simultaneously or in step-wise fashion.

As used herein, "oligonucleotide" refers to a molecule comprising two or more deoxyribonucleotides or ribonucleotides, preferably more than three. The length of an oligonucleotide will depend on how it is to be used. The oligonucleotide may be derived synthetically or by cloning. Oligonucleotides may also comprise protein nucleic acids (PNAs).

As used herein, "probe" refers to a known sequence of a nucleic acid that is capable of selectively binding to a target nucleic acid. More specifically, "probe" refers to an oligonucleotide designed to be sufficiently complementary to a sequence of one strand of a nucleic acid that is to be probed such that the probe and nucleic acid strand will hybridize under selected stringency conditions. Specific types of oligonucleotide probes are used in various embodiments of the invention. For example, a "ligation probe" describes one type of probe designed to bind to both a target nucleic acid of interest and to an amplification probe. Additionally, a "ligated probe" or a "ligated probe template" refers to the end product of a ligation reaction between a pair of ligation probes.

As used herein, the terms "primer molecule" and "primer" are used interchangeably. A primer is a nucleic acid molecule with a 3' terminus that is either "blocked" and cannot be covalently linked to additional nucleic acids or that is not blocked and possesses a chemical group at the 3' terminus that will allow extension of the nucleic acid chain such as catalyzed by a DNA polymerase or reverse transcriptase.

As used herein, the phrase "amplification primer" refers to an oligonucleotide primer used for amplification of a target nucleic acid sequence.

The phrase "primer extension," as used herein refers to the DNA polymerase induced extension of a nucleic acid chain from a free three-prime (3') hydroxy group thereby creating a strand of nucleic acid complementary to an opposing strand.

As used herein, the term "amplicon" refers to the product of an amplification reaction. An amplicon may contain amplified nucleic acids if both primers utilized hybridize to a target sequence. An amplicon may not contain amplified nucleic acids if one of the primers used does not hybridize to a target sequence. Thus, this term is used generically herin and does not imply the presence of amplified nucleic acids.

As used herein, "electronically addressable" refers to a capacity of a microchip to direct materials such as nucleic acids and enzymes and other amplification components from one position to another on the microchip by electronic biasing of the capture sites of the chip. "Electronic biasing" is intended to mean that the electronic charge at a capture site or another position on the microchip may be manipulated between a net positive and a net minus charge so that charged molecules in solution and in contact with the microchip may be directed toward or away from one position on the microchip or from one position to another position.

As used herein, the phrase "capture site" refers to a specific position on an electronically addressable microchip wherein electronic biasing is initiated and where molecules seen as nucleic acid probes and target molecules are attracted or addressed by such biasing.

As used herein, the term "anchored" refers to the immobilization by binding of a molecule to a specified location on a microchip, such as a primer nucleic acid used in an SDA reaction, or a nucleic acid probe used to capture a target nucleic acid.

As used herein, the term "branched primer pair" refers to a pair of oligonucleotides that may be used as primers in an amplification reaction and which are connected together through a chemical moiety such that the oligonucleotides are susceptible to hybridization and use as amplification primers.

As used herein, the term "primer capture probes" refers to oligonucleotides that are used to hybridize to selected target nucleic acids and provide anchoring support for such nucleic acids to a capture site. Moreover, such oligonucleotides may function as amplification primers for amplifying said target nucleic acids.

As used herein, "hybridization" and "binding" are used interchangeably and refer to the non-covalent binding or "base pairing" of complementary nucleic acid sequences to one another. Whether or not a particular probe remains base paired with a polynucleotide sequence depends on the degree of complementarity, the length of the probe, and the stringency of the binding conditions. The higher the stringency, the higher must be the degree of complementarity, and/or the longer the probe for binding or base pairing to remain stable.

As used herein, "stringency" refers to the combination of conditions to which nucleic acids are subjected that cause double stranded nucleic acid to dissociate into component single strands such as pH extremes, high temperature, and salt concentration. The phrase "high stringency" refers to hybridization conditions that are sufficiently stringent or restrictive such that only specific base pairing will occur. The specificity should be sufficient to allow for the detection of unique sequences using an oligonucleotide probe or closely related sequence under standard Southern hybridization protocols (as described in J. Mol. Biol. 98:503 (1975)).

As used herein, "endonuclease" refers to enzymes (e.g., restriction endonucleases, etc.) that cut DNA at sites within the DNA molecule.

As used herein, a "restriction endonuclease recognition site" refers to a specific sequence of nucleotides in a double stranded DNA that is recognized and acted upon enzymatically by a DNA restriction endonuclease.

As used herein, the term "nicking" refers to the cutting of a single strand of a double stranded nucleic acid by breaking the bond between two nucleotides such that the 5' nucleotide has a free 3' hydroxyl group and the 3' nucleotide has a 5' phosphate group. It is preferred that the nicking be accomplished with a restriction endonuclease and that this restriction endonuclease catalyze the nicking of double stranded nucleic acid at the proper location within the restriction endonuclease recognition site.

As used herein, the phrase "modified nucleotide" refers to nucleotides or nucleotide triphosphates that differ in composition and/or structure from natural nucleotide and nucleotide triphosphates. It is preferred that the modified nucleotide or nucleotide triphosphates used herein are modified in such a way that, when the modifications are present on one strand of a double stranded nucleic acid where there is a restriction endonuclease recognition site, the modified nucleotide or nucleotide triphosphates protect the modified strand against cleavage by restriction enzymes. Thus, the presence of the modified nucleotides or nucleotide triphosphates encourages the nicking rather than the cleavage of the double stranded nucleic acid.

As used herein, the phrase "DNA polymerase" refers to enzymes that are capable of incorporating nucleotides onto the 3' hydroxyl terminus of a nucleic acid in a 5' to 3' direction thereby synthesizing a nucleic acid sequence.

Examples of DNA polymerases that can be used in accordance with the methods described herein include, E. coli DNA polymerase I, the large proteolytic fragment of E. coli DNA polymerase I, commonly known as "Klenow" polymerase, "Taq" polymerase, T7 polymerase, Bst DNA polymerase, T4 polymerase, T5 polymerase, reverse transcriptase, exo-BCA polymerase, etc.

As used herein, the term "displaced," refers to the removing of one molecule from close proximity with another molecule. In connection with double stranded oligonucleotides and/or nucleic acids, the term refers to the rendering of the double stranded nucleic acid molecule single stranded, i.e., one strand is displaced from the other strand. Displacement of one strand of a double-stranded nucleic acid can occur when a restriction endonuclease nicks the double stranded nucleic acid creating a free 3' hydroxy which is used by DNA polymerase to catalyze the synthesis of a new strand of nucleic acid. Alternatively, one nucleic acid may be displaced from another nucleic acid by the action of electronic biasing of an electrically addressable microchip.

As used herein, "ligase" refers to an enzyme that is capable of covalently linking the 3' hydroxyl group of a nucleotide to the 5' phosphate group of a second nucleotide. Examples of ligases include E. coli DNA ligase, T4 DNA ligase, etc. As used herein, "ligating" refers to covalently attaching two nucleic acid molecules to form a single nucleic acid molecule. This is typically performed by treatment with a ligase, which catalyzes the formation of a phosphodiester bond between the 5' end of one sequence and the 3' end of the other. However, in the context of the invention, the term "ligating" is also intended to encompass other methods of connecting such sequences, e.g., by chemical means.

The term "attaching" as used herein generally refers to connecting one entity to another. For example, oligomers and primers may be attached to the surface of a capture site. With respect to attaching mechanisms, methods contemplated include such attachment means as ligating, non-covalent bonding, binding of biotin moieties such as biotinylated primers, amplicons, and probes to strepavidin, etc.

As used herein, the term "adjacent" is used in reference to nucleic acid molecules that are in close proximity to one another. The term also refers to a sufficient proximity between two nucleic acid molecules to allow the 5' end of one nucleic acid that is brought into juxtaposition with the 3' end of a second nucleic acid so that they may be ligated by a ligase enzyme.

The term "allele specific" as used herein refers to detection, amplification or oligonucleotide hybridization of one allele of a gene without substantial detection, amplification or oligonucleotide hybridization of other alleles of the same gene.

As used herein, the term "three-prime" or "3'" refers to a specific orientation as related to a nucleic acid. Nucleic acids have a distinct chemical orientation such that their two ends are distinguished as either five-prime (5') or three-prime (3'). The 3' end of a nucleic acid contains a free hydroxyl group attached to the 3' carbon of the terminal pentose sugar. The 3' end of a nucleic acid contains a free hydroxyl or phosphate group attached to the 5' carbon of the terminal pentose sugar.

As used herein, the phrase "free three-prime (3') hydroxyl group," refers to the presence of a hydroxyl group located at the 3' terminus of a strand of nucleic acid. The phrase also refers to the fact that the free hydroxyl is functional such that it is able to support new nucleic acid synthesis.

As used herein, the phrase "five-prime overhang" refers to a double-stranded nucleic acid molecule, which does not have blunt ends, such that the ends of the two strands are not coextensive, and such that the 5' end of one strand extends beyond the 3' end of the opposing complementary strand. It is possible for a linear nucleic acid molecule to have zero, one, or two, 5' overhangs. The significance of a 5' overhang is that it provides a region where a 3' hydroxyl group is present on one strand and a sequence of single stranded nucleic acid is present on the opposite strand. A DNA polymerase can synthesize a nucleic acid strand complementary to the single stranded portion of the nucleic acid beginning from the free 3' hydroxyl of the recessed strand.

As used herein, the term "bumper primer" refers to a primer used to displace primer extension products in SDA reaction. The bumper primer anneals to a target sequence upstream of the amplification primer such that extension of the bumper primer displaces the downstream amplification primer and its extension product.

As used herein, the terms "detected" and "detection" are used interchangeably and refer to the discernment of the presence or absence of a target nucleic acid or amplified nucleic acid products thereof.

As used herein, "label" refers to a chemical moiety that provides the ability to detect an amplification product. For example, a label on a nucleic acid may comprise a radioactive isotope such as $^{32}P$ or non-radioactive molecule such as covalently or noncovalently attached chromophores, fluorescent moieties, enzymes, antigens, groups with specific reactivity, chemiluminescent moieties, and electrochemically detectable moieties.

The above definitions should not be understood to limit the scope of the invention. Rather, they should be used to interpret the language of the description and, where appropriate, the language of the claims. These terms may also be understood more fully in the context of the description of the invention. If a term is included in the description or the claims that is not defined above, or that cannot be interpreted based on its context, then it should be construed to have the same meaning as it is understood by those of skill in the art.

BACKGROUND ART

Determining the nucleic acid sequence of genes is important in many situations. For example, numerous diseases are caused by or associated with a mutation in a gene sequence relative to the normal gene. Such mutation may involve the substitution of only one base for another, called a "point mutation." In some instances, point mutations can cause severe clinical manifestations of disease by encoding a change in the amino acid sequence of the protein for which the gene codes. For example, sickle cell anemia results from such a point mutation.

Other diseases are associated with increases or decreases in copy numbers of genes. Thus, determining not only the presence or absence of changes in a sequence is important but also the quantity of such sequences in a sample can be used in the diagnosis of disease or the determination of the risk of developing disease. Moreover, variations in gene sequences of both prokaryotic and eukaryotic organisms has proven invaluable to identifying sources of genetic material (e.g., identifying one human from another or the source of DNA by restriction fragment length polymorphism (RFLP)).

Certain infections caused by microorganisms or viruses may also be diagnosed by the detection of nucleic acid sequences peculiar to the infectious organism. Detection of nucleic acid sequences derived from viruses, parasites, and other microorganisms is also important where the safety of various products is of concern, e.g., in the medical field where donated blood, blood products, and organs, as well as the safety of food and water supplies are important to public health.

Thus, identification of specific nucleic acid sequences by the isolation of nucleic acids from a sample and detection of the sought for sequences, provides a mechanism whereby one can determine the presence of a disease, organism or individual. Generally, such detection is accomplished by using a synthesized nucleic acid "probe sequence that is complementary in part the target nucleic acid sequence of interest.

Although it is desirable to detect the presence of nucleic acids as described above, it is often the case that the sought for nucleic acid sequences are present in sample sources in extremely small numbers (e.g., less than $10^7$). The condition of small target molecule numbers causes a requirement that laboratory techniques be performed in order to amplify the numbers of the target sequences in order that they may be detected. There are many well known methods of amplifying targeted sequences, such as the polymerase chain reaction (PCR), the ligase chain reaction (LCR), the strand displacement amplification (SDA), and the nucleic acid sequence-based amplification (NASBA), to name a few. These methods are described generally in the following references: (PCR) U.S. Pat. Nos. 4,683,195, 4,683,202, and 4,800,159; (LCR) EP Application No., 320,308 published Jun. 14, 1989; (SDA) U.S. Pat. Nos. 5,270,184, and 5,455,166 and "Empirical Aspects of Strand Displacement Amplification" by G. T. Walker in *PCR Methods and Applications*, 3(1):1–6 (1993), Cold Spring Harbor Laboratory Press; and (NASBA) "Nucleic Acid Sequence-Based Amplification (NASBA™)" by L. Malek et al., Ch. 36 in *Methods in Molecular Biology*, Vol. 28: Protocols for Nucleic Acid Analysis by Nonradioactive Probes, 1994 Ed. P. G. Isaac, Humana Press, Inc., Totowa, N.J. (Each of the above references are hereby incorporated by reference.)

With respect to analyzing and/or identifying target nucleic acid amplified products, i.e., "amplicons", other well known techniques have been typically used including comparative size, relative migration analyses (e.g., Southern blot analysis) and hybridization analysis. However, comparative size or relative migration analyses are not optimal because they are undesirably slow and inaccurate. Additionally, while hybridization analysis offers many advantages over these methods, hybridization analysis is neither rapid nor sensitive as compared to the teachings of the present invention.

With respect to PCR technology, since thermal cycling is required, PCR is not optimal for use in a microelectronic environment because the heat fluctuations caused by the thermal cycling are detrimental to the capture sites located on the surface of a microchip. Thermal cycling gives rise to other problems as well including the requirement for complex instrumentation (e.g., to ensure uniform heating, etc.), and, unacceptable time spans for completion of analysis (since each step must occur sequentially).

In contrast to PCR, the SDA technique is useful with microelectronic environments because it overcomes some of the above-described undesirable characteristics of PCR, e.g., it is an isothermal method and the amplification process is asynchronous, and, therefore, more rapid. Although the use of SDA has advantages over PCR, SDA schemes as currently practiced typically include the use of solution-based amplification protocols (e.g., disclosed in the above mentioned U.S. Pat. No. 5,455,166). Recent modifications of the SDA technique have advanced the technique to minimizing the number of individually designed primers for amplification as described in U.S. Pat. No. 5,624,825. However, such advances do not benefit from enhancements realized in the current invention of electronically controlled hybridization.

Other amplification procedures include the use of probes that are bound to a solid support. However, such procedures have not provided a discernable advance in the art compared to the "anchored" SDA presented herein and performed in conjunction with an electronically addressable microchip. For example, U.S. Pat. No. 5,380,489 discloses a method for nucleic acid amplification and detection of target nucleic acids wherein an adhesive element is used to affix capture probes so that target molecules may be more easily captured and detected. This method does not address the issue of simultaneous amplification, capture, and detection as does the current invention. In another example, U.S. Pat. No. 5,474,895 discloses detection of nucleic acids using a polystyrene support-based sandwich assay. Again, such a method merely involves passive hybridization followed by subsequent detection following secondary passive hybridization of a probe.

Microchip arrays have also been used in association with nucleic acid amplification and detection. For example, miniaturized devices have been successfully developed for expression monitoring. See, e.g., M. Schena, et al., 270 Science 467–470 (1995), M. Schena, et al., 93 Proc. Natl. Acad. Sci. USA 10614–619 (1996), J. DeRisi, et al., 14 Nat. Genet. 457–60 (1996), R. A. Heller, et al., 94 Proc. Natl. Acad. Sci. USA 2150–55 (1997), and J. DeRisi, et al., 278 Science 680–86 (1997). Miniaturized devices have also been successfully developed for analysis of single nucleotide polymorphisms (SNPs) within an amplicon. See, e.g., Z. Guo, et al., 15 Nat. Biotechnol. 331–35 (1997), and E. Southern, 12 Trends Genet. 110–15 (1996). (Each of the above publications are hereby incorporated by reference). These devices offer the potential for combining the specificity of hybridization with the speed and sensitivity of microchip technology. However, none have successfully provided a suitable miniaturized device for the present purposes.

For example, although micro-devices have been used to analyze multiple amplicons simultaneously (i.e., multiplex analysis), such multiplex analysis has been possible only if hybridization conditions are compatible for each amplicon being tested. This detriment may be partially compensated for by careful capture probe design, by the use of very long captures (e.g. cDNA for expression monitoring) (see, e.g., R. A. Heller, et al., (1997) supra, and M. Schena, et al., (1995) supra), or by extensive redundancy and overlap of shorter capture oligonucleotide sequences. However, taken together, these considerations have imposed limitations on the use of most microchip devices. Moreover, high levels of redundancy such as that used with short oligonucleotide capture sequences results in the requirement for large arrays and complex informatics programs to interpret data obtained, and still certain sequence-specific regions may remain difficult to analyze. Alternatively, the use of long capture oligonucleotides permits use of uniformly elevated hybridization temperatures. However, the use of long capture probes and elevated hybridization temperatures (e.g., in the range of 45 to 75° C.) largely precludes single base pair mismatch analysis of highly related sequences.

Yet another disadvantage has become apparent with conventional microchips (e.g., those disclosed in U.S. Pat. Nos. 5,202,231 and 5,545,531, as well as in E. Southern et al., Genomics 13, 1008–1017 (1992); M. Schena et al., Science 279, 467–470 (1995); M. Chee et al., Science 274, 610–614 (1996); and D. J. Lockhart et al., Nature Biotechnology 14, 1675–1680 (1996) (all of which are herein incorporated by reference)), in that they depend upon passive hybridization and solution based amplification prior to the capture of amplified products on the microchips.

Further, many of these devices are unable to analyze and/or detect the amplification of target molecules from multiple samples simultaneously. In macroscopic devices, this latter problem is conventionally handled by "dot blot" formats in which individual samples occupy unique geometric positions with minimal contamination between samples. In contrast, for most microchips, the problem of detection and analysis usually requires expensive and complex nucleic acid deposition technology similar to dot blot macroscopic deposition but on a microscopic scale.

In another recent disclosure, (PCT WO96/01836), electronic microchips have been used in connection with PCR type amplification of nucleic acids. However, an amplification system requiring the simultaneous use of amplification enzymes and restriction enzymes for increasing the quantity of target amplicons at a specific capture site was not contemplated nor possible in that system. Rather, restriction digestion of captured nucleic acid species was considered in connection with the removal of double stranded nucleic acid species from capture sites following PCR type amplification procedures with detection of target species occurring subsequent to enzymatic cleavage. Moreover, that system provided anchored amplification primers complementary to only one strand of a target nucleic acid that were functional in a PCR reaction.

Like other microchip based amplification and detection platforms, the invention conceptualized in the PCT WO 96/01836 publication is substantially limited as compared to the SDA on electronically addressable microchips disclosed herein because the PCR type amplification of target species as taught in that publication required repeated disruption of double stranded species as well as functionality of solution based reverse primers. Such a situation results in the reduction of efficient amplification due to primer-primer interactions while use of restriction enzymes is inhibited due to fluctuations in reaction buffer conditions.

Finally, other aspects of amplification and detection of nucleic acids have been problematic and/or not optimal. One such problem has been the loss of specificity in the restriction endonuclease cleavage of nucleic acids by restriction enzymes. For example, it is known that some restriction endonucleases lose specificity for their DNA recognition sequence with increased osmotic pressure or reduced water activity. C. R. Robinson et al. J Mol. Biol. 234: 302–306 (1993). With reduced water activity, the restriction endonucleases will cleave DNA at recognition sites that differ by one base pair from the normal recognition site. The restriction sites that are off by one base pair are called "star" sites and the endonucleases recognition and cleavage of these star sites is called "star activity."

Robinson et al. found that bound water participates in sequence specificity of EcoRI DNA cleavage (Biochemistry 33(13):3787–3793(1994)), and further found that increasing hydrostatic pressure by conducting the reactions at elevated pressure from 0 to 100 atm. inhibited and ultimately eliminated star activity induced by osmotic pressure for EcoRI, PvuII, and BamHI, but not for EcoRV. (Proc. Natl. Acad. Sci. USA 92:3444–3448 (1995)). One recurrent problem with SDA that relies on restriction endonucleases is the frequency with which non-target sequences are amplified in a primer-independent manner due to star activity. Thus, there is a need to reduce or eliminate star activity in SDA reactions. In one embodiment of the current invention, we provide for the elimination of such star activity in SDA reactions by application of a high pressure SDA method.

In addition to advancing SDA technology by eliminating star activity, we also provide for various other advancements in the detection of nucleic acids using SDA in combination with a bioelectronic microchip. For example, amplification and separation of nucleic acid sequences may be carried out using ligation-dependent SDA. In contrast to ligation-dependent amplification procedures known in the art that require the amplified products to be separated from the starting material by a capture step, or that require that free ligation probe be separated from bound probe prior to ligation, the current invention eliminates the need to make separate isolation steps. Further, the current invention improves upon the SDA amplification process by eliminating the need for bumper primers as they have been used in the art. For example, typical ligation-dependent amplification procedures include capture steps by labeling one of the primers used during amplification. Separation may occur prior to ligation to prevent template independent ligation of the primers or separation may occur following ligation to isolate target DNA amplicons from the non-labeled/amplified DNA. Target DNA amplicons containing this label are separated from the non-labelled/amplified DNA. This separation requires an extra step following amplification. This extra manipulation of the sample increases the complexity of the procedure and thereby renders it less useful as a simple alternative to other current DNA amplification methods such as PCR. This extra manipulation of sample also hinders automation of the amplification procedure. In one embodiment of the current invention a ligation-dependent SDA method is provided that eliminates such extra steps facilitating automation of amplification and detection of target nucleic acids.

In other embodiments, we have provided additional advancements in nucleic acid amplification and detection technology using SDA and electronically addressable microchips which advancements collectively show that a need remains for devices, methods, and compositions of matter for efficiently and optimally amplifying, detecting and analyzing target nucleic acid sequences of interest.

SUMMARY OF THE INVENTION

This invention relates broadly to devices, methods, and compositions of matter for the multiplex amplification, detection and analysis of nucleic acid sequences wherein the amplification, detection and analysis is optimally accomplished using SDA in combination with bioelectronic microchip technology. The invention provides various efficient and optimal methods of amplifying target nucleic acids of interest as well as methods for analyzing resultant amplicons. In addition, the invention enables the amplification and analysis (either sequentially or simultaneously) of multiple samples containing target nucleic acids on a single open bioelectronic microchip.

In one aspect of this invention, the microchip device is an electronically controlled microelectrode array. See, PCT application WO96/01836, the disclosure of which is hereby incorporated by reference. In contrast to the passive hybridization environment of most other microchip devices, the electronic microchip devices (or active microarray devices) of the present invention offer the ability to actively transport or electronically address nucleic acids to discrete locations on the surface of the microelectrode array, and to bind the addressed nucleic acid at those locations to either the surface of the microchip at specified locations designated "capture sites" or to nucleic acids previously bound at those sites. See, R. Sosnowski, et al., 94 Proc. Natl. Acad. Sci. USA 119–123 (1997), and C. Edman, et al., 25 Nucleic Acids Res. 4907–14 (1997). The use of these active microarrays circumvent many of the limitations encountered by passive microdevices.

The active microchip arrays of the present invention overcome the size dependency of capture oligonucleotides and the complexity requirements of passive microdevices. Also, the microchip arrays of the present invention allow multiple independent sample analyses upon the same open microarray surface by selectively and independently targeting different samples containing nucleic acids of interest to various microelectrode locations. In other words, they allow parallel multiple sample processing on an open array. As mentioned above, traditional nucleic acid detection methodologies are restricted by the frequently long amplification and hybridization times required to achieve resolvable signals. An additional limitation to such methodologies is the inability to carry out multiplex hybridization events upon their analytical surfaces, thereby restricting information obtainable in any one assay. Both of these limitations are overcome in the present invention by use of active microelectronic arrays capable of selectively targeting and concentrating DNA to specific sites on the array. A further strength of these devices is the power to perform electronic hybridization and denaturation to discriminate single base polymorphisms. Thus, these active microelectrode arrays demonstrate the flexibility to handle a wide variety of tasks upon a common platform, beyond those seen with other microdevices.

The present invention preferably uses an amplification method different from traditional PCR. Specifically, the present invention uses strand displacement amplification (SDA). SDA is an amplification methodology that has sufficient sensitivity and robustness to rapidly (e.g., in about 15–45 minutes) and exponentially amplify a small number of target molecules over a complex background. See, e.g., C. Spargo, et al., 10 Molecular and Cellular Probes 247–56 (1996). In contrast to PCR, SDA is an isothermal technique that requires simpler thermal control and associated instrumentation. SDA is more compatible with a unified amplification-hybridization-detection system (i.e. a system wherein all steps are unified in one place, e.g., on a microarray chip) for rapid analyses of nucleic acids. This is primarily due to the fact that SDA does not require conditions (e.g. thermal cycling) which could be detrimental to the microarray of an electronically addressable microchip.

The efficiency of amplification reactions in passive hybridization wherein probes designed to capture target and amplicon nucleic acid molecules are anchored to the surface of the microarray is limited during the initial phases of amplification due to the low frequency of hybridization of target nucleic acid species to the appropriate primers located on the tethering surface. Typically, this process requires hours, even in reduced volumes of solution. However, the efficiency of this process is dramatically increased by electronically concentrating, (i.e. addressing), the nucleic acid to the vicinity of "anchored" primers, thereby increasing the frequency of encounter between the solution phase target nucleic acid and the anchored primers. Whereas prior concepts used PCR in connection with only one of the two amplification primers necessary for PCR amplification anchored to a specific site on the microarray, the current invention contemplates that both amplification primers necessary for SDA are anchored to a specific capture site on the microarray. Thus, in one embodiment of the invention, electronically concentrating and hybridizing the target nucleic acid to the surface of a microchip (i.e., capture sites) prior to the introduction of amplification reaction buffers, enzymes, nucleotides, etc., benefits greatly "anchored" amplification reactions, such as "anchored SDA", as described below. The rapid concentration and subsequent specific hybridization of template nucleic acid molecules to their complementary anchored amplification primers permits the surface of the array to be washed, removing unwanted and possibly interfering non-target nucleic acid from the reaction environment.

Employing electronic addressing of target nucleic acids to specific locations on the microarray has at least three other advantages over prior passive hybridization technologies. First, the overall time and efficiency of the amplification process is dramatically improved since a major rate-limiting step (that of the time required for the template to find the anchored primers) is removed from the overall reaction rate. Also, the use of electronic addressing acts to electronically concentrate target nucleic acids such that hybridization of the target species to the anchored amplification probes increases the number of target molecules at the selected site as compared to the number of target molecules that would be found at any particular site on a non-electronic, passive hybridization microarray for an equivalent time period. The result is that the absolute numbers of starting molecules for the amplification process is dramatically increased resulting in improvement in both the overall yield of amplification products and the sensitivity to lower starting template numbers.

The second advantage is that discrete target nucleic acids can be applied to specific locations upon the array surface thereby allowing multiple, different nucleic acid samples to be simultaneously amplified on one array. Alternatively, a nucleic acid sample can be targeted to several different locations, each containing specific sets of amplification primers so that multiple different amplification reactions can be simultaneously carried out from a single sample. As noted above, the ability to remove unnecessary and unhybridized DNA from the reaction mixture significantly aids this process.

A third advantage to this approach is that following an amplification reaction, the amplicons which have been addressed and bound to a specific site on the array are then available in a site-specific fashion for subsequent analyses, such as by (1) the introduction of fluorescently labeled nucleotides or (2) the hybridization of oligonucleotides at the end of the reaction by denaturation of the amplified material followed by hybridization with an appropriate reporter oligonucleotide having specificity for the tethered amplicon.

As is described herein, the ability of electronic targeting used in connection with the combination of an electronically addressable microchip and SDA to overcome the above-described limitations of prior methods is demonstrated in two examples of amplicon analysis. First, as described in more detail below, use of a common highly conserved locus (e.g., 16S rRNA) which is shared by numerous species of bacteria may be applied to multiple comparative analyses of individual samples to identify different bacteria types. Second, also described in more detail below, the electronic microarray of the present invention is used to simultaneously analyze multiple individual patient samples for the presence of the human Factor V Leiden (R506Q) gene mutation. The human Factor V Leiden (R506Q) gene indicates a predisposition to activated protein C resistance and venous thrombosis. This example shows successful parallel sample analyses from multiple patients. The test material used in this multiple patient sample analysis provides another aspect of the present invention, namely, an allele-specific amplification method using SDA, also described in more detail below.

Other aspects of the present invention are directed to various new amplification methods. Such novel SDA methods of the present invention are useful for providing amplicons for various analyses. For example, some of the SDA methods described herein are useful to optimize amplification conditions for conducting amplification on an electronically addressable microchip array. Other SDA methods are useful to provide amplicons particularly suited for use on an electronically addressable microchip array. Still other SDA methods are useful to optimize analysis conditions for an analysis conducted on an electronically addressable microchip array.

One embodiment of a SDA method of the present invention, more specifically, comprises an allele-specific SDA method. The method preferably selectively amplifies only those strands that include a specific allele. The method preferably uses amplifying primers designed so their 3' terminus complements the nucleotide sequence of the desired allele. The primer may also preferably include a biotin moiety on its 5' end to provide a facile mechanism for capturing the amplicon and/or target nucleic acid onto a capture site either prior to amplification or after amplification following electronic targeting. Additionally, in another allele-specific embodiment, a method is provided for analyzing multiple samples containing nucleic acids for the presence of alleles of a given gene, which comprises amplifying the nucleic acids in each sample by "two-strand" SDA to produce amplicons, wherein the first amplification uses primers specific for a first allele and the second amplification uses primers specific for a second allele, electronically addressing the amplicons on a microarray, hybridizing one or more reporter probes to the bound amplicons, and detecting the presence and location of the reporter probes on the microarray.

In another embodiment of the current invention, a unique combination of SDA and simultaneous detection of amplification products on an electronically addressable microchip is provided. In a preferred embodiment, SDA is carried out at the surface of a designated position on an electronic microchip wherein both upstream and downstream primers necessary for amplification are anchored to the same discrete capture site on a microarray. In one such embodiment, the primers are paired using a unique branched moiety that is "anchored" to the surface of the microchip. This branched primer pair design provides closely spaced primers having a defined distance and location from one another. Thus arrangement further provides a means by which the rate of SDA can be controlled. Moreover, combined with other elements of the invention, single stranded amplification products being created at the location of the primer pair may be easily and quickly addressed and captured by unused branched primer pairs onto the same or adjacent designated capture sites on the electronic microchip for further SDA.

In a preferred embodiment, each primer of the above mentioned primer pair further includes nucleic acid sequence encoding one strand of an endonuclease restriction site positioned 5' to a nucleic acid sequence having nucleic acid sequence complementary with a target molecule. In a further preferred embodiment, the sequence of the restriction sites in the primers are unmodified in that the nucleic acid backbone comprises a natural phosphate backbone that is cleavable by action of the restriction enzyme. Additionally, the restriction sites useful in SDA may be any restriction site typically used in SDA procedures as disclosed in the references incorporated herein such as HincII, HindII, Bso BI, AvaI, Fnu4HI, Tth111I, and NciI. Other endonucleases can also be used in this method including BstXI, BsmI, BsrI, BsaI, NlaV, NspI, PflMI, HphI, AlwI, FokI, AccI, TthIIII, Mra I, Mwo I, Bsr BI, Bst NI, Bst OI, and Bsm AI. Additionally, the enzyme need not be thermophilic. Moreover, it is a further preferred embodiment that the double stranded SDA amplification product produced during primer extension become hemimethylated or hemiphosphorothiolated (or other hemimodified form known to those skilled in the art) so that the double stranded SDA amplification product can be properly "nicked" at the primer restriction site for normal SDA amplification. For example, the substituted deoxynucleosidetriphosphate should be modified such that it will inhibit cleavage in the strand containing the substituted deoxynucleotides but will not inhibit cleavage on the other strand. Examples of such substituted deoxynucleosidetriphosphates include 2'-deoxyadenosine 5'-O-(1-thiotriphosphate), 5-methyldeoxycytidine 5'-triphosphate, 2'-deoxyuridine 5'-triphosphate, and 7-deaza-2'-deoxyguanosine 5'-triphosphate.

In an alternative preferred embodiment, a restriction site may be used in the SDA procedure that does not require the nucleic acid backbone of the restriction site to be modified as described above. For example, BstNBI may be used in connnection with its restriction site to nick the nucleic acid as it does not require modification to achieve single stranded nicks. Instead, BstNBI performs single stranded nicks as a natural activity.

The nucleic acid segments of the primer pair complementary to target sequence may be any useful length that will allow hybridization under temperature and buffer conditions appropriate for proper function of SDA on the microchip. Typically, the target sequences of the primer pair have sequence that is complementary with portions of target nucleic acids that are spaced anywhere from 60 to 120 bases upstream or downstream, as the case may be, from one another. In all cases each primer of the primer pair is complementary to different strands (i.e., the plus strand or the minus strand) of the target sequence. Additionally, where the primer pair is on a branched moiety the spacing between the primers on the branched connecting moiety may be adjusted by molecular spacer elements to optimally enhance the efficiency of the SDA reaction. Such spacer elements may comprise polyethylene glycol polymers, polyamino acids, or nucleic acids.

In another preferred embodiment, the spaced primers may be attached to a branched molecular structure (e.g., a 'Y' shaped structure) at their respective 5' termini. The branched structure is itself then anchored via a free branch of the Y to designated capture pad sites on the microchip. Attachment chemistry to the microchip surface may be by streptavidin/biotin coupling well known in the art. Alternatively, attachment chemistry may include chemistry comparable to that disclosed in any of U.S. Pat. Nos. 5,668,258, 5,668,257, 5,677,431, 5,648,470, 5,623,055, 5,594,151, and 5,594,111, herein incorporated by reference. In one preferred embodiment, the branched molecules are formed by nucleic acids attached to an amino acid. In another alternate embodiment, the branched molecules are formed by adding different spacers, such as polyethylene glycol polymers, polyamino acids, or nucleic acids between the nucleic acid primers and a bifunctionally branched amino acid (e.g. lysine).

In yet another embodiment, the anchored SDA amplification primers need not be branched but instead merely anchored individually to the capture site in close proximity to each other. Attachment chemistry may be accomplished as described above.

In another preferred aspect of the invention, amplification of target nucleic acids is carried out exclusively at the site of an anchored primer pair thereby avoiding the uncertainties of amplification rate commonly associated with solution-based amplification. Particularly, as compared with solution-based amplification, the amplification of multiple targets or multiplex amplification is markedly improved. It is probable that such improvement is due to the avoidance of competition between primers and/or avoidance of primer-primer interactions that may inhibit binding to target sites. Amplification is kept at one location by the combined influence of electronic addressing of target molecules and SDA products to capture pad SDA sites and by the fact that the primers that allow amplification (i.e., the branched or unbranched primer pairs) are anchored to a fixed location.

In another preferred aspect of the invention, the target nucleic acid is electronically addressed to the specific site on the microchip prior to amplification. This aspect is an advance over passive hybridization technology in several ways. First, since nucleic acids in a sample solution containing target nucleic acid species are electronically addressed to specific sites on the microchip, the target molecules have a preferred advantage of contacting the primer pair designed to capture the target molecule. Secondly, in the event single stranded nucleic acid target molecules must be generated, conditions in the sample solution that allow for formation of single stranded species must only be accomplished once rather than repeatedly as is normally the case with PCR and solution-based amplification. Third, the electronic addressing and annealing of the target species to specific capture sites on the chip may be carried out in low salt conditions, a situation that is markedly in contrast to classical passive hybridization technology. Low salt conditions (and electronic addressing) enhance the hybridization of single stranded target species to capture primers because such conditions help reduce the reannealing of target nucleic acid strands to their respective complementary strands.

In another preferred embodiment, the anchored SDA methods of the current invention provide improved efficiency because only one target specific "bumper" primer is required for annealing to the target molecule at a position on the target 5' to the target annealing position of one or the other anchored primers. In another embodiment, two bumper primers may be included (as in traditional SDA) but inclusion of two primers is not necessary. Rather, the use of two bumper primers only facilitates initiation of priming from either direction on any one pair of primer capture probes depending upon which of the two strands of target nucleic acid are first captured by the branched primer pair. Inclusion of two bumper primers may further enhance the rate of amplicon formation.

In yet another aspect of this invention, a method of amplification of a target nucleic acid sequence (and its complementary strand) in a sample using SDA under elevated pressure is provided. By elevating the pressure, the efficiency of the amplification is enhanced because the specificity of the restriction endonuclease for its target sequence is increased. The method involves the steps of 1) isolating nucleic acids suspected of containing the target sequence from a sample, 2) generating single stranded fragments of target sequences, 3) adding a mixture comprising (a) a nucleic acid polymerase, (b) deoxynucleosidetriphosphates, a phosphorothioated dNTP, endonuclease, and (c) at least one primer which (i) is complementary to a region sometimes at or along a portion of the target near the 3' end of a target fragment, and (ii) further has a sequence at its 5' end which is a recognition sequence for a restriction endonuclease, and 4) allowing the mixture to react under elevated pressure for a time sufficient to generate amplification products. Where the target nucleic acid fragments comprise double stranded nucleic acids, the method further comprises denaturing the nucleic acid fragments to form single stranded target sequences. Where the nucleic acids comprise RNA, it is preferable to first use reverse transcriptase in order to convert RNA to DNA, however, RNA is specifically included in all embodiments of the invention.

In a further embodiment, a method of SDA in conjunction with an electronic microchip is provided wherein the SDA reaction is ligation-based. In this embodiment, two sets of primers are used wherein one primer set is designed so that the primers bind to one strand of a target sequence adjacent to one another while each of the primers of the second set are designed to bind to a portion of one of the primers of the first primer set while the other of the second primer set is complementary to a portion of the other of the first primer set (i.e., same as the target strand sequence). When this embodiment is used, it will be apparent that SDA may be accomplished without the involvement of bumper primers. In a preferred embodiment, one of the two primer sets may be "anchored" as described herein.

In another embodiment, a method of ligation-based SDA is provided where the method is unassisted by an electronic microchip. In this embodiment it is not necessary to, inter alia, anchor any primers, which is a procedure that assists in separating primer sets during multiplex amplification, because the primers are universal—there is no need to direct target sequences to the 'correct' primers.

In a particular embodiment of the ligation-based SDA method, the probe set designed to anneal to a target sequence must become ligated to form a "ligated probe template" which template is capable of supporting SDA. In a further preferred embodiment, the ligation-based reaction uses a single pair of amplification primers (i.e., the second primer set mentioned above) which are universally applicable to amplification of all target molecules in a multiplex test providing in turn for decreased non-target amplification as well as decreased primer competition interactions due to the absence of bumper primers.

In a further preferred embodiment, the ligated probe template is modified so that it can not be extended from its 3' end during initial SDA reaction steps. Modifying the relevant ligation probe prevents the formation of a double stranded nucleic acid the 3' end of which may be cleaved by restriction endonuclease due to formation of what would be a cleavable restriction site, as explained in more detail below. This modification also prevents amplification of ligated probe template that may result from the target-sequence-independent ligation of the ligation probes.

In another preferred embodiment of the ligation-based SDA method, the pair of probes used to target a nucleic acid of interest and create a ligation probe template are bifunctional in that each probe of the pair contains a target binding sequence and an "amplification primer" binding sequence (i.e., the second primer set mentioned above). The sequences specific for target binding are chosen so that they are complementary to adjacent sequences of target DNA. The portions of the ligation probe template primers having nucleic acid sequence used in amplification are chosen so that a single set of amplification primers can be used for all target species of interest during SDA.

In a further embodiment, a first amplification primer binds to the ligated probe template at the 3' end of the ligated probe template such that there is created two 5' overhangs. See FIG. 23(a). Double stranded nucleic acids with 5' overhangs are normally capable of supporting nucleic acid synthesis from the 3' end of the recessed strand by a DNA polymerase. As is well known in the art, DNA polymerase functions by extending the length of one strand of a nucleic acid by incorporating bases to the strand that are complementary to the opposing strand.

However, in a further preferred embodiment, nucleic acid synthesis from the 3' terminus of the ligated probe template is prevented due to the 3' terminus having a modification to keep it from extending. Those in the art understand that this modification may take many forms including but not limited to: creating a 3' base mismatch between the ligated probe and the amplification primer; using a 3' terminal dideoxy nucleotide; or modifying the chemical moiety present at the 3' carbon of the pentose sugar of the nucleic acid backbone by, for example, replacing the free 3' hydroxyl group with a phosphate group, a biotin moiety, or by adding other blocking groups which are well known to those in the art. (See U.S. Pat. Nos. 5,516,663 and 5,573,907 and 5,792,607, incorporated herein by reference, discussing various reagents that can be used to modify ends of the ligation probes to prevent target independent ligation). This modification prevents the formation of a double stranded nucleic acid which could be improperly "nicked" by endonuclease during the ligation-based amplification process. This modification also prevents amplification of ligated probe template that may result from the target sequence independent ligation of the ligation probes and prevents 3' extension when ligated probe is bound to primer. This modification also allows the ligation and amplification reactions to proceed without an additional capture step.

In a further preferred embodiment, the ligation probes are designed to include sequences encoding endonuclease restriction sites, such that these sites are located near the 5' and 3' ends of the ligated probe template. Restriction endonuclease present in the reaction mixture may nick the double stranded nucleic acid so that SDA may proceed. Nicking of the DNA rather than cleavage occurs because the strand complementary to the 5' end of the ligated probe is synthesized during SDA using nucleotides that include a modified nucleotide (for example dATP$_\alpha$S, or dCTP$_\alpha$S).

In a further embodiment, the amplicons arising from ligation-based SDA may be addressed to capture sites following their respective formation (whether their amplification is made to occur by SDA in solution or directly on the capture sites by primers that are addressed to the capture sites prior to amplification as described herein).

In yet another embodiment of the invention, several means by which the presence of target nucleic acids in a sample may be detected are available due to the combined application of the electronic addressable chip and anchored SDA. For example, in a preferred embodiment, amplicons that are addressed to capture sites may be discerned directly by fluorescence, i.e., a fluorochrome may be included in the buffer so that detection is simultaneous with the production of amplicons. Examples of such fluorescing compounds include Bodipy-derivatives, Cy-derivatives, fluorescein-derivatives, and rhodamine-derivatives all of which are well known in the art. Alternatively, detection of nucleic acids at capture sites may be carried out directly using chemiluminescence or electrochemiluminescence. Chemiluminescence incorporates the use of an enzyme linked to a reporter oligonucleotide which, when activated with an appropriate substrate, emits a luminescent signal. Examples of such enzymes include horseradish peroxidase and alkaline phosphatase both of which are well known in the art. Electrochemiluminescence (ECL) is a highly sensitive process (200 fmol/L) with a dynamic range of over six orders of magnitude. In this system, reactive species are generated from stable precursors at the surface of an electrode. These precursors react with each other to form the excited state of the label attached to the DNA strand. The excited state decays to the ground state through a normal fluorescence mechanism, emitting a photon having a wavelength of 620 nm.

The amplification products generated using the primers disclosed herein may also be detected by a characteristic size, for examle, on polyacrylamide or agarose gels stained with ethidium bromide. Alternatively, amplified target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al. (1992, *Nucl. Acids Res.* 20:1691–1696) (a detector primer) or by hybridization, extension and conversion to double stranded form as described in EP 0678582 (a signal primer). Preferably, the assay probe is selected to hybridize to a sequence in the target that is between the amplification primers, i.e., it should be an internal assay probe. Alternatively, an amplification primer or the target binding sequence thereof may be used as the assay probe.

The detectable label of the assay probe is a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label that requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigen/habpens). Ligands are also useful immobilizing the ligand-labeled oligonucleotide (the capture probe) on a solid phase to facilitate its detection. Particularly useful labels include biotin (detectabel by binding to labeled avidin or streptavidin) and exzymes such a horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods that may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a steptavidin-coated microtiter plate by means of the capture probe, and the chemiluminescent signal is developed and read in a luminometer. As another alternative for detection of amplification products, a signal primer as described in EP 0678582 may be included in the SDA reaction. In this embodiment, labeled secondary amplification products are generated during SDA in a target amplidication-dependent manner and may be detected as an indication of target amplification by means of the associated label.

In another alternative detection method, a target specific primer, (i.e., a target signal primer which is a primer that is not a bumper primer or an anchored primer), designed to anneal to the target sequence at a position other than at the anchored primer or bumper primer sites may be included in the amplification step procedure. This signal primer may be labeled with a signal molecule that may in turn be used to detect an extension product formed from extension of the signal primer during SDA. For example, such label may comprise biotin that may be captured to a microchip location containing streptavidin which capture may be detected by presence of a fluorochrome.

In still another aspect of the invention, use of a signal primer elongation product or amplicon provides for a means by which the molar ratio of one target amplicon strand over the other may be produced so that single stranded amplified species of the target sequence may be maintained for capture by capture probes located at specific sites on the microchip. In other words, the signal primer allows "asymmetric SDA". Moreover, the amplified signal primed amplicons may be electronically addressed to secondary capture sites which facilitates further reduction in background signal for enhanced detection.

For commercial convenience, amplification primers for specific detecion and identification of nucleic acids may be packaged in the form of a kit. Typically, such a kit contains at least one pair of amplification primers. Reagents for performing a nucleic acid amplification reaction may also be included with the target-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonuclotide tagged with a label suitable for use as an assay probe, and/or reagents or means for detecting the label.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 6A shows a fluoroscopic analysis of a microchip where the SDA template was absent as a control.

FIG. 6B shows a fluoroscopic analysis of a microchip where BsoBI was not included in the reaction as a control.

FIG. 6C shows a fluoroscopic analysis of a microchip where the SDA template was passively hybridized overnight.

DETAILED DESCRIPTION OF THE PREFERRED EMBODIMENTS

The present invention relates broadly to devices, methods, and compositions of matter for amplifying nucleic acid sequences in a sample and for analyzing those sequences. The amplification and the analysis are optimally accomplished using SDA and bioelectronic microchip technologies.

EXAMPLE 1

In a preferred embodiment of this invention, a microchip device comprising an electronically controlled microelectrode array is provided for the analysis of target nucleic acids of interest. In contrast to the uniform hybridization reaction environment and passive hybridization used in other microchip devices, the electronic microchip-based devices of the present invention offer the ability to actively transport and hybridize target and/or primer nucleic acids to capture probes at discrete locations on the surface of the microelectrode array.

Figure 1A:
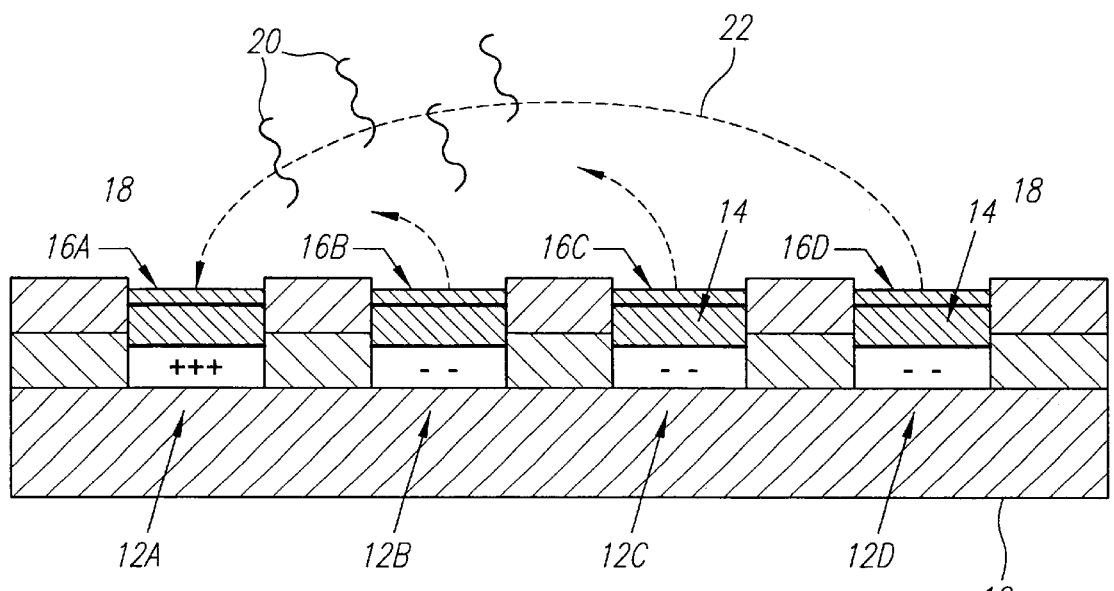
FIG. 1A shows a cross-sectional view of an embodiment of the bioelectronic chip of the present invention.
Figure 1B:
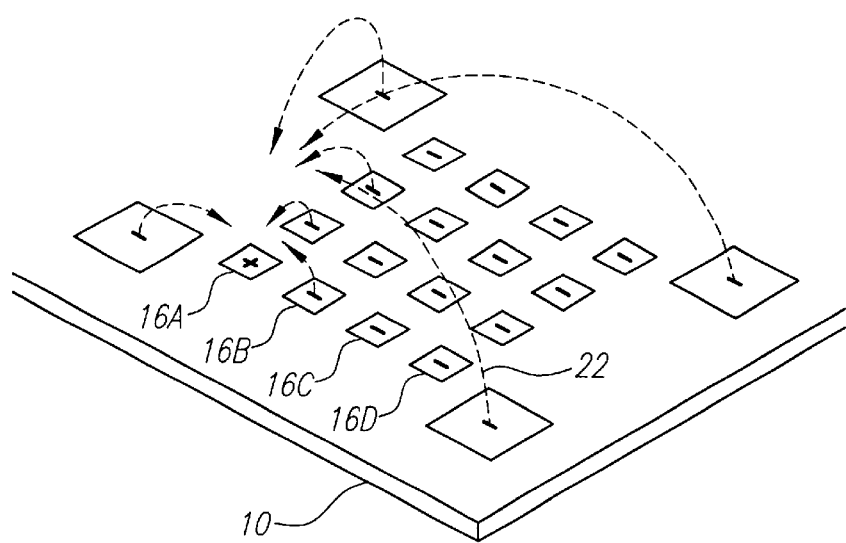
FIG. 1B shows a perspective view of the bioelectronic chip from FIG. 1A.

Referring now to FIGS. 1A and 1B, a simplified version of the electronically addressable microchip-based hybridization system embodied within this invention is illustrated. Generally, a substrate 10 supports a matrix or array of electronically addressable micro-locations 12 which may be any geometric shape such as square or circular. For ease of explanation, the various micro-locations in FIG. 1A have been labeled 12A, 12B, 12C and 12D. A permeation layer 14 is disposed above the electrodes 12 and may extend over the entire device surface. The permeation layer 14 permits transport of relatively small charged entities through it, but limits the mobility of large charged entities, such as nucleic acids, to keep the large charged entities from easily directly contacting the electrodes 12 that are located under the permeation layer of a capture site. The permeation layer 14 also reduces the electrochemical degradation that could occur if direct contact were made with the electrodes 12. Electrochemical degradation is sometimes induced by both formation of reactive radical species and extreme pH at the electrode surface during the electrolytic reaction. The permeation layer further serves to minimize the strong, non-specific adsorption of nucleic acids to electrode surfaces. Attachment regions or capture sites 16 are disposed upon the permeation layer 14 and provide for specific binding sites for target materials. The capture sites 16 in FIG. 1A have been labeled 16A, 16B, 16C and 16D to correspond with the identification of the electrodes 12A–D, respectively.

The central area of the microchip contains reservoir 18 for placing sample nucleic acids above the area containing the multiplicity of capture sites 16. In a preferred embodiment, charged molecules 20, such as charged target or probe nucleic acids located within reservoir 18 may be transported to any of the specific micro-locations 12. When activated, a micro-location 12 generates the free field electrophoretic transport of any charged molecule 20 (e.g., probe, target nucleic acids or amplicons) toward the electrode 12A. As a further example, addressing electrode 12A with a positive bias and electrode 12D with a negative bias, causes electrophoretic lines of force 22 to run between electrodes 12A and 12D and further cause the transport of charged molecules 20 having a net negative charge toward the positive electrode 12A. Charged materials 20 having a net positive charge move under the electrophoretic force toward the negatively charged electrode 12D. When the net negatively charged molecules 20 contact the capture sites 16A permeation layer as a result of its movement under the electrophoretic force, the charged molecule 20 becomes attached to the capture sites attachment layer 16A. Attachment may be by many methods as discussed below including attachment by hybridization of a target charged molecule 20 to a complementary nucleic acid probe that is anchored to the capture site 16.

Electronically addressable microchip arrays of the present invention overcome the size limitations of capture probe oligonucleotides and complexity requirements of passive microchip devices. The addressable microchip also greatly reduces the need for strand separation, at least in part, because of the use in the current system of a low ionic environment which inhibits the formation of double stranded nucleic acid that is in solution prior to capture and amplification of the nucleic acid at a capture site. In addition, the microchip arrays of the present invention allow multiple independent sample analyses (i.e., multiplex sample analysis) upon the same open microarray surface by selectively and independently targeting different nucleic acid samples to various microelectrode locations. In other words, they allow parallel multiple sample processing on an open array. As is described in detail below, the capability of electronic targeting to overcome the above-described limitations of passive hybridization methods is demonstrated in the following two examples A and B.

Example A
Parallel Analysis of Single Target Nucleic Acids in a Sample

In a first example, a parallel analysis of the capture and detection of a single nucleic acid in a test sample was performed using a common locus (16S rRNA) shared by different bacterial species. Multiple comparative analyses of individual samples were used to identify different bacteria types.

The secondary structural requirements of the 16S ribosomal RNA subunit demands highly conserved nucleic acid sequences in the 16S rRNA gene. Thus, there is limited sequence divergence in this gene between different species of bacteria. Despite the overall high sequence conservation, there are pockets of microheterogeneities within the 16S rRNA gene, which can be exploited to discriminate between closely related bacterial species. See, e.g., C. Woese, 51 *Microbiol Revs.* 221–271 (1987).

Figure 2A:
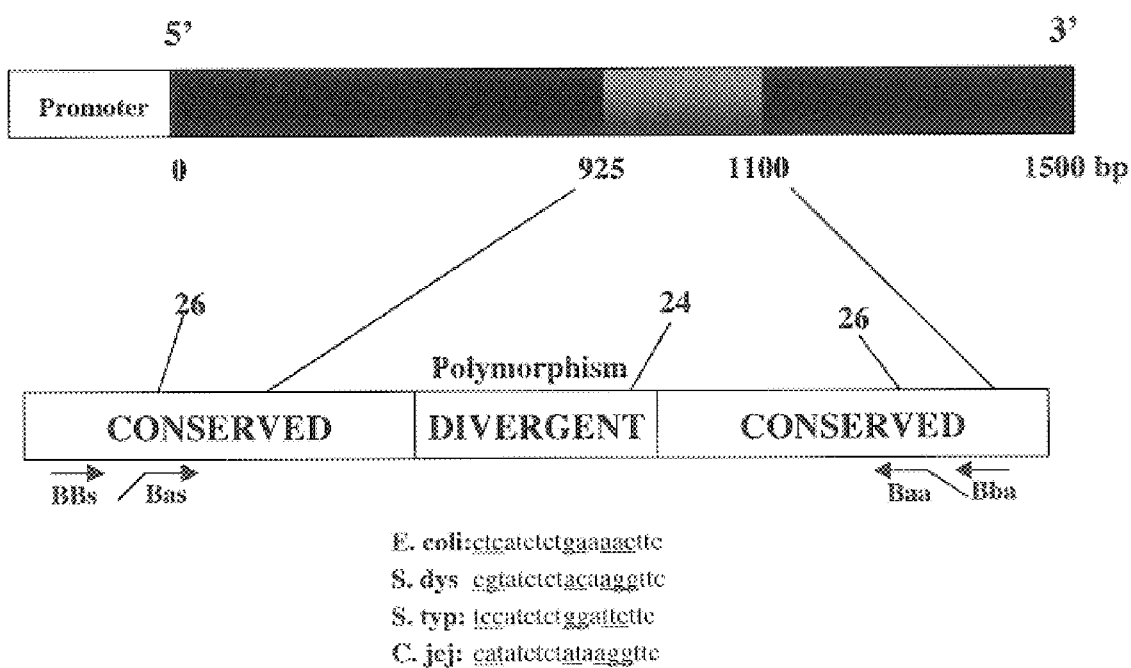
FIG. 2A shows a schematic representation of a bacterial 16S rRNA gene comprising a divergent region (having a different sequence per bacterial strain) flanked on both sides by conserved regions (having the same sequence in each bacterial strain). BBs and Bba represent bacterial sense and antisense bumper primers respectively. Bas and Baa represent bacterial sense and antisense amplification primers respectively. Identification of the bacterial strains tested are in the sequence listing.

The bracketing of these microheterogeneities by conserved sequences provides opportunities to design many primers for consensus amplification (i.e. uniform amplification using the same primers regardless of species) for almost all bacterial species containing the conserved sequences. As shown in FIG. 2A, SDA primers were designed in the conserved regions that flank the polymorphic region and used in SDA reactions. The resulting amplicons included the various sequences of the "microheterogeneity domains" of the 16S rRNA genes. These were analyzed by a variety of methods.

As demonstrated below, consensus SDA primers can be used for the generation of species-specific amplicons which in turn can be readily analyzed by hybridization on active microelectronic arrays. Similar studies have been reported using PCR as a means of target amplification. See, e.g., D. Linton, et al., 35 *J Clin. Microbiol* 2568–72 (1997), M. Hughes, et al., 35 *J Clin. Microbiol.* 2464–71 (1997). However, the present invention uses a sandwich assay in which a single-stranded capture probe is electronically deposited on the array, and serves to capture one strand of a charged molecule such as a target nucleic acid or amplicon thereof. In a preferred embodiment, a multiplicity of molecules such as nucleic acid capture probes can be electronically deposited on different pads of the array. Following capture of the charged molecule to the capture sites, the captured molecule may be detected by a labeled reporter probe that binds to the captured molecule.

As is shown schematically in FIG. 2A, the 16S rRNA gene near its 3' end has an oligonucleotide region stretching greater than twenty contiguous nucleotides of polymorphic sequence 24 flanked on both sides by conserved sequences 26. The unique sequences 24 of each bacterial species specified in the sequence listing herein were used in an SDA reaction in the electronically addressable microchip to show that it is possible to discriminate between different bacterial species by capturing these polymorphic sequences and their respective amplicons at specific capture sites. More particularly, primers were designed having nucleic acid sequence complementary to the highly conserved loop III structure of the small subunit of the bacterial ribosomal RNA 26. A 3' base complementary to a species-specific allele or point mutation in the sequence were also designed and made. As shown in FIG. 2A, this primer configuration facilitates design of both SDA amplifier and bumper primers for any particular group of organisms having the same conserved nucleic acid sequences. Primers can also be made so that they are "universal" for use in SDA to detect organisms of a group.

Figure 2B:
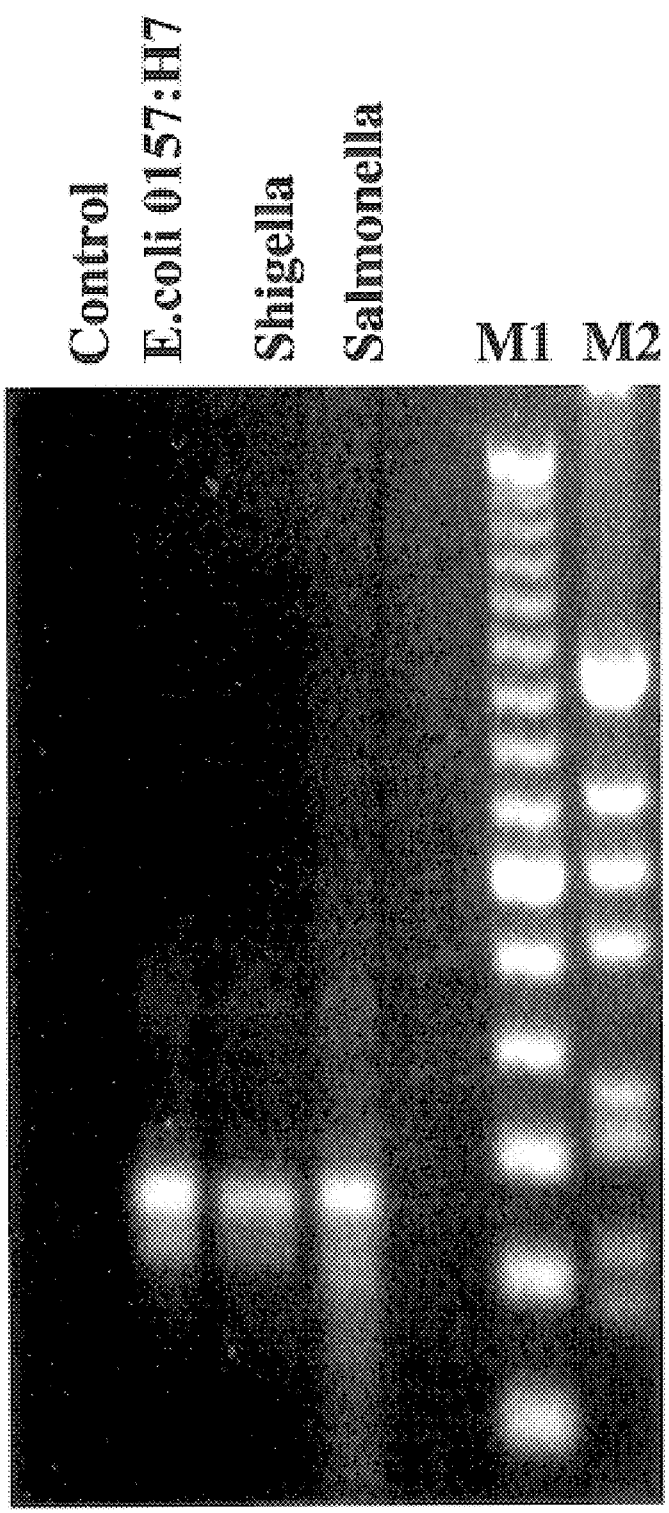
FIG. 2B shows the results of 16S rRNA encoding SDA amplification products resolved on a 1% agarose gel stained with ethidium bromide showing specific amplification of the divergent regions from each strain.

In a specific example, genomic DNA from bacteria (*E. coli* O157:H7, *Salmonella typhimurium*, *Shigella dysenteriae*, and/or *Campylobacter jejuni*) were amplified. The same set of 16S rRNA encoding "consensus" primers (described in more detail below) were employed in each SDA reaction. The products of the SDA reactions were resolved on a 2% agarose gel to compare the amplification efficiencies between different bacterial species. The resulting gel is shown in FIG. 2B wherein similar levels of amplification efficiency were obtained for each of *E. coli* O157:H7, *Salmonella typhimurium*, and *Shigella dysenteriae*, and in other experiments utilizing genomic DNA from *Campylobacter jejuni* (data not shown). Table I, below, shows the oligonucleotide sequences used for amplification and microarray analysis of these bacterial species.

Figure 2D:
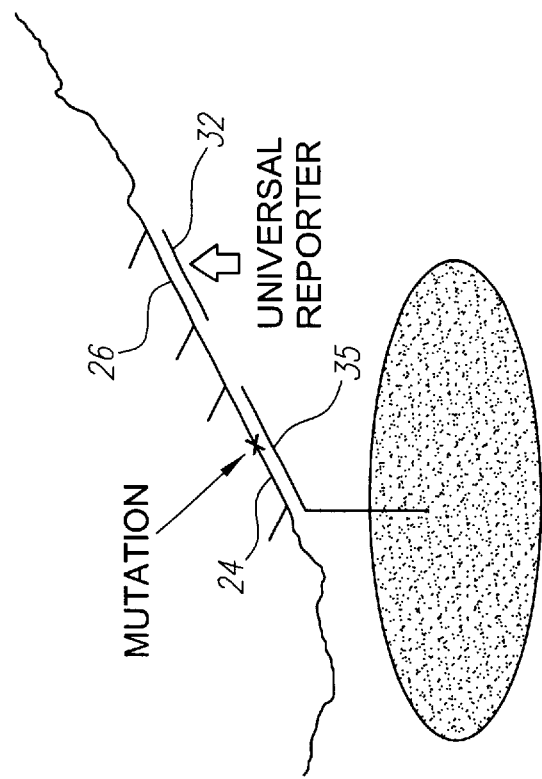
FIG. 2D shows a sandwich assay format used for nucleic acid hybridization on microarrays of the present invention wherein the assay format utilizes a sequence specific capture probe and a universal reporter.
Figure 2C:
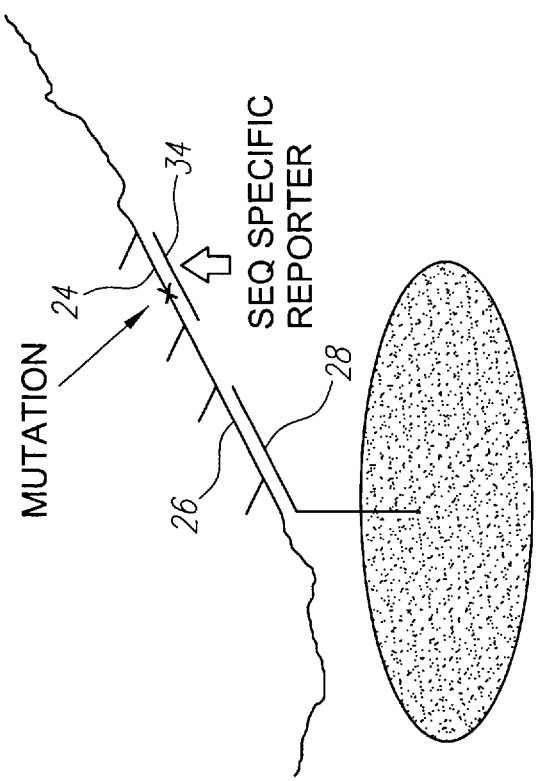
FIG. 2C shows one aspect of a sandwich assay format used for nucleic acid hybridization on microarrays of the present invention wherein the assay format utilizes a universal capture probe and a sequence specific reporter.

Two different approaches were used to analyze the amplification products. A first analysis approach used a common or universal capture probe and a sequence specific reporter (i.e. a universal capture/specific reporter method). A second analysis approach used discriminating capture primers and a universal reporter (i.e. a specific capture/universal reporter method). As is shown in FIGS. 2C and 2D, universal capture probes 28 and universal reporters 32 were designed to span at least a portion of one of the conserved regions 26 (FIG. 2A) of the gene. As is also shown in FIGS. 2C and 2D, sequence specific capture probes 35 and sequence specific reporters 34 were designed to span at least a portion of the polymorphic region 24 (FIG. 2A).

Where universal capture probe 28 was used to capture nucleic acids, the initial step of hybridization between a target nucleic acid and a universal capture probe was performed electronically for several reasons. First, electronic hybridization greatly accelerates the kinetics of hybridization which is important when working with low concentrations of material, such as a highly diluted target or amplicon. Second, because of the extremely low ionic strength of the buffer systems used, targets and amplicons remain single stranded facilitating capture by probes and much less competition from the complementary strand of target or amplicon and, hence, higher net specific binding of the nucleic acid to the capture probe. Consequently, electronic hybridization allows a much higher level of nucleic acids hybridizing at the site of the capture probe resulting in greater detection and discrimination sensitivity.

In each case of this example, reporter hybridization was passive, i.e. performed at elevated salt and temperature without the aid of electronics, although electronics could be used. In this particular example, since the concentration of the single stranded labeled oligonucleotides was so high, there was little practical kinetic advantage to be obtained through the use of electronic hybridization conditions. However, under different circumstances, the use of electronics during reporter hybridization may be beneficial.

Figure 3A:
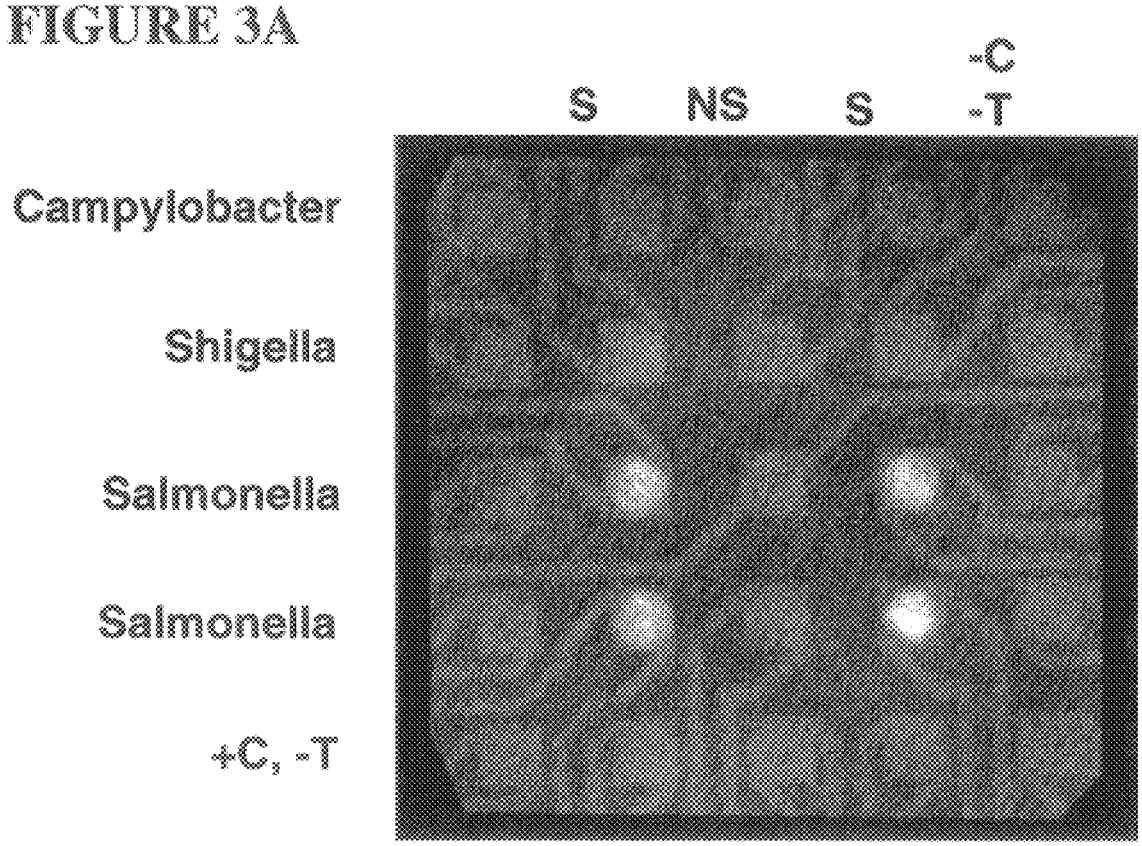
FIG. 3A shows Salmonella-specific BTR labeled reporter used for passive hybridization of SDA amplicons on a microarray wherein the capture sites of the microarray include as a control for non-specific binding of the reporter oligonucleotide to the capture probes or permeation layer itself a site containing capture probes but no target (+C/−T) and a site containing no capture probe or target (C−/T−).
Figure 3B:
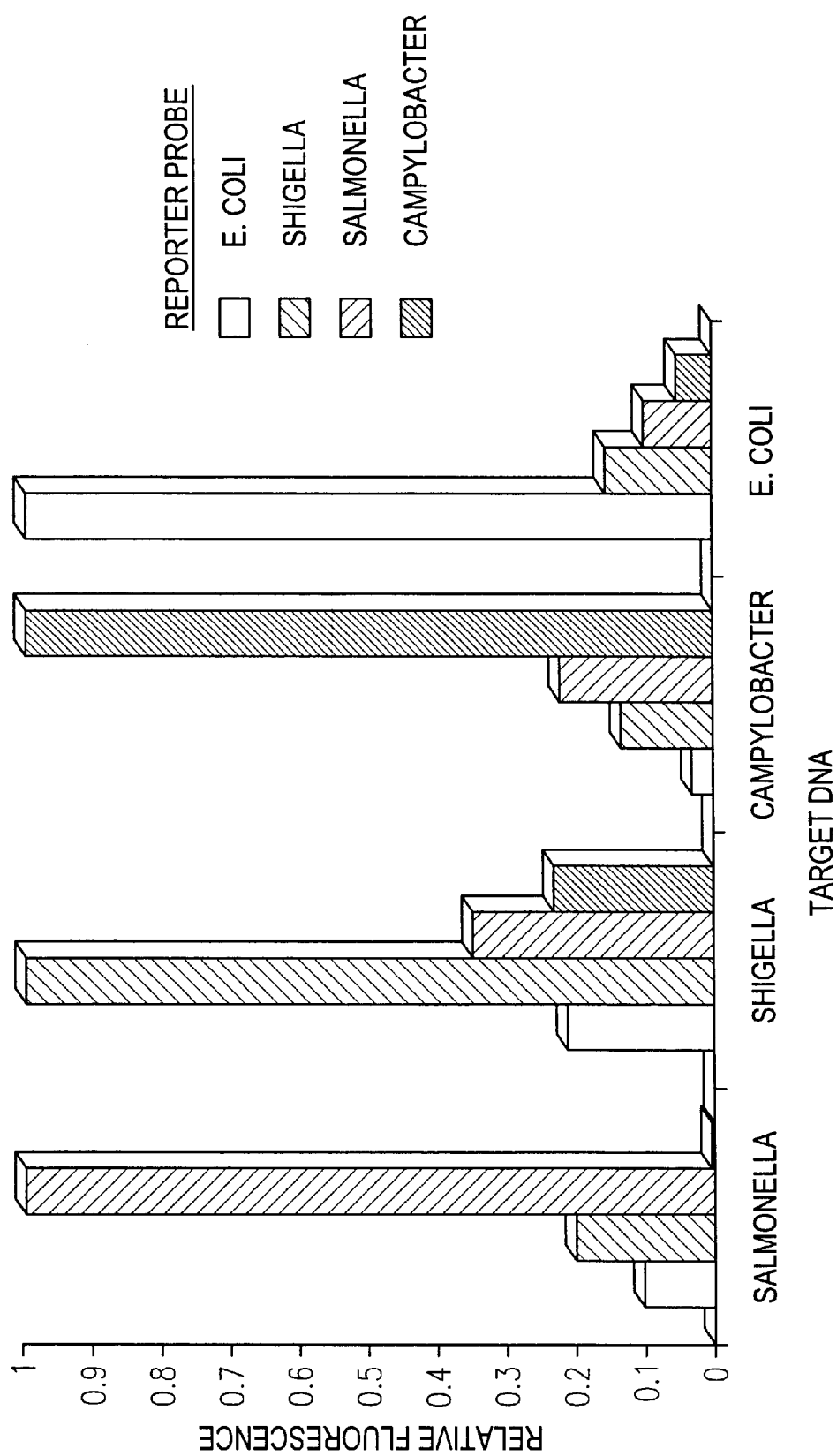
FIG. 3B shows a comparison of the relative fluorescence observed for each bacteria when SDA amplicons were generated and electronically addressed to individual sites on a microarray using universal capture probes, and sequence-specific btr-labeled reporter probes (designed in the divergent region of the 16S rRNA gene) were passively hybridized to discriminate various bacterial strains.
Figure 3C:
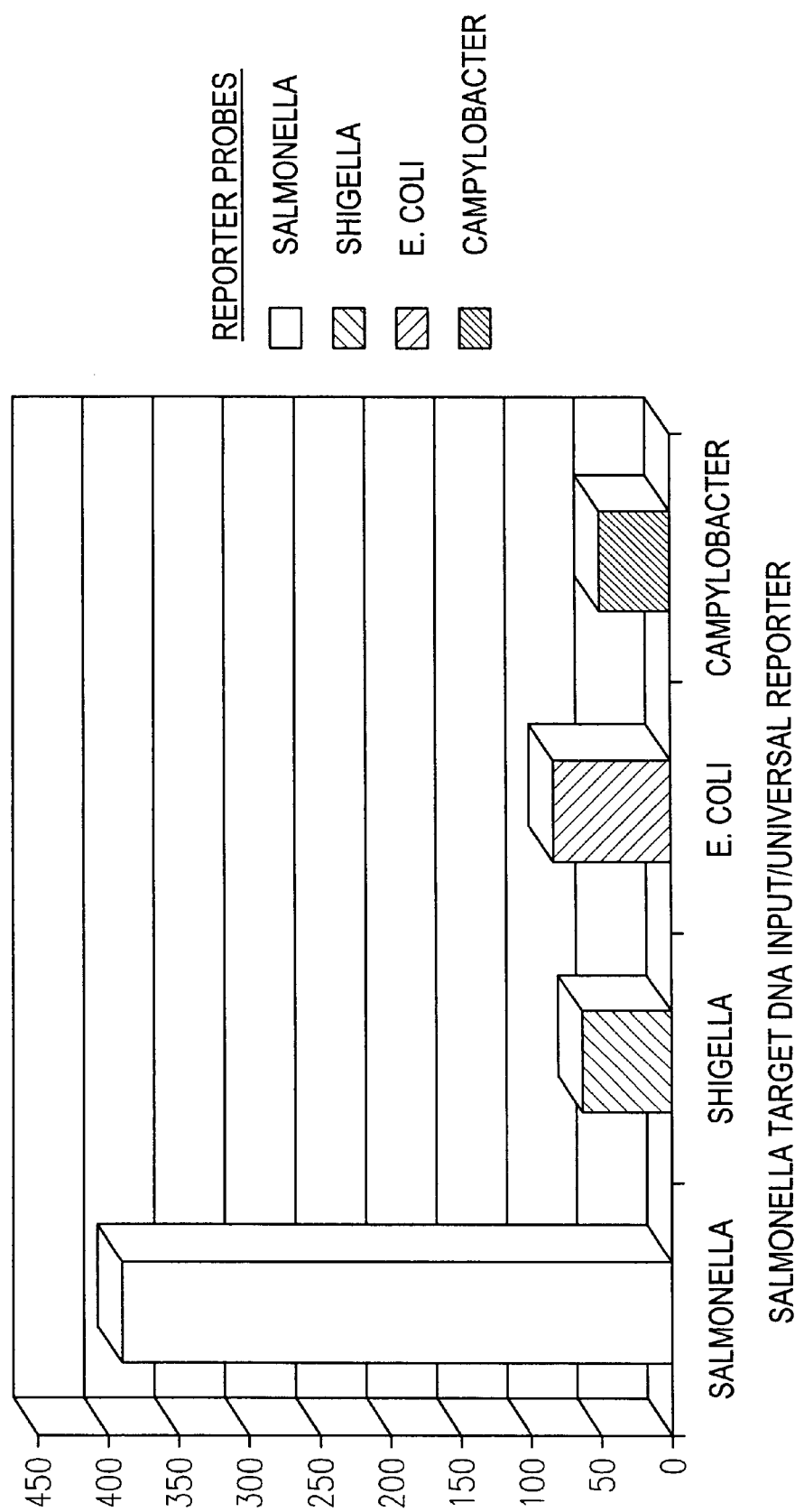
FIG. 3C shows a comparison of the relative fluorescence observed for each bacteria when SDA amplicons were generated and electronically addressed to individual sites on a microarray using sequence-specific capture probes, and universal btr-labeled reporter probes (designed in the conserved region of the 16S rRNA gene) were passively hybridized to the captured material.

As shown in FIG. 3A, amplicons were addressed to the capture sites on the microchip and detected by a fluorescent reporter molecule (as described below). The relate fluorescence on capture sites to which were hybridized amplification products of bacterial 16S rRNA targets discussed in FIG. 2A were highly discriminated (i.e., a polymorphism specific Salmonella reporter, a polymorphism Shigella reporter, and a polymorphism Campylobacter reporter). In these experiments, universal capture probes ("S") were first addressed to the microchip along with a non-specific capture probe ("NS") as a control. Amplicons from each strain-specific SDA reaction were then addressed to each corresponding row and passively hybridized with a specific reporter probe. FIG. 3A shows results for Salmonella-specific reporter. As a control for non-specific binding of the reporter probe to the permeation layer, a minus capture/minus target control was also performed (−C/−T). As shown, only the Salmonella amplicon addressed capture sites gave a positive signal. As shown in FIG. 3B, not only were high discrimination ratios obtained for Salmonella as shown in FIG. 3A, high discrimination ratios were also seen between the various other bacterial targets. (fluorescent imaging data not shown.)

Where sequence specific capture probes 35 were used to capture nucleic acids, the initial step of hybridization between target and capture probe was also performed electronically. As in the universal capture example above, The reporter sequence was designed to recognize a conserved region of the 16S rDNA amplicons 26. As shown in FIG. 3C, this approach provided even higher discrimination ratios between the match and the mismatch.

Example B
Simultaneous Analysis of Multiple Target Nucleic Acids

In a second example, multiplex amplicon analysis was performed on the electronic microarray of the present invention. In this example, target nucleic acids from multiple patient samples were sequentially addressed to capture sites in order to detect the presence of the human Factor V Leiden (R506Q) gene (which indicates a predisposition to activated protein C resistance and venous thrombosis). In this example, capture probes were designed so as to be specific for alleles of the R506Q gene thereby providing a method to detect allele-specific SDA.

As explained herein, since each capture site on the open microarray may be individually electronically controlled, multiple samples may be analyzed. Following amplification and position-specific targeting of each sample amplification reaction, the array was evaluated in a site-specific fashion for the presence or absence of targeted amplicons. The test system examined the presence or absence of the human Factor V Leiden mutation in several blood samples. See, X. Liu, et al., 4 *Mol. Pathol.* 191–197 (1995). The Leiden mutation is a single point mutation at the protein C cleavage site of the Factor V gene. Where this mutation has a homozygous presence in a patient, it leads to activated protein C resistance and a predisposition to deep venous thrombosis. See, e.g., R. Bertina, et al., 369 *Nature* 64–67 (1994).

Figure 4A:
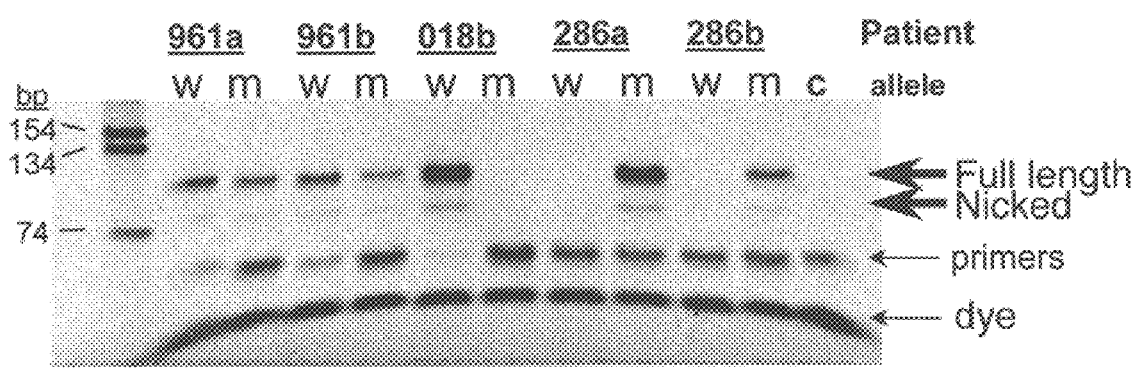
FIG. 4A shows a polyacrylamide gel analysis of the allele-specific reactions from five patient samples analyzing for Factor V Leiden mutation in each wherein each genomic DNA sample was amplified twice with allele-specific SDA using either the normal genotype (Factor V R506), W, or the Leiden mutation (Factor V Q506), M.
Figure 4B:
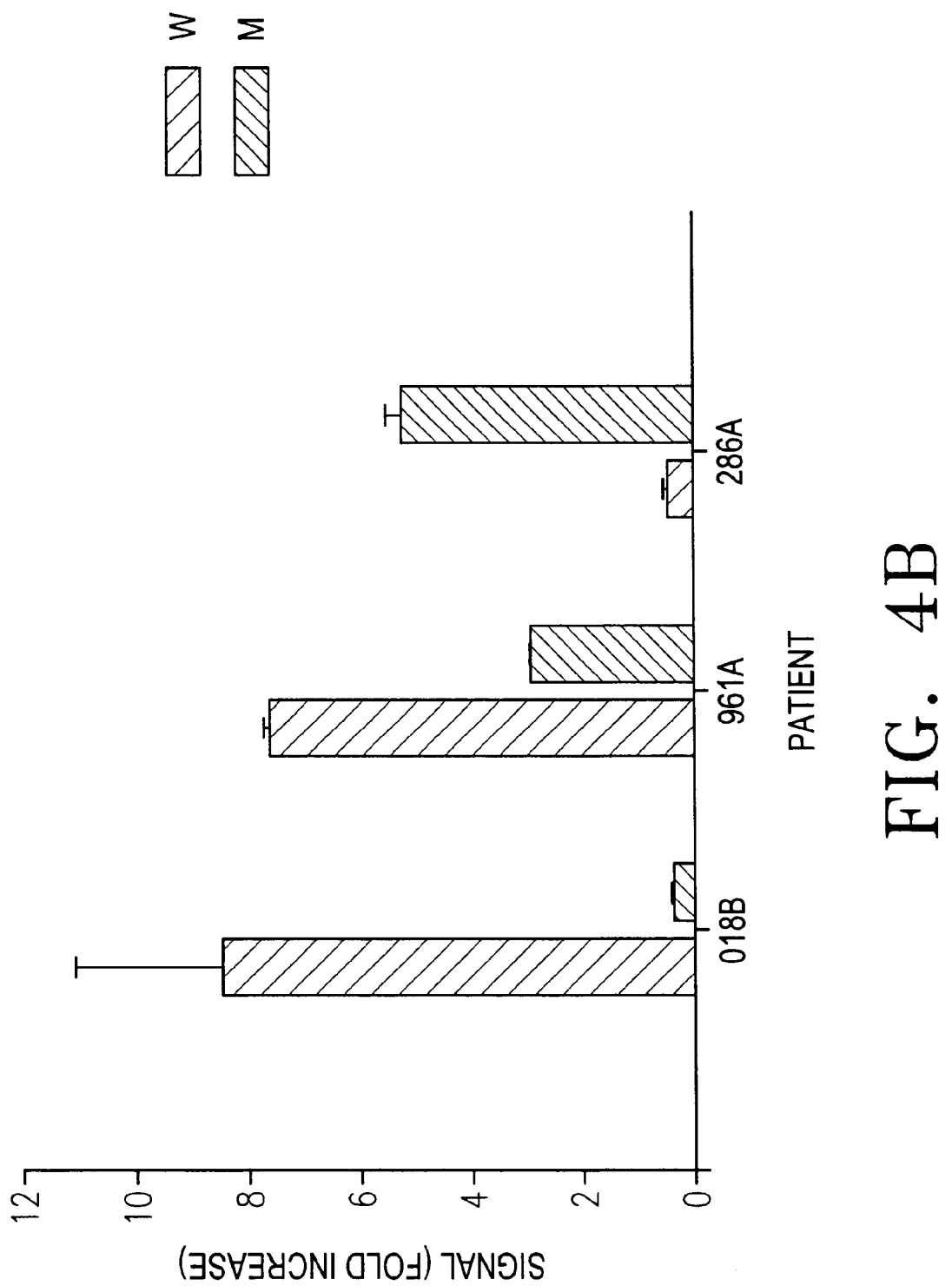
FIG. 4B shows a histogram comparing the fluorescence present at each addressed site on the array of the allele-specific reactions from three of the five patient samples of FIG. 4A.

To aid in discrimination, an allele-specific SDA assay was developed. The allele-specific SDA was designed to selectively amplify either the normal or the mutant Factor V Leiden allele. The SDA amplifying primers in the antisense orientation were designed with their 3' termini complementary to either the normal nucleotide base G, or the Leiden point mutation nucleotide base A, present in the sense strand of exon 10. Table I, below, shows the oligonucleotides used for amplification and microarray analysis of the Factor V gene. The corresponding sense primer was common in all reactions. However, the sense primer was modified by incorporating a biotin moiety on its 5' end in order to provide a facile mechanism for capturing any amplicons on the array following electronic targeting.

three DNA patient samples are shown in FIG. 4B. These samples were targeted in duplicate. The presence or absence of a fluorescent signal from a hybridized reporter oligonucleotide complementary to a conserved region on the target amplicon (i.e., a "universal" reporter probe) indicates

TABLE I

Oligonucleotides Used for Amplification and Microarray Analysis

| | Sequence (5'–3')[1] | | Position[2] |
|---|---|---|---|
| Bacterial 16S | | | |
| BBs | CAAATGAATTGACGGGGCC | (SEQ ID NO.1) | 927–946 |
| Bba | AAGGGTTGCGCTCGT | (SEQ ID NO. 2) | 1134–1120 |
| Bas | ACCGCATCGAATGCATGTCCTCGGGTGCA TGTGGTTTAAT | (SEQ ID NO. 3) | 961–975 |
| Baa | ACGATTCAGCTCCAGACTTCTCGGGTAAC ATTTCACAACAC | (SEQ ID NO. 4) | 1114–1090 |
| Br ecoli | btr-CTCATCTCTGAAAACTTC | (SEQ. ID. NO. 11) | |
| Brsdys | btr-CGTATCTCTACAAGGTTC | (SEQ. ID. NO. 12) | |
| Brstyp | btr-TCCATCTCTGGATTCTTC | (SEQ. ID. NO. 13) | |
| Brcjej | btr-CATATCTCTATAAGGTTC | (SEQ. ID. NO. 14) | |
| Human Factor V | | | |
| FVBs | ACTACAGTGACGTGGACATC | (SEQ. ID. NO. 5) | |
| FVBa | TGTTATCACACTGGTGCTAA[3] | (SEQ ID NO. 6) | |
| FVAs | bio-ACCGCATCGAATGCATGTCCTCGGGTCTC TGGGCTAATAGGA | (SEQ ID NO. 7) | |
| FVA wt | ACGATTCAGCTCCAGACTTCTCGGGTAAT ACCTGTATTCCT*C* | (SEQ ID NO. 8) | |
| FVA m | ACGATTCAGCTCCAGACTTCTCGGGTAAT ACCTGTATTCCT*T* | (SEQ ID NO. 9) | |
| FVR | btr-CTGTATTCCTCGCCTGTC | (SEQ.ID. NO. 10) | |

[1]On amplifying primers, BsoBl recognition sites are boldfaced, genomic homology regions are underlined and Factor V allele-specific 3'termini are shown in italicized boldfaced type. The designation "bio"represents biotin conjugation and "btr"indicates fluorescent BODIPY Texas Red conjugation. FVR is reporter for Factor V, FVAs is sense strand for amplification while FVAwt and FVAm are amplification primers for wildtype and mutant respectively. FVBs and FVBa are sense and antisense bumpers for Factor V.
[2]Bacterial 16S sequence was obtained from GenBank, human Factor V sequence refers to GenBank accession #L32764.

In this multiplex Factor V gene study, four clinical DNA samples were analyzed in duplicate without prior knowledge of the patient's Factor V Leiden mutation status. Two allele-specific SDA reactions were conducted per sample (containing either normal or mutant primers) to examine each patient's genotype. The amplifications were conducted in parallel. The PAGE results from five of these pair-wise reactions is shown in FIG. 4A wherein the allele-specific amplification reactions under these conditions are shown to be highly specific. That is, the selective absence of visible mutant or normal-type amplicons indicates that the amplification reaction is sensitive to the presence or absence of the Factor V Leiden mutation in these individuals.

All amplicon reactions, regardless of the presence or absence of amplified material as determined by gel analysis, were uniformly treated and sequentially targeted to specific locations upon the microarray. Representative results from the presence or absence of Factor V amplicons. As can be seen, the fluorescent signal correlates well with the gel results shown in FIG. 4A.

As is shown in FIG. 4A, positive signals were several fold greater than background signals. In general, the true mutant signal was lower than that from wild type amplicons (as shown in FIG. 4B). The sites were scored simply by making the criteria for a positive signal to be at least twofold above the background fluorescence present at non-addressed capture sites. As shown in Table II, below, there was complete correlation between the presence of amplified material by gel analysis and the presence of strong or moderate fluorescent signals upon the array.

The strength of the fluorescent signal approximated the apparent quantity of amplified material. This was most striking in those samples with an apparently less efficient amplification reaction such as was seen with the DNA from patient 961a in FIGS. 4A and 4B. In short, these results show that multiple sample analysis by the serial application of samples followed by single reporter detection works using a microelectronic array, and shows that this process may serve to supplement or replace other forms of analysis, e.g. gel electrophoresis, in the same or similar analyses.

Since these samples were analyzed prior to knowledge of their mutational status, it was of interest to determine whether the apparent allele specificity of the amplification reaction did, in fact, correspond with clinical status. As is shown in Table II, below, the selectivity of the allele-specific amplification reaction was in complete agreement with the Factor V Leiden mutational status of each sample as determined by PCR and MnlI restriction site analysis. (R. Press, unpublished observations). Thus, combined with allele-specific SDA, analysis of amplicon product formation upon an electronically addressable array is a useful method for detecting genetic point mutations in multiple patient samples.

TABLE II

Allele Specific Factor V SDA Amplification Results

| | | PAGE[1] | | Microarray[1] | | |
|---|---|---|---|---|---|---|
| Patient | Sample Date | wt | mut | wt | mut | Genotype[2] |
| 951961 | 04/10/97 | X | X | X | X | Heterozygous |
| 951961 | 06/04/97 | X | X | X | X | Heterozygous |
| 952018 | 04/10/97 | X | O | X | O | Homozygous wt |
| 952018 | 06/04/97 | X | O | X | O | Homozygous wt |
| 960286 | 04/10/97 | O | X | O | X | Homozygous mut |
| 960286 | 06/04/97 | O | X | O | X | Homozygous mut |

[1]"X" indicates positive, "O" indicates negative.
[2]Genotype was determined by PCR-RFLP with Mln-1 resstriction enzyme by methods well known to those skilled in the art.

Experimental Protocol Used in the Above Described Data

Materials—Deoxynucleoside 5'-triphosphates (dGTP, dATP, TTP) were purchased from Pharmacia, Alameda, Calif. 2'-deoxycytosine 5'-O-(1-thiophosphate) (dCTPαS), BsoB1 restriction endonuclease and Bst polymerase were supplied by Becton Dickinson, Sparks, Md. Oligonucleotides were synthesized by Oligos, Etc., Wilsonville, Oreg.

SDA Amplification—Amplification reactions utilized either 1 μg of genomic DNA (16S) or 0.1 μg of genomic DNA (Factor V) in a volume of 30 μl. Amplification conditions and concentrations were adapted from that presented previously (see, C. Spargo, et al., 10 *Molecular and Cellular Probes* 247–256 (1996)) with the following changes: The 5' to 3' exonuclease deficient polymerase Bst replaced the exo-BCA polymerase, as disclosed and used in M. A. Milla et al., *Biotechniques*, v24, p 392–396, March 1998 herein incorporated by reference. For 16S amplification, 25U/reaction (Bst) and 60U/reaction (BsoB1) were used. Oligonucleotides employed for amplification reactions are shown in Table I above. Reactions were allowed to proceed for 30 minutes at 60° C. and then terminated by the addition of 10 μL of 100 mM EDTA and then stored at −20° C.

Gel Electrophoresis—Amplification reactions were analyzed using standard protocols with either 1% agarose gel or with 6% polyacrylamide mini gels (Novex, San Diego, Calif.) followed by ethidium bromide staining. Images were obtained using an AlphaInotech Chemimager (San Leandro, Calif.).

Electronic Microarray Analysis—The microelectronic array assembly has been described previously. See, R. Sosnowski, et al., 94 *J Poc. Natl. Acad. Sci. USA* 119–123 (1997). Electronic targeting of capture oligonucleotides (biotin-GGATGTCAAGACCAGGTAAGGTTCTTC, Genbank locus 988–1014 bp (SEQ ID NO. 15) and hybridization of amplicons (16S) or reporter oligonucleotide (Factor V) utilized conditions reported elsewhere. See, R. Sosnowski, supra, and C. Edman, et al., 25 *J Nucleic Acids Res.* 4907–4914 (1997). In brief, crude amplification reactions were either spun for two minutes through G6 columns (Biorad, Hercules, Calif.) preequilibrated with distilled water or dialyzed in multiwell plates (Millipore, Bedford, Mass.) for more than or about five hours against distilled water. The prepared samples were then mixed in a 1:1 ratio with 100 mM histidine and heated at 95° C. for five minutes prior to electronic addressing. For analysis of 16S amplicons, electronic hybridization of the amplicons was performed, followed by hybridization in 6×SSC of a fluorescent labeled oligonucleotide reporter homologous to a specific bacterial sequence. Specific nucleotide sequences are shown in Table I, above. Passive hybridization was allowed to proceed for 30 minutes at room temperature. The microchips were washed 5 to 8 times using 0.1×STE/1% SDS followed by 1×STE. Similar conditions were employed for the single target experiment above using the 16S bacterial rRNA sequence-specific Biotin-captures and a common btr-labeled reporter for detection. For analysis of Factor V amplicons, a fluorescent-labeled oligonucleotide (btr-CTGTATTCCTCGCCTGTC (SEQ ID NO. 10) was introduced in 6×SSC and allowed to hybridize for 30 minutes at room temperature. The array was then washed in 0.1×STE/1% SDS followed by 1×STE.

EXAMPLE 2

Turning now to the electronic amplification aspect of the present invention, target nucleic acid is electronically concentrated in the vicinity of anchored primers located on a capture site and used in an SDA or other amplification method. The target nucleic acid may be electronically concentrated and hybridized to binding molecules (e.g., capture probes) on the surface of the microchip capture sites prior to the introduction of SDA reaction components (i.e. enzymes, nucleotides, etc.) thereby increasing the efficiency and decreasing the time necessary for hybridization of target nucleic acid to the anchored capture primer on the capture site. Hybridizing the target nucleic acid to specific locations on the microarray prior to addition of SDA reaction components also permits the array surface to be washed to remove unwanted and possibly interfering non-target nucleic acids from the reaction environment. Thus, amplification reactions, such as anchored SDA, can benefit greatly by using an electronically addressable microarray system.

The components of the amplification reaction itself (without template and amplification primers) are introduced and the amplification reaction allowed to proceed. There are at least three advantages to employing electronic targeting of template molecules. The first is that the overall time and efficiency of the amplification process is dramatically improved since a major rate-limiting step (that of the time required for the template to find the anchored primers) is removed from the overall reaction rate. Also, the use of the electronic concentration and hybridization increases the number of target molecules at the selected site, as compared to non-electronic passive hybridization for an equivalent time period, thereby increasing the absolute numbers of starting template molecules for amplification resulting in improvement in both the overall yield of the amplification process and the sensitivity of the system to lower starting template numbers.

The second advantage is that discrete target nucleic acid samples can be applied to specific locations upon the array surface thereby allowing multiple and different nucleic acids to be amplified simultaneously on one array. Alternatively, a nucleic acid may be targeted to several different locations, each containing specific sets of amplification primers so that multiple different amplification reactions can be simultaneously carried out from a single sample. As noted above, the ability to remove unnecessary or unhybridized nucleic acids from the reaction mixture significantly aids this process.

A third advantage to this approach is that following the amplification reaction, the captured amplicons are available in a site-specific fashion for subsequent analyses, either by introduction of fluorescently labeled nucleotides or by the incorporation of labeled oligonucleotides during the course of the amplification reaction or by hybridization with an appropriate reporter oligonucleotide at the end of the reaction by denaturation of the amplicons that are bound to the capture sites.

In an example of this electronic addressing embodiment, an experimental protocol was designed to enhance anchored Factor V SDA sensitivity by using electronic hybridization of Factor V encoding template nucleic acid to anchored SDA primers (Seq. I.D. Nos. 20 and 21) on a microchip array. The SDA primers were biotinylated at their respective 5' ends. These primers also contained a BsoBI enzyme cleavage site. The reaction mix included the bumper primers (Seq. I.D. Nos. 22 and 23) for SDA. The microchip array was prepared by scraping the streptavidin-agarose layer from the outer electrodes of the microchip. The edges of the chip were waterproofed with Rain-X and the surface was buffed clean with a cotton swab applicator. The array was incubated with milli-Q water for at least 30 minutes at room temperature.

Solutions were prepared for electronic addressing on the microchip. SDA primers in 1 $\mu$M in 50 mM histidine buffer, 1 $\mu$M biotinylated T12-btr oligonucleotide in 50 mM histidine buffer, and 50 mM histidine wash buffer were prepared. The microchips were washed with 50 mM histidine buffer, and biotinylated T12-btr oligonucleotides were addressed using a standard A/C protocol (800 nAmps for 25 seconds) to selected capture sites to check the quality of the streptavidin microchips. The SDA primers were addressed to selected capture sites as shown using the standard A/C protocol.

For electronic hybridization (as opposed to passive hybridization) experiments, double stranded PCR nucleic acid templates were first denatured at 95° C., and an equal volume of 100 mM histidine buffer was added to the template. The template mixture was then electronically hybridized to the capture SDA primers using a standard A/C protocol for hybridization (1.6 $\mu$Amps, 60 seconds).

For passive hybridization experiments, asymmetric PCR nucleic acid templates were first denatured at 95° C. for 5 minutes. The solution was then brought to a 4xSSC concentration with a 20xSSC (3M NaCl, 0.3 M NaCitrate) stock and 20 $\mu$l of the mixture was pipetted onto a microchip (which had been previously electronically addressed with SDA primers) and incubated at room temperature overnight.

After incubation the microchip arrays were washed 2x with water and incubated with 1 mg/ml BSA for 30 minutes at room temperature to block any non-specific binding sites. The microchips were washed again with water (2x) and pre-warmed at 60° C. for 5 minutes. All SDA solutions were also pre-warmed at 60° C. for 5 minutes. After pre-warming, the water was removed from the microchips and incubated with 10 $\mu$l SDA reaction mix (40 mM $K_2HPO_4$ pH 7.6, 1.6 mM each dCTP$\alpha$S, dTTP, dATP and dGTP, 8.3 mM $MgCl_2$, 1.3 units BsoBI and 0.5 units Bst polymerase) for 30 minutes at 60° C. in a humidifying chamber. The reaction was stopped by removing the supernatant from the microchip surface to an eppendorf tube containing 2 $\mu$l of 100 mM EDTA.

After the SDA reaction, the microchips were washed 3x with 0.5xSSC, pH 7.2. The SDA products were then denatured on the microchip in situ with addition of 0.5xSSC, pH 12.0 for 4 minutes, washing the microchip with additional buffer after every minute. The microchips were then washed with 0.5xSSC, pH 7.2 at least 3 times, then with 4xSSC, pH 7.2 at least three times. The microchips were incubated with a 1 $\mu$M mix of btr-labeled reporter oligonucleotides (such as Seq. I.D. Nos. 24 or 44) in 4xSSC for 3 minutes at room temperature, washed extensively with 4xSSC at room temperature, then imaged.

Figure 7:
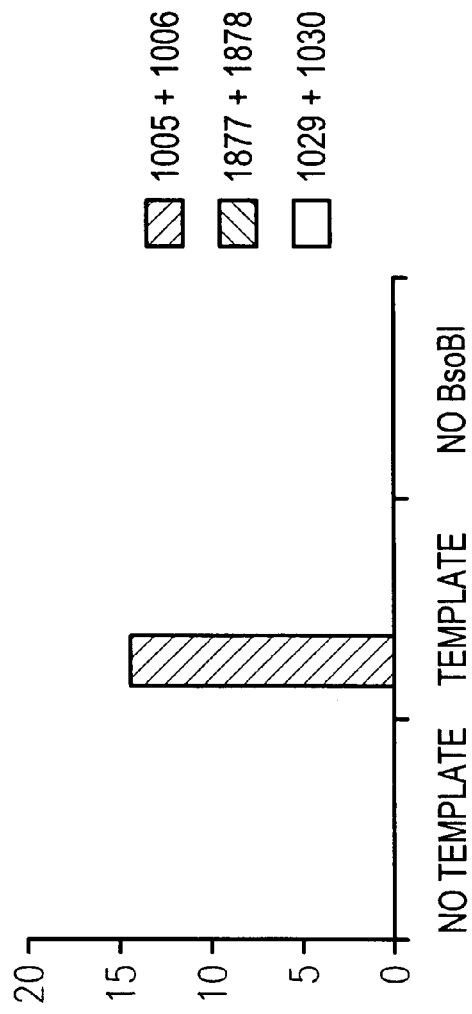
FIG. 7 shows the Mean Fluorescence Image of the fluoroscopic analysis of FIGS. 6A–6C.

For passive hybridization of Factor V template on microchips addressed with Factor V SDA primers at distinct sites, microchips were addressed with 1 $\mu$M of either Factor V SDA primers, or Factor V SDA primers lacking a BsoBI site as a negative control for the SDA reaction. Since the negative control lacks a BsoBI site, the reaction can only undergo primer extension upon binding of a template and not SDA amplification. This reaction controls for the presence of non-specific binding as well as the production of non-specific amplification products with which the reporter oligonucleotides may react. A no-template control was also present. These microchips were then fluoroscopically analyzed for Factor V amplicons having the fluoroscopically labeled btr-reporter oligonucleotides. SDA products were seen only in the microchip where SDA template was passively hybridized overnight (FIG. 6C). No products were seen in the no-template control microchip (FIG. 6A), or in the microchip (FIG. 6B) where BsoBI was not included into the reaction (another negative control for the SDA reaction). In the microchip that was passively hybridized (FIG. 6C), the SDA products are seen only in the area where the SDA primers were addressed, not in the non-cleavable SDA primer quadrant of the array, again confirming that the product detected is specific and is driven by an SDA-based process. The drawback of this assay is that the images seen after the SDA reaction were very weak, having MFI (Mean Fluorescence Image) values of 14 at an integration time of 1 s for non-diluted template levels (FIG. 7).

Figure 8:
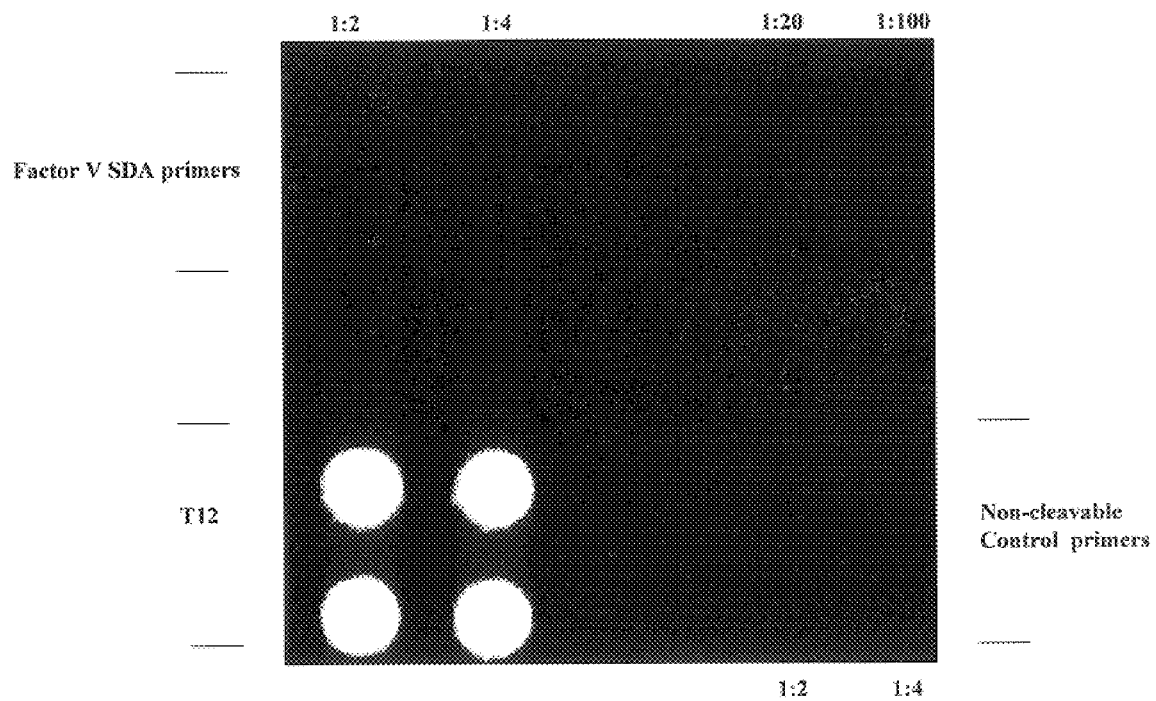
FIG. 8 shows a fluoroscopic analysis of a microchip where the SDA template was electronically targeted.
Figure 9:
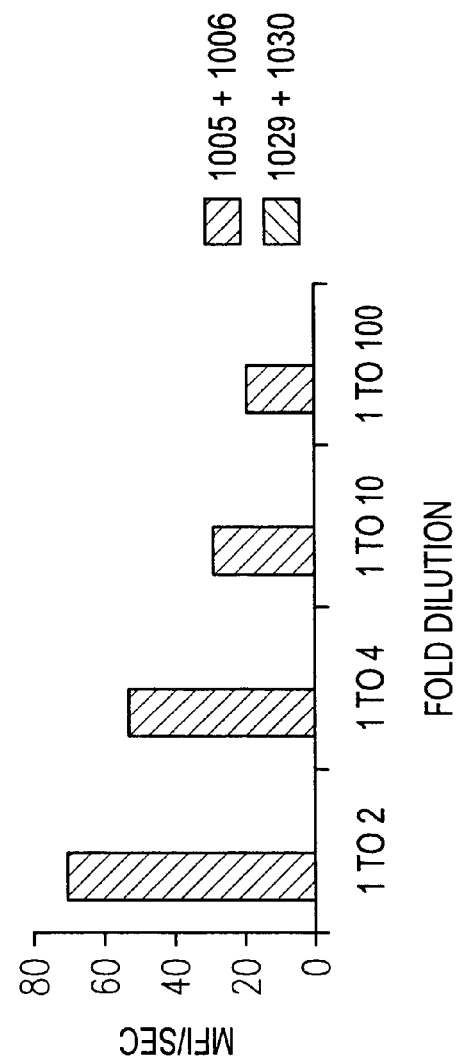
FIG. 9 shows the titration of Factor V PCR in the SDA template of FIG. 8.

For electronic hybridization of Factor V template to anchored SDA primers on a microchip, experiments were conducted in a manner parallel to that carried out for passive hybridization, with the exception that hybridization of the template was facilitated by electronic addressing. Additionally, the template was also serially diluted. As a control, passive hybridization of the factor V template was carried out and resulted in a very small increase (approximately 1 MFI unit) over background in the SDA reaction. Again, no signal was seen in the non-cleavable primer quadrant, indicating the need for SDA-directed amplification in this system. In contrast, the microchip that was electronically hybridized showed a signal in the SDA primer quadrant (FIG. 8) and showed a significant signal in all dilutions tested (FIG. 9). Even at a dilution of 1:100 of the Factor V template, the signal was still very high, at approximately 19.4 MFI/sec. Given that the MFI signal of a 1:100 dilution of the electronically addressable microchip was 19.4 times higher than the signal from a passively hybridized chip in this experiment, (and 1.4 times higher than in the passive hybridization experiment, above, where the template was not diluted) the efficiency of the SDA assay increased approximately 140–1940 percent by using an electronic hybridization protocol. This demonstrates that electronic hybridization of the template to SDA primers anchored on the microchip increases the sensitivity of the assay approximately 1000 fold. In addition, the time required to perform the entire SDA experiment was reduced by one full working day (as compared to passive hybridization wherein the template needed to be incubated overnight to achieve efficient binding levels).

In another example, we show that electronic addressing of target molecules to capture sites facilitates the amplification of DNA or RNA target nucleic acids using the technique known as nucleic acid sequence-based amplification (NASBA). In this method three different enzymatic activities are used in a coordinated fashion with an isothermal method of amplification. In this electronically-mediated process, the simultaneous or multiplex amplification of different sequences is possible either by site specific targeting and amplification or by using multiple primer sets. Moreover, NASBA, as practiced in the invention, may use either anchored or solution-based primers in the amplification reaction. In either case, the reaction is enhanced using electronic addressing of the target to its respective amplification primers.

In this example, target nucleic acid sequences were first electronically hybridized to discrete locations upon a microchip. Unwanted or non-specifically binding nucleic acids were removed either by electronic washing, or passive (non-electronic) washing or by a combination of the two. Following the wash step, the hybridization solution was replaced by a buffer cocktail comprising amplification primers, nucleotides, magnesium chloride and the enzymes or enzymatic activities necessary for amplification. (These enzymatic activities are: reverse transcriptase activity; RNase H activity; and RNA polymerase activity. The activities of these enzymes coordinately serve to amplify the isolated sequences in a fashion similar to that of NASBA.) Once the amplification cycles were completed, the amplified material was electronically isolated or captured and then quantitated (i.e., detected) by various methods known in the art. In general, such detection may be carried out using, for example, a capture oligonucleotide specific for the newly synthesized region or, a fluorescently-labeled oligonucleotide in a "sandwich assay."

Each stage of this process is augmented as compared to existing technology. For instance, the electronic targeting of the target sequence followed by its specific hybridization using suitable capture oligos (e.g. the primers for amplification) allows for the electronic removal of unwanted or contaminating DNA or RNA. The removal of nonspecific nucleotides that can cause non-specific binding and amplification, allows for a higher complexity of amplification events to simultaneously occur, as well as for more specific amplification. In addition, if all the primers for amplification are anchored, amplification events using different target sequences can occur simultaneously at different locations upon the chip or device, i.e. multiplex reactions. The enzymes themselves can also be targeted, allowing for greater precision in mediating the amplification events or stages. Finally, the products of the amplification reaction can also be targeted to alternative sites and quantified, allowing the progress of the amplification reaction to be followed.

In one representative, but not limiting experiment, NASBA amplification of an HTLV1 plasmid was performed in solution using three different concentrations of template plasmid (approximately 1 ng, 1 pg, and 1 fg). The reaction employed an initial melting of the DNA template at 95° C., followed by an isothermal annealing step of 15 minutes at 50° C. The annealing reaction consisted of 8 $\mu$l of 2.5× NASBA mix (100 $\mu$L of 25 mM NTP mix, Pharmacia Lot #60920250111; 50 $\mu$L of 25 mM dNTP mix, Pharmacia Lot #6092035011; 50 $\mu$L of 1 M Tris, pH 8.5; 31.25 $\mu$L of 2M KCl; 15 $\mu$L of 1M MgCl$_2$; and 253.75 $\mu$L sterile H$_2$O), 1 $\mu$l of a 5 $\mu$M concentration of an oligonucleotide primer (#885; 5' AATTCTAA TACGACTCAC TATAGGGAGA GGT-GATCTGA TGTCTGGAC AGG 3' (SEQ ID NO. 16), and 1 $\mu$l of one of the three dilutions of the HTLV1 plasmid (or none) in four separate tubes to achieve 1 ng, 1 pg, 1 fg, and 0 final concentrations. Enzymes which would not survive the 95° C. denaturation step were added at the beginning of the amplification step. Thus, 1 $\mu$L of 100 mM DTT (dithiothreitol) and then 0.5 $\mu$L AMVRT (AMV reverse transcriptase from Boehringer Mannheim (Cat No. 1495 062; Lot No. 83724624-76) were added at the 50° C. step. The reaction was terminated by heating to 95° C. for 5 minutes. The tubes were placed on ice.

Following the annealing reaction, an amplification reaction was set up, also in four tubes, consisting of 10 $\mu$L 2.5×NASBA mix; 1 $\mu$L of 250 mM DTT; 0.3 $\mu$L of Rnase H (Ribonuclease H from Boerhinger Mannheim, Cat No. 786 349; Lot No. 13656445-05); 2.5 $\mu$L enzyme mix (20 u T7 polymerase from Boerhinger Mannheim Lot # 83495822-31; 8 u AMV RT; 0.2 u RNase H; and 2.5 $\mu$g Rnase and Dnase free BSA (Bovine Serum Albumin) from Pharmacia # 6078914011); 6 $\mu$L of primer mix (5 $\mu$L of 5 $\mu$M primer #885; 5 $\mu$L of 5 $\mu$M primer #882: ACTTCCCAGGGTTTG-GACAGAGT (SEQ ID NO. 17); 18.75 $\mu$L 100% DMSO; and 1.25 $\mu$L H$_2$O); and 2 $\mu$L of primed DNA from the four annealing reaction tubes, each placed in a separate tube. The reaction was incubated for 60 minutes at 40° C., then put on ice. The reactions (10 $\mu$L) were than separated on a 2% agarose gel and stained with ethidium bromide.

Figure 10A:
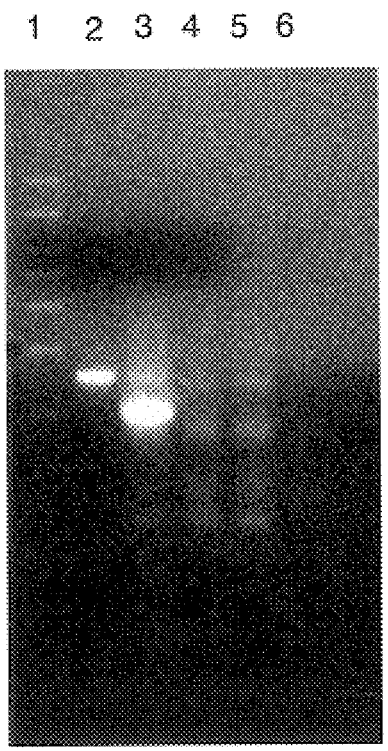
FIG. 10(a) shows the gel product of a NASBA amplification.
Figure 10B:
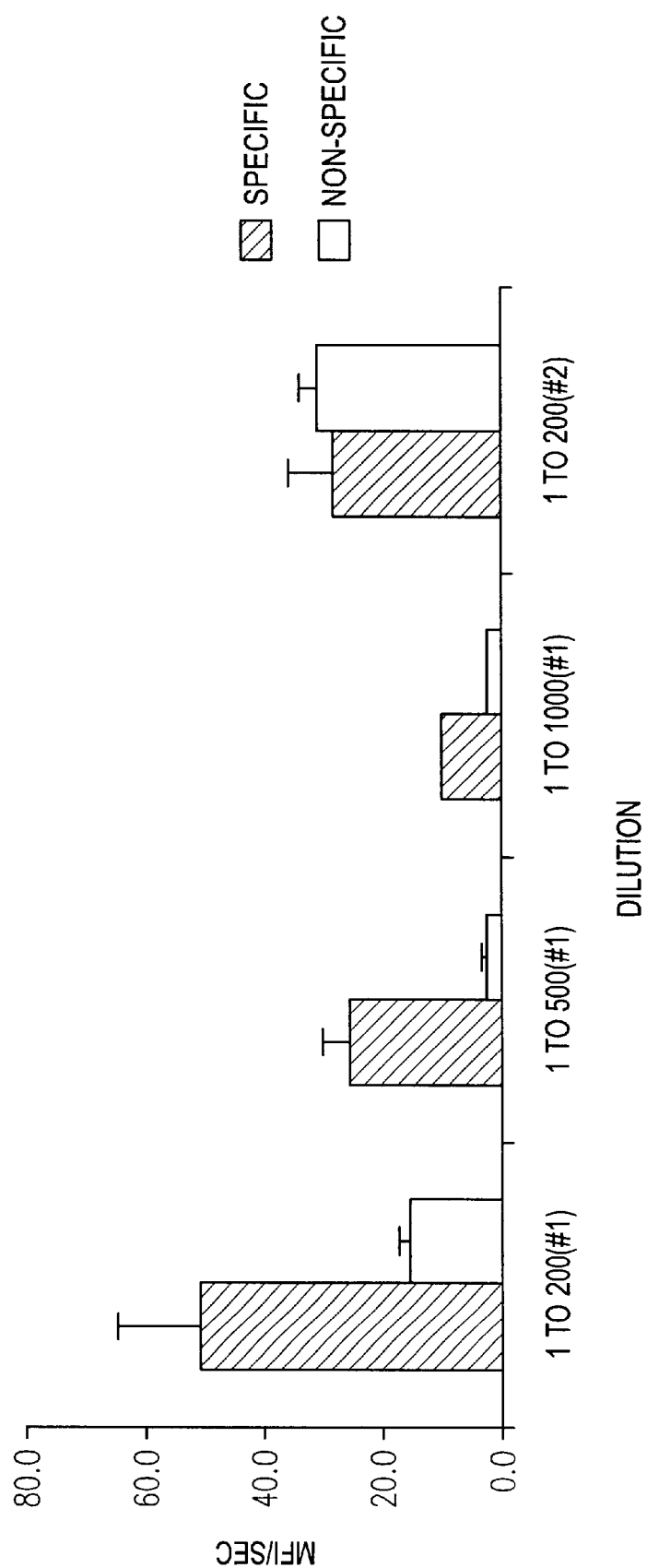
FIG. 10(b) shows fluoroscopic analysis of a sandwich assay result of NASBA Tax plasmid after electronic targeting to a microarray.

The highest concentration of starting template plasmid produced the largest amount of product, whereas the lower two concentrations produced little or no product (FIG. 10a). The product of the 1 ng reaction (the bright band on the gel) was cut out of the gel and then diluted either 200-fold, 500-fold or 1000-fold in 50 mM histidine. The reaction product of the 1 pg template reaction was also diluted 200-fold for comparison. These reaction product dilutions were then electronically targeted to capture sites upon a microarray containing either specific (500 $\mu$M of XL5R.bio, 5' TTCTTTTCGGATACCCAGTCTACGTGTTTG 3' (SEQ ID NO. 18) or non-specific (ATA5.bio) pre-targeted capture antibodies using 500 $\mu$A constant current for 1 minute, changing the buffer and targeting the next capture site without washing. After targeting the reaction products, the capture sites were washed 5×with histidine (50 mM) and the fluorescence at each location evaluated (FIG. 10b) using a fluorescently labeled reporter oligo (HTVPXs.313TR; (NH2)-ACTTCCCAGGGTTTGGACAGAGT 3' (SEQ ID NO. 19) 15 $\mu$L) introduced, passively, for 15 minutes at 25° C. Following 3 washes in 1 mL of 0.2×STE/1% SDS, and 5 additional minutes in STE/SDS, the capture sites were rinsed, and a 2 second image was taken. Thereafter, the buffer was changed to histidine and the capture sites were run by column at 200 $\mu$A/pad for 1 minute, washed, and a 2 second image taken. The results of the electronic sandwich assay of the amplified reaction paralleled the relative amounts of amplified product introduced, as shown in FIG. 10b.

EXAMPLE 3

In yet another example, anchored SDA is carried out, preferably using electronic targeting of the target nucleic acid to the specific site, and preferably including at specific sites upon the array non-cleavable oligonucleotides in combination with a greater ratio of normal SDA primers (i. e. the non-cleavable primers do not contain the requisite restriction endonuclease site necessary for SDA, but which are identical to SDA primers in other aspects). Anchored SDA is then carried out, using electronic targeting of template nucleic acid to the specific site followed by amplification and reporter hybridization. The optimal ratio of non-cleavable to normal primers is determined empirically, and is based on the signal obtained from reporter labels. Alternatively, other sites and/or functionalities can be introduced upon these non-amplifying primers for the purposes of subsequent cleavage and analysis or other manipulations. The prime criteria of these non-cleavable primers is that the 3' terminus contains sufficient homology to the target nucleic acid or amplified products thereof to hybridize and serve as the basis for primer extension by polymerase.

In a specific experiment of this example, different proportions of standard Factor V amplifying primers were mixed with primers which no longer had a BsoBI site present. These mixtures were targeted to different locations upon the array and diluted Factor V PCR amplicons were targeted to each location. The entire array was then washed and a mixture containing SDA amplification reaction components (except amplifying primers) was added. The amplification reaction was allowed to proceed for 30 minutes at 60° C. then, following denaturation, Bodipy-Texas Red labeled reporter probes were added and hybridized. The fluorescence present at each site was then quantified.

The experimental protocol followed in this experiment was as follows. First, microchips were prepared for electronic addressing and hybridization by scraping any agarose away from the outer electrodes and treating each microchip surface with Rain-X. The chips were washed three times with water and allowed to stand in water for at least about 30 minutes. Then Factor V SDA primers (i.e., Seq. I.D. Nos. 20 and 21) and non-cleavable (NC) primers (i.e., Seq. I.D. Nos. 42 and 43) were diluted to 2 µM total (from 0–100% non-cleavable primers mixed with SDA primers, see Table III below) and equal volumes of 100 mM histidine were added to make a 1 µM primer solution in 50 mM histidine buffer. Next 10 nM btr-T12 and 1 µM ATA-5 oligos were prepared as controls in 50 mM histidine. Factor V template DNA was then diluted to an appropriate concentration and incubated at 95.5° C. for about 5 minutes. An equal volume of 100 mM histidine was added to make a final concentration of 50 mM histidine buffer.

TABLE III

Non-Cleavable Primers to SDA Primers Mix

| % Non-Cleavable Primers | 2 µM NC Primers (µl) | 2 µM SDA Primers (µl) |
|---|---|---|
| 0 | 0 | 100 |
| 10 | 10 | 90 |
| 20 | 20 | 80 |
| 30 | 30 | 70 |
| 40 | 40 | 60 |
| 50 | 50 | 50 |
| 60 | 60 | 40 |
| 70 | 70 | 30 |
| 80 | 80 | 20 |
| 90 | 90 | 10 |
| 100 | 100 | 0 |

The SDA/Non-Cleavable primers mix, as well as controls, were then electronically addressed and a template was hybridized onto each microchip array. An image was taken and the microchips were washed three times with water and incubated with 1 mg/ml BSA for 30 minutes at room temperature. The microchips were then washed two times with water and pre-incubated at 60° C. for 5 minutes in a humidifying chamber (i.e. a petri dish with moistened Whatman 3 MM paper).

An SDA mix comprising 40 mM $K_2HPO_4$, 1.6 mM dCTPαS, 1.6 mM dTTP, 1.6 mM dCTP, and 1.6 mM dGTP, 8.3 MM $MgCl_2$, 1.3 units BsoBI enzyme, and 0.5 units Bst polymerase, was pre-incubated at 60° C. for 5 minutes. Water was removed from the microchips and 10 µl of pre-warmed SDA mix was added to each microchip without allowing the microchips to cool down. The microchips were then incubated at 60° C. for 30 minutes. The SDA reaction was then stopped by removing the solution from each microchip and transferring it to an eppendorf tube containing 2 µl 100 mM EDTA. The supernatant was then analyzed on non-denaturing polyacryamide gels.

Figure 11:
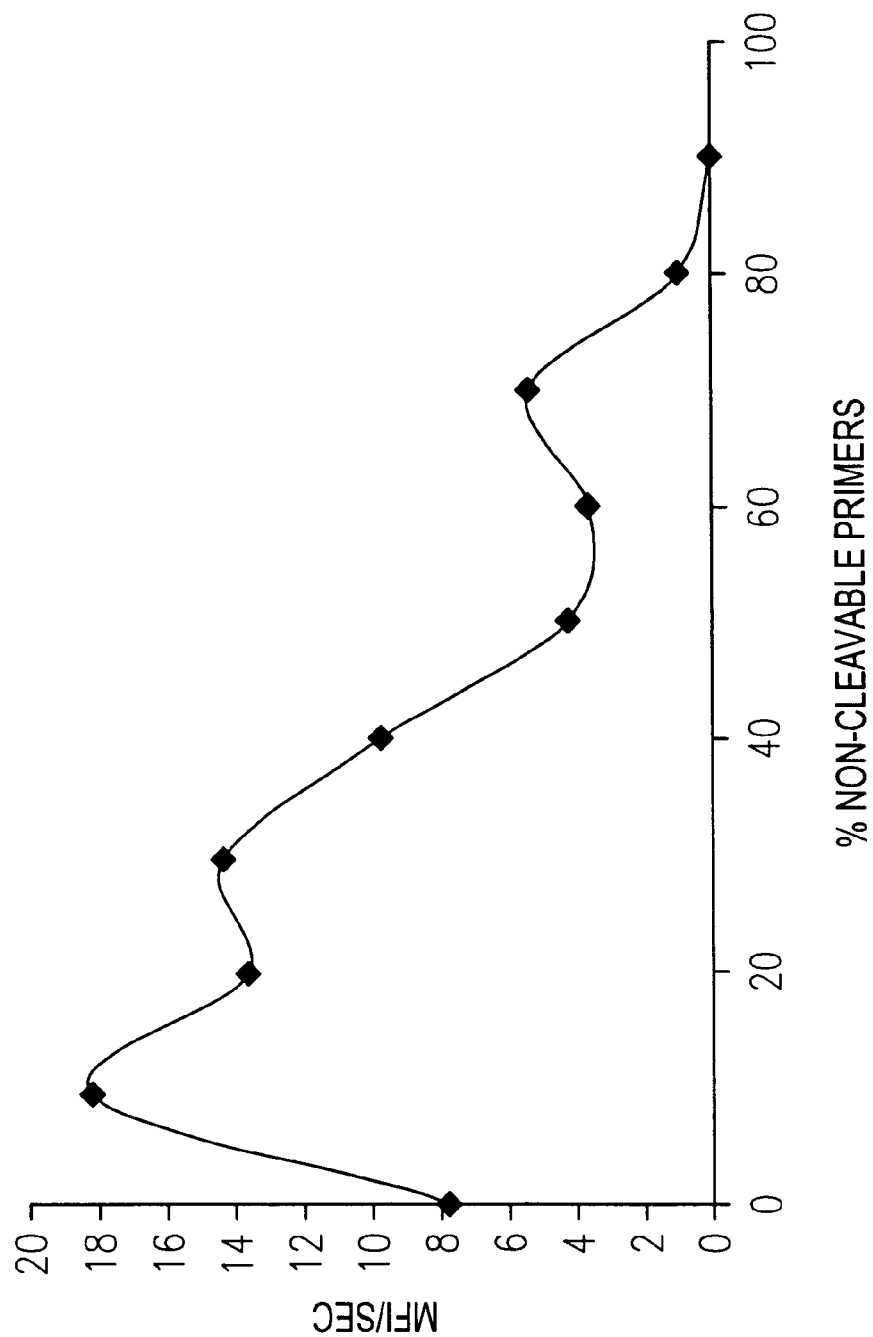
FIG. 11 shows a graph of the titration of non-cleavable SDA primers in Factor V anchored SDA.

The microchips were washed with 0.5×SSC solution, wherein the SSC solution comprises 75 mM NaCl and 7.5 mM NaCitrate, pH 7.2, at least three times. Next, the microchips were incubated in 0.5×SSC, pH 12 solution for 4 minutes, with the solution being pipetted up and down about every minute. Each microchip was washed at least three times with 0.5×SSC, pH 7.2, then three times again with 4×SSC solution. Passive hybridization of 1 µM reporter oligonucleotides in 4×SSC was then carried out at room temperature for 3 minutes. Each microchip was washed extensively with 4×SSC. If necessary, an additional stringent wash with 0.2×SSC/1% SDS was done for 5 minutes at room temperature. The microchips were then washed extensively with 0.2×SSC. Finally, the microchips were imaged with appropriate lasers and filters, and the fluorescence present at each site was quantified. Results from this experiment are shown in FIG. 11. As shown in FIG. 11, a 10% optimal percentage of non-cleavable SDA primers included in the SDA primer mix for anchored SDA gave an approximately 2-fold increase in specific signal over the absence of non-cleavable primers (0%). As expected, with an increase in non-cleavable to SDA primer ratios, the efficiency of the SDA reaction decreases to levels where no detectable SDA amplification can be seen. This demonstrates that the addition of non-cleavable primers to the SDA primer mix, which in effect retains any signal that may have been nicked prior to denaturation of the double-stranded template, improves signal intensity in anchored SDA.

EXAMPLE 4

In another embodiment, an amplification method of the present invention comprises an allele-specific SDA method. The method preferably selectively amplifies only those strands that include a specific allele. The method preferably utilizes amplifying primers designed so that their respective 3' termini include nucleotide bases that are complementary to the nucleotide sequence of the desired allele. At least one of the primers may also preferably include a biotin moiety on its 5' end to provide a facile mechanism for capturing amplicons on the array following electronic targeting and amplification. Generally, the specificity of the process of this example is derived from the low efficiency of nucleic acid chain extension when the 3' terminal nucleotide of the primer is non-complementary to the target sequence.

In a modification of this example, individual amplified patient nucleic acid samples are immobilized in discrete locations on the microarray, and all samples are probed simultaneously with gene or allele-specific reporter probes.

Individual patient samples are immobilized by introducing biotin into the samples during SDA. One of the SDA primers is added which contains a 5' biotin linker which does not have a restriction cleavage site, and, therefore, is not cleavable. The samples are denatured and addressed to individual capture sites. A single stranded amplicon from each patient is immobilized at an individual capture site. Once all patient samples are immobilized, they are all probed simultaneously and in parallel. Thus, an open microchip is used to analyze multiple patient samples with minimal cross-contamination.

In this example, the biotinylated primer is preferably either a noncleavable version of the flanking primer used for amplification, or an internal sequence. In either case, it forms a dead end product (i.e. one which is not further amplified). The primer is preferably present in limited amounts so that the entire primer is converted to product. For instance, when screening for a genetic mutation such as, for example, the Factor V Leiden mutation, there are only two alleles, a wild type and a mutant. Amplification is performed using primers which are specific for the wild type locus, but not the allele (i.e., mutant). The internal biotinylated primer is converted to a product shorter than the full length amplicon through extension if the allele is present. The fragment is then addressed to a pad and subsequently probed with an allele-specific probe, or an allele-specific biotinylated internal probe is used. Amplification may take place in the presence of fluorescently labeled nucleotides. Preferably, each patient sample is amplified in two separate reactions with allele-specific primers (for wild and mutant alleles) which are then addressed to different pads, or the two reactions are performed simultaneously using reporter molecules that fluoresce in two different colors and both products are addressed to the same capture site (in which case genotype would be determined by the fluorophore remaining at the site for that patient).

(See Example 1 B for additional embodiments of allele-specific methodology and technique).

EXAMPLE 5

In another embodiment, SDA products may be simultaneously generated and specifically captured on a microchip by performing thermophilic SDA (tSDA) in a flow cell region over the microchip of the present invention. (see U.S. Pat. No. 5,648,211 for a discussion on tSDA and U.S. Pat. No. 5,547,861 for a discussion on signal primer extension, both herein incorporated by reference). By tSDA is meant SDA using thermophilic enzymes allowing operation at temperatures in excess of 40° C. to facilitate stringent hybridization. Prior to amplification an internal capture sequence having a 5' biotin modification is immobilized preferably to a specific streptavidin-containing capture site location. As single stranded amplicons are generated free in solution during the SDA process, a fraction of the amplicons specifically hybridize to the immobilized capture oligonucleotide. Detection of the hybridized strand is preferably via one of the methods described throughout this disclosure. This embodiment of the method allows use of very small sample volumes (e.g., on the order of about 10 μl), and allows for specificity controls due to use of sequences for capturing that are preferably located on separate capture sites and are internal to the sequences used to perform SDA priming. Moreover, detection of the captured sequences may occur in "real time" as they are being generated during the SDA reaction thereby facilitating the simultaneous SDA and monitoring of the SDA reaction and generated amplicons.

Figure 5A:
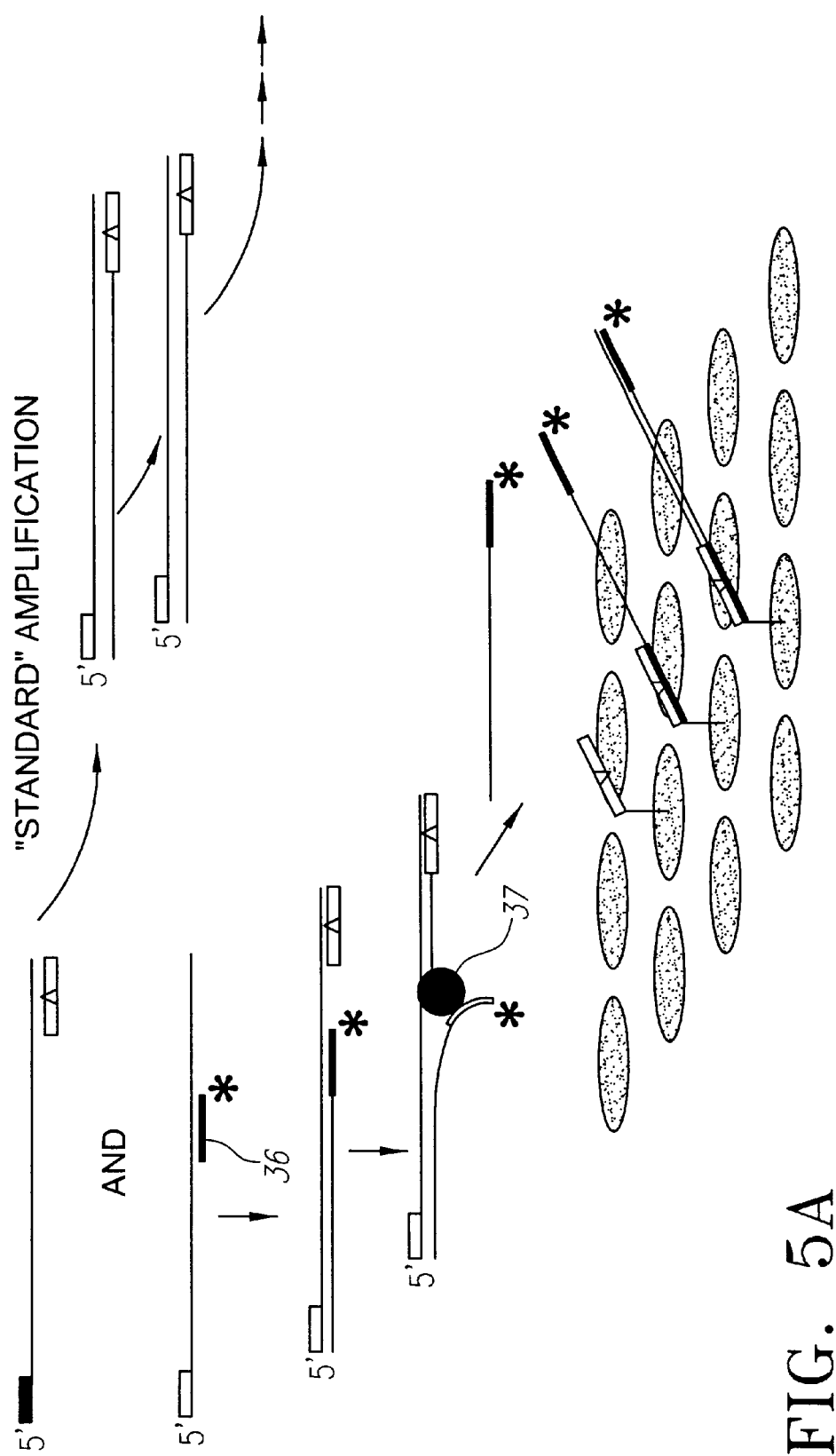
FIG. 5A shows a diagram of a first scheme of incorporating a fluorescent species in an amplification reaction for detection purposes.

With respect to this method there are two exemplary schemes to incorporate a fluorescent species for detection. In a first scheme to incorporate a fluorescent species for detection, as is shown in FIG. 5A, an additional oligonucleotide 36 is included in the amplification reaction. This additional oligonucleotide is fluorescently labeled and binds to its single stranded complemer generated by the amplification process. Upon binding, polymerization is initiated in a 5' to 3' direction from this primer by the polymerase 37 used in the SDA reaction. As a course of the regular amplification process, an oligonucleotide which functions as an amplifying primer binds 5' upstream to the same strand as the fluorescently labeled species. As polymerase extension occurs from this primer, the fluorescently labeled strand is displaced and released as a single stranded species free into solution above the array. On the array are previously addressed anchored complementary oligonucleotides. These serve to capture a portion of the fluorescently labeled oligonucleotides and provide a fluorescent signal upon the array which is both location-specific (and, therefore, sequence specific) and increasing over the course of the reaction.

Figure 5B:
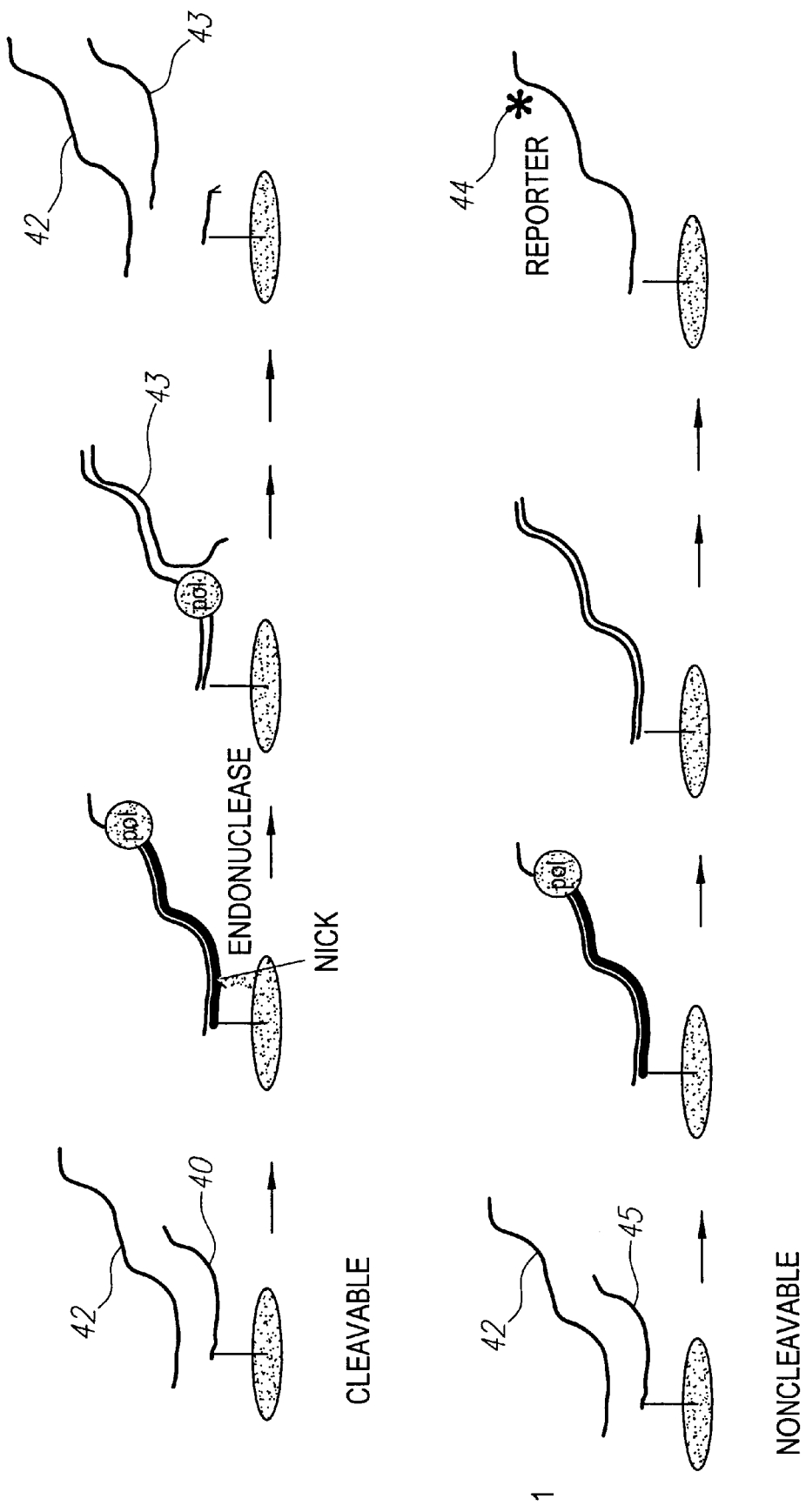
FIG. 5B shows a diagram of a second scheme of incorporating a fluorescent species in an amplification reaction for detection purposes.

In a second scheme to incorporate a fluorescent species for detection, as is shown in FIG. 5B, anchored capture oligonucleotides have either an unmodified endonuclease restriction sequence and capable of supporting an SDA reaction 40 or a modified sequence that will not be recognized by an endonuclease 45. These anchored capture primers 40 and 45 are used to bind single stranded products 42 of the amplification reaction. These capture oligonucleotides 40 and 45 serve as the site for oligonucleotide extension by polymerase activity. Upon completion of the amplification reaction, the double stranded material is melted, preferably by electronic or chemical methods (including, for example, alkaline in pH 12), releasing the original amplicon 42 and extension product 43. The array is washed and then a fluorescently labeled oligonucleotide 44 is introduced. These reporter oligonucleotides specifically hybridize only to the polymerase extended portions of the capture oligonucleotides 40 and 45. In this scheme it is preferred that the ratio of cleavable to noncleavable oligonucleotides is about 10:1. It is believed that this ratio allows the amplification reaction to optimally proceed while providing a sufficient number of uncleaved extension products remaining at the capture sites for detection by reporter probe.

EXAMPLE 6

In still another embodiment of the invention, SDA is preferably conducted directly on an electronically addressable microchip under the following conditions. The sample is initially prepared and randomly sheared to less than about 5 kB. The sample is then denatured and target nucleic acid is captured to a single capture site that contains both 5' and 3' SDA primers. "Bumper primers" which hybridize to the regions immediately upstream of the capture primers are added in a relative concentration of about 1/10 that of the capture oligonucleotides. An SDA mix (i.e. 3 unmodified dNTPs, 1 thiol modified NTP, (and, possibly, a fluorescent labeled NTP,) and enzymes preferably comprising thermophilic exo (−) DNA polymerase plus restriction enzyme) are passively added. The microchip is then heated to about 40–60° C. and SDA is allowed to proceed.

"Real time" detection of the SDA reaction and product amplicons is possible by incorporating NTPs which allow fluorescent energy exchange or quenching. For example, an NTP containing Bodipy Texas red is combined with one that contains Cy5. Incorporation of NTP via polymerase elongation can be continuously monitored by monitoring fluorescent energy shift.

Under one theory it is believed that the preferred minimum estimated spacing between adjacent oligonucleotides on a pad is about 1.25 nm ($10^4$ODNs/80 $\mu$m$^2$=100×$10^6$/80×$(10^3)^2$ nm$^2$=1.25 ODN/nm$^2$). If oligonucleotide bridging is required to start SDA, then it is believed that the optimal length of an SDA fragment which will allow optimal amplification can be determined empirically. As a starting point, 100 bp=34 nm seems reasonable.

EXAMPLE 7

In this embodiment, a novel method of an anchored SDA reaction which alters the spatial relationships between amplification primers, target DNA, and enzyme molecules is provided. Because both amplification primers are brought into close proximity to one another, the efficiency of the SDA reaction is actually increased. The spacing relationship between the amplification primers may also be adjustable by altering linker elements between the primers thereby enabling precise definition of the stoichiometry ratios of the primers, the local concentration of the primers, site directed template capture, and spatial relationships of the primers, so as to set up the SDA mechanism in a coupled-concerted fashion to benefit exponential amplification of target DNA.

Figure 12:
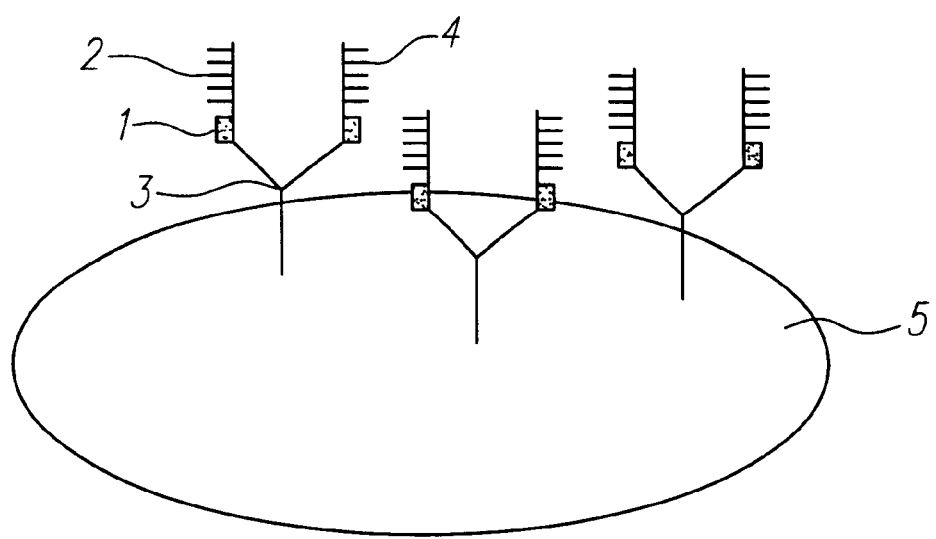
FIG. 12 is a schematic diagram of the anchored primers showing aspects of the branched primer design.
Figure 15:
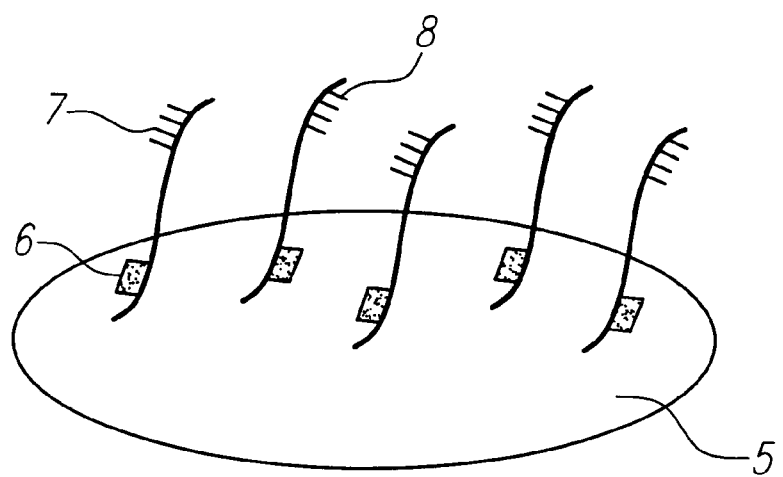
FIG. 15 is a schematic diagram showing anchored non-branched SDA target primers.

Referring now to FIGS. 12 or 15, SDA target capture primers are attached to specific areas or capture sites 5 on an electronically addressable microchip. The capture primers are attached at each site such that both upstream and downstream primer pairs required for SDA specific for a target nucleic acid of interest are present together in close proximity to one another at the capture site. With regard to FIG. 12, branched structure 3 is attached to capture site 5 and to the 5' ends of plus and minus strand SDA nucleic acid primers. For each primer, an unmodified restriction site sequence 1 (i.e., the unmodified strand of a hemimodified restriction site) is located 5' to target specific capture sequences 2 and 4. With regard to FIG. 15, linear plus and minus strand nucleic acid SDA primers are attached to capture site 5 at their respective 5' ends. Like the branched primer pairs, the linear SDA primers comprise unmodified restriction site 6 sequence 5' to target specific capture sequences 7 and 8.

The microchip may be prepared according to teachings known in the art such as the method disclosed in U.S. Pat. No. 5,605,662 herein incorporated by reference. In the current example, prior to addition of SDA primers, the streptavidin-agarose layer was scraped from the outer electrodes of the microchips. The edges of each microchip were waterproofed with Rain-X (Unelko Corporation, Scottsdale, Ariz.) and the surface of the microchip buffed and cleaned with a cotton swab applicator. The microchips were incubated with milli-Q water for about 30 minutes at room temperature before use.

The microchips were then washed with 50 mM histidine buffer and biotinylated oligonucleotides (e.g., oligo dT12-btr) having a fluorophore in 50 mM histidine buffer were addressed to the capture sites using a standard A/C protocol (800 nAmps for 25 seconds) to check the quality of the streptavidin microchips. The btr fluorophore was imaged using the appropriate excitation and emission filters for btr. The SDA primers (Seq. I.D. Nos. 20 and 21) were addressed to selected capture sites using the same standard A/C protocol.

Figure 13:
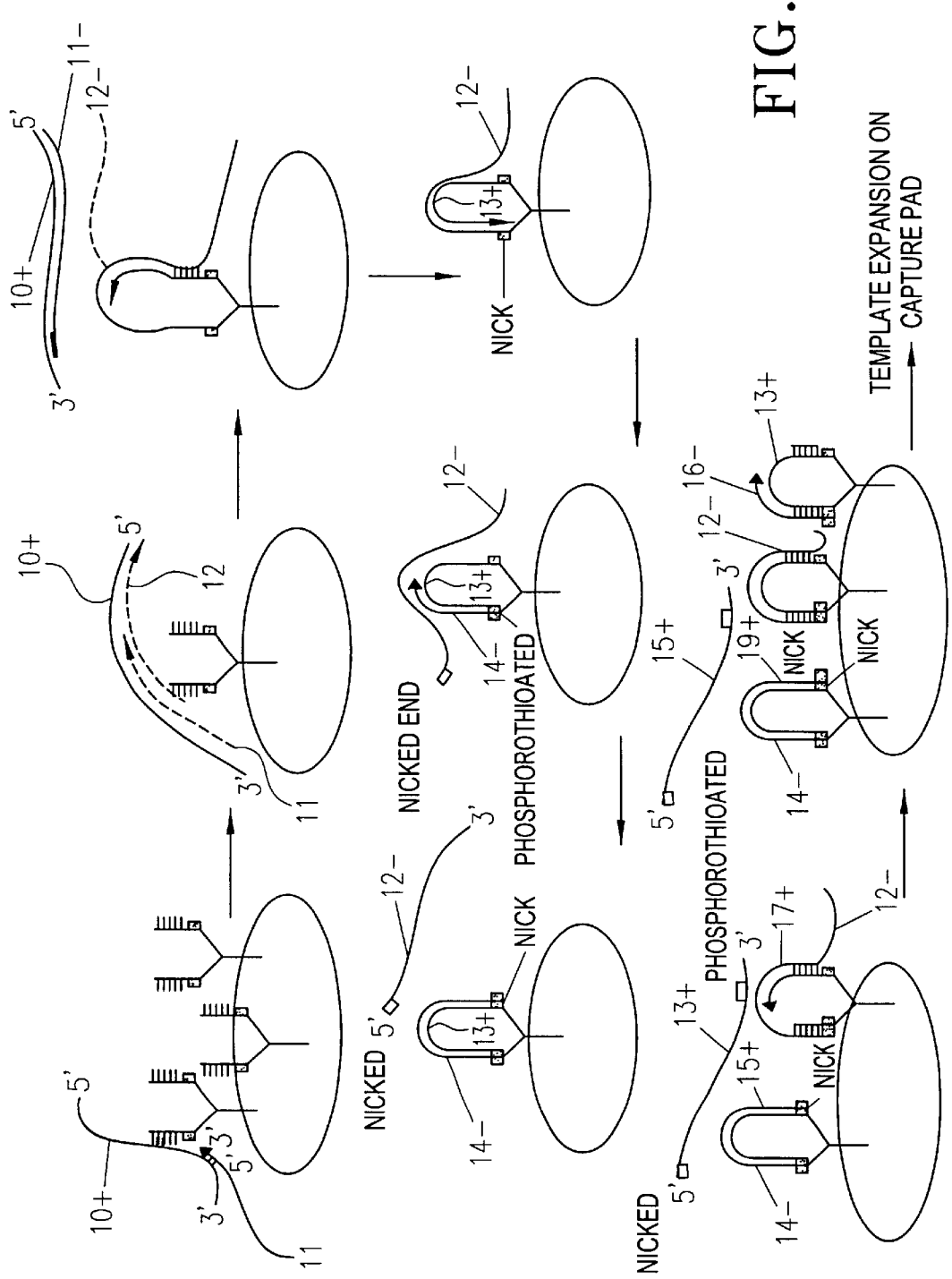
FIG. 13 is a schematic diagram showing the stepwise process of creating amplicons from target nucleic acid sequence at a branched primer pair site.

As shown in FIG. 13, SDA is carried out at capture sites. Following denaturation of the double stranded target species, single stranded target molecules (e.g., a plus strand 10+ shown in FIG. 13) are first addressed to the capture sites. For electronic hybridization of the various templates, double stranded DNA target sequence was first denatured at 95° C. and mixed with an equal volume of 100 mM histidine buffer. The template mixture was then electronically hybridized to the capture SDA primers using a standard A/C protocol for hybridization (1.6 $\mu$Amps for 60 seconds). After hybridization of the template mixture, the microchips were washed twice with water and incubated with 1 mg/ml BSA for 30 minutes at room temperature to block any non-specific binding sites. The microchips were washed again with water twice and pre-warmed at 60° C. for 5 minutes. All SDA solutions were also pre-warmed at 60° C. for 5 minutes. After pre-warming, the water was removed and the microchips were incubated with 10 $\mu$l SDA reaction mixture (40 mM K$_2$HPO$_4$ pH 7.6, 1.6 mM each dCTP$\alpha$S, dTTP, dATP, and dGTP, 8.3 mM MgCl$_2$, 1.3 units BsoBI and 0.5 units Bst polymerase) for 30 minutes at 60° C. in a humidifying chamber. The reaction was stopped by removing the supernatant from the microchip surface to an eppendorf tube with 2 $\mu$l of 100 mM EDTA.

As indicated in FIG. 13, strand extension of the target nucleic acid of both plus and minus strands undergo strand displacement to form plus and minus single stranded amplicons (e.g., 12− and 13+). The plus and minus strand amplicons may each be electronically hybridized to adjacent or nearby unused primer pair sets.

In the instant example, following the SDA reaction, the microchips were washed three times with 0.5×SSC, pH 7.2. The SDA products were then denatured on the microchip in situ with addition of 0.5×SSC, pH 12.0 for 4 minutes in which the microchips were washed with fresh buffer every minute. The microchips were then washed with 0.5×SSC, pH 7.2 at least 3 times, with 4×SSC, pH 7.2 about 3 times. The microchips were then incubated with a 1 $\mu$M mixture of btr-labeled reporter oligonucleotides in 4×SSC for 3 minutes at room temperature followed by extensive washing with 4×SSC at room temperature, then imaged with the appropriate laser and excitation/emission filters.

Although for simplicity in showing the efficiency of anchored SDA, this example carries out detection of SDA products following amplification, detection may be carried out during amplification using labeled target specific probes that are blocked at their respective 3' ends such as by incorporating a 3' phosphate group rather than a 3' OH on the terminus of the probe. Such labeled probes may further comprise single stranded nucleic acids which may be electronically addressed to the capture sites allowing detection of increasing signal as target and amplicon species are amplified at the capture pad site without the probe itself taking part in the SDA extension or amplification process.

In addition to the electronically controlled anchored SDA described above, two additional protocols were followed as controls wherein target nucleic acids were captured by passive hybridization followed by anchored SDA, and where SDA was carried out in solution. First, in the passive hybridization experiments, double stranded target nucleic acids were first denatured at 95° C. for 5 minutes. The solution was then brought to a 4×SSC concentration with a 20×SSC (3M NaCl, 0.3 M NaCitrate) stock and 20 ul of the mixture was pipetted onto the microchip (which had been previously electronically addressed with SDA primers) and incubated at room temperature overnight. Following the target hybridization to the primers, SDA experiments were carried out as described above.

Second, where SDA was carried out in solution, no microchips were used. The reason for this is that the purpose of conducting solution based SDA was to compare the capacity to amplify target species in a multiplex format in solution versus on a microchip. The solution based SDA experiments were carried out in eppendorf tubes in a total of 50 µl of SDA mix as described above.

In a first method of this example three different target nucleic acid species were amplified by SDA using primer pairs that were addressed to specific locations on an electronically addressable microchip. Ultra pure human placental DNA, Chlamydia genomic template and deoxynucleoside triphosphates were obtained from Becton Dickenson. Target templates for nucleic acids directed to detect the presence of gene sequence associated with hemochromatosis and Factor V were obtained using SDA bumper primers (Seq. I.D. Nos 22 and 23) and human placental DNA. PCR reaction conditions for amplifying such templates is well known to one of ordinary skill in the art of amplification. SDA capture primer pairs, bumpers, and signal probes for each test target species were synthesized and PAGE-purified by Oligos, Etc. (Oregon). The restriction site encoded into the primer sequences was BsoBI.

The following is a list of the various SDA primers and signal probes for each of the target species:
SDA primer biofacV10sSDA.213, (SEQ ID NO. 20) 5'[biot] ACCGCATCGAATGCATGTC-CTCGGGTCTCTGGGCTAATAGGA 3'
SDA primer biofacVaSDA.297, (SEQ ID NO. 21) 5'[biot] ACGATTCAGCTCCAGACTTCTCGGGTCA-GAATTTCTGAAAGG 3'
bumper primer facV10s.179, (SEQ ID NO. 22) 5' ACTA-CAGTGACGTGGACATC 3'
bumper primer facV10a.-127 (SEQ ID NO. 23) 5' TGTTAT-CACACTGGTGCTAA 3'
Signal probe facV10a.276 (SEQ ID NO. 24) 5' [BTR] CTGTATTCCTCGCCTGTC 3'
SDA primer chlaAL1.4811, (SEQ ID NO. 25) 5' [biot] CACGTAGTCAATGCATGTCCTCGGGTA-CAACATCAACACCTG 3'
SDA primer chlaAR1.4858, (SEQ ID NO. 26) 5' [biot] ACGATTCAGCTCCAGACTTCTCGGGT-GAGACTGTTAAAGATA 3'
bumper primer chlaBL1, (SEQ ID NO. 27) 5' CAG-CAAATAATCCTTGG 3'
bumper primer chlaBR1, (SEQ ID NO. 28) 5' CATTGGT-TGATGGATTATT 3'
Signal probe chlaDIL.4826, (SEQ ID NO. 29) 5' [BTR] GTCGCAGCCAAAATG 3'
Signal probe chlaCP2.4841, (SEQ ID NO. 30) 5' [BTR] TTCCATCAGAAGCTGT 3'
SDA primer haemsdas.6679, (SEQ ID NO. 31) 5' [biot] CACGTAGTCAATGCATGTCCTCGGG-TATAACCTTGGCTGTAC 3'
SDA primer haemsdaa.6773, (SEQ ID NO. 32) 5' [biot] ACGATTCAGCTCCAGACTTCTCGGGT-GCTCTCATCAGTCACA 3'
bumper primer haempcrs.6596, (SEQ ID NO. 33) 5' TGAAGGATAAGCAGCCAAT 3'
bumper primer haempcra.6773, (SEQ ID NO. 34) 5' CTC-CTCTCAACCCCCAATA 3'
Signal probe haemreps.6712, (SEQ ID NO. 35) 5' [BTR] AGATATACGTGCCAGGTG 3'
Signal probe haemreps.6733, (SEQ ID NO. 36) 5' [BTR] CTGATCCAGGCCTGGGTG 3'

Figure 16:
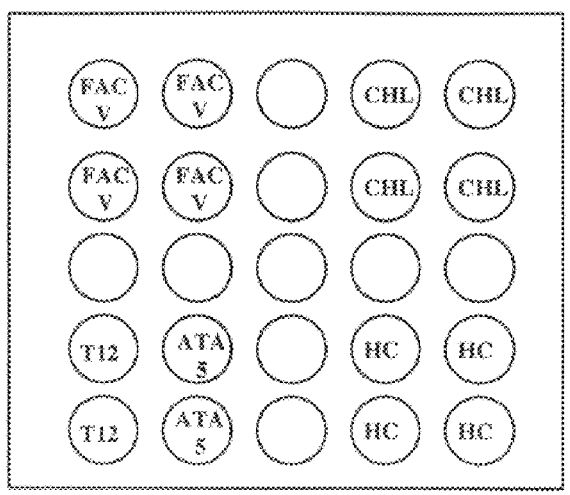
FIG. 16 is a diagram showing the layout of a microchip pad with the locations on the pad to which the various target species tested have been addressed as explained in Example 7.

As depicted in FIG. 16, biotinylated SDA primers for Factor V (FAC V), Chlamydia (CHL) and Hemochromatosis (HC) were anchored onto streptavidin-containing microchips and a mixture of Factor V, Chlamydia and Hemochromatosis templates were hybridized onto the primers electronically. Control template T12 was also anchored.

Figure 17:
FIG. 17 is a photographic image of a control SDA reaction wherein no target nucleic acid was present.
Figure 18:
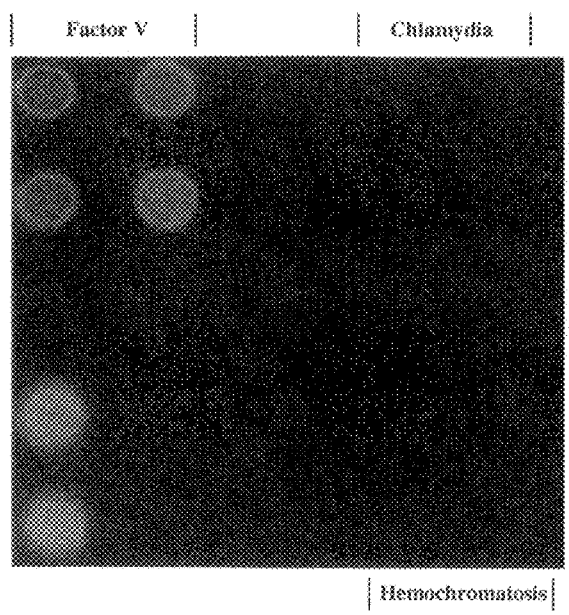
FIG. 18 is a photographic image showing specific localization of SDA amplified Factor V target in the presence of multiple target species on only SDA capture primer pairs specific for Factor V which had been previously addressed to only the four capture sites.
Figure 19:
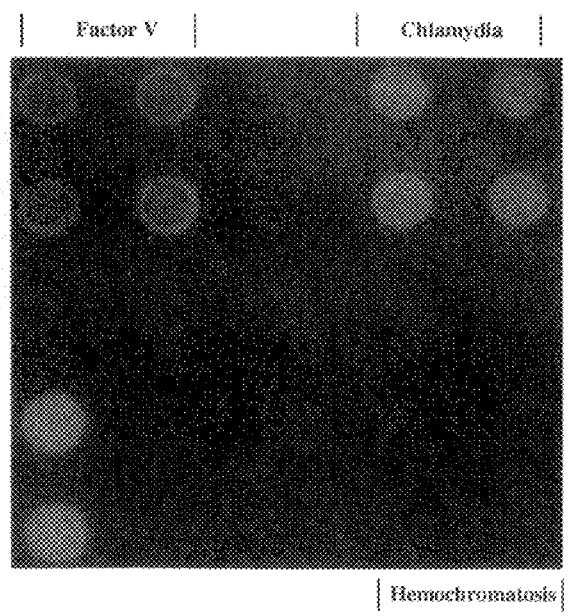
FIG. 19 is a photographic image showing specific localization of SDA amplified Factor V and Chlamydia targets which were amplified in the presence of multiple target species and SDA capture primer pairs specific for Factor V and Chlamydia that had been previously addressed to specific capture sites.
Figure 20:
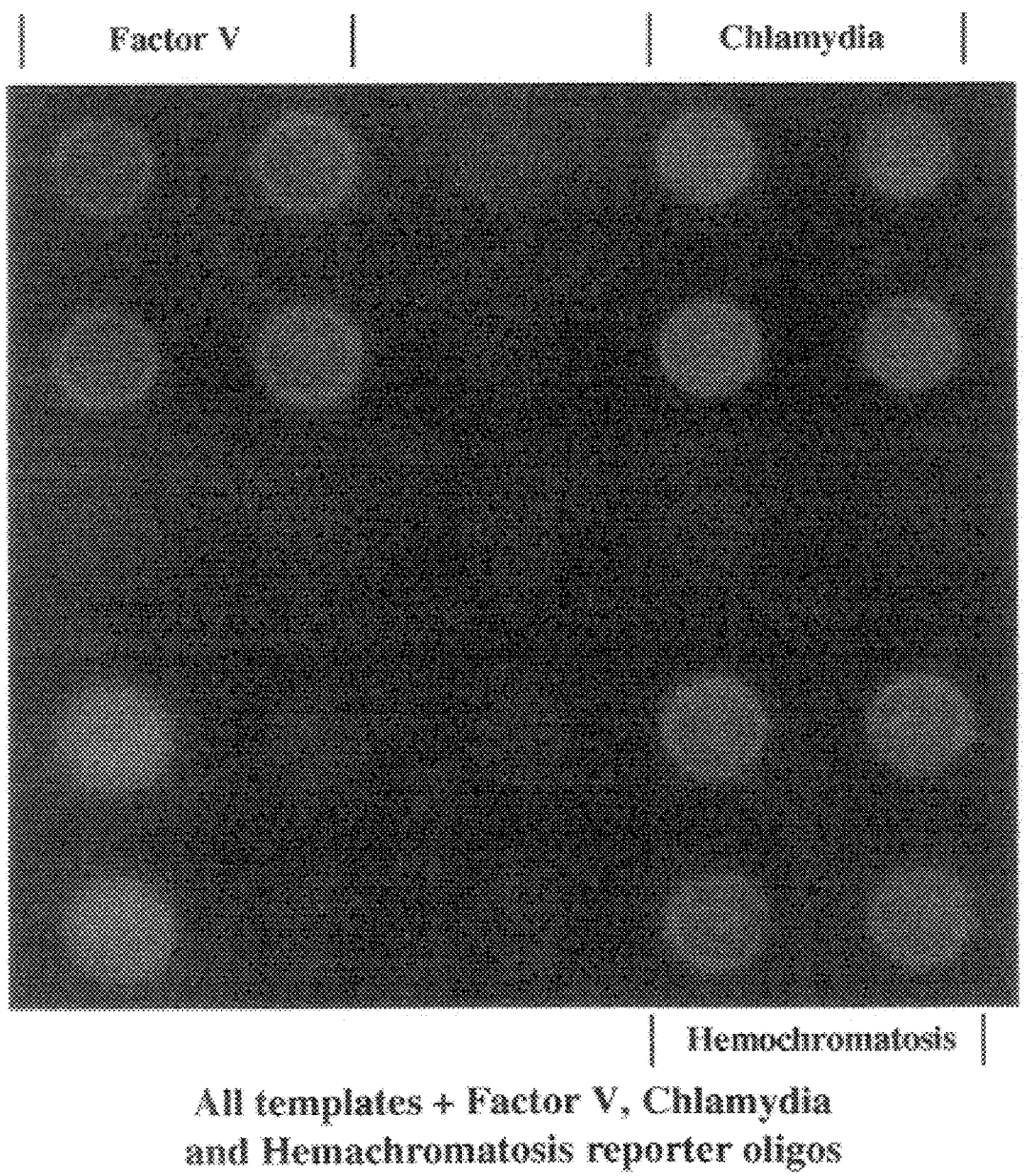
FIG. 20 is a photographic image showing specific localization of SDA amplified Factor V, Chlamydia, and Hemachromatosis gene targets which were amplified in the presence of multiple target species and SDA capture primer pairs specific for Factor V, Chlamydia, and Hemachromatosis that had been previously addressed to specific capture sites.
Figure 21:
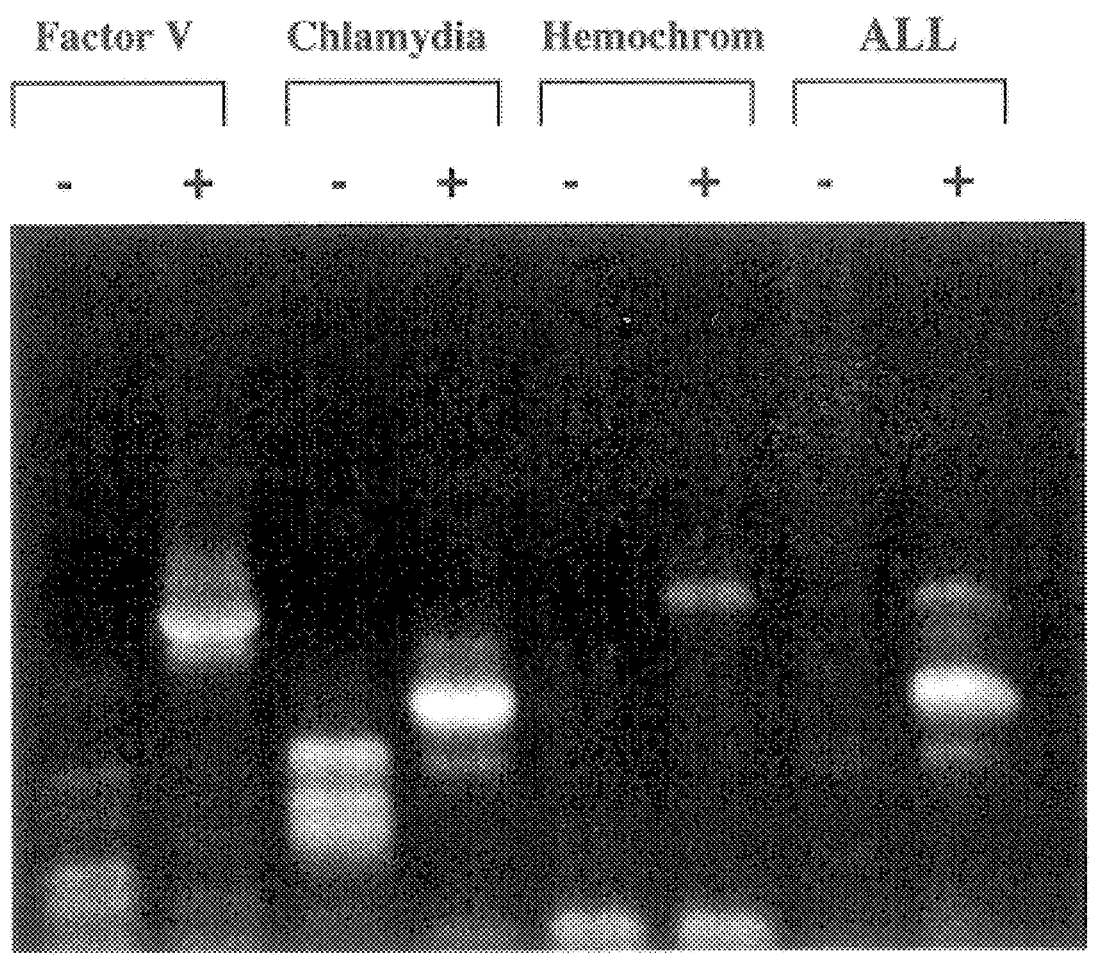
FIG. 21 is a PAGE gel showing results of a multiplex solution based SDA reaction for Factor V, Chlamydia, and Hemachromatosis gene targets. The minus lane indicates no template DNA present, while the plus lane indicates addition of template DNA.

Anchored SDA was performed on microchips in situ at 60° C. for 30 minutes as described previously and processed accordingly. As can be seen, no SDA amplicons can be detected when template is not hybridized to the SDA primers on the microchip (FIG. 17). However, when a mixture of the templates are hybridized to the SDA primers, simultaneous amplification of the three amplicon systems can be seen (FIGS. 18–20). Accordingly, when only one species of template is hybridized in the presence of all three types of SDA primer, only the area where the corresponding SDA primer is anchored shows a signal indicating amplification has taken place. This confirms the specificity, as well as the flexibility, of the anchored SDA system when done in situ on microchips. Interestingly, as shown in FIG. 21, when solution-based SDA is performed using the same three SDA primer sets, multiplex amplification is greatly compromised. Solution SDA was performed on Factor V, Chlamydia and Hemochromatosis separately, as well as together in one reaction (ALL) followed by analysis on a 6.0% non-denaturing polyacrylamide gel. As can be seen, all three systems amplify when done separately. However, when all three primer sets and templates are combined into one reaction, Factor V amplification is greatly depressed. Additionally, when the templates were hybridized to the primers by passive hybridization, the amplification efficiency was significantly reduced, possibly due to the inefficient hybridization caused by template reannealing. These results underscore the need in the art for a system such as that of the current invention for a multiplex amplification system that can perform multiplex amplification and detection of target species without hindrance as may be observed in solution based and/or passive hybridization systems.

Figure 22:
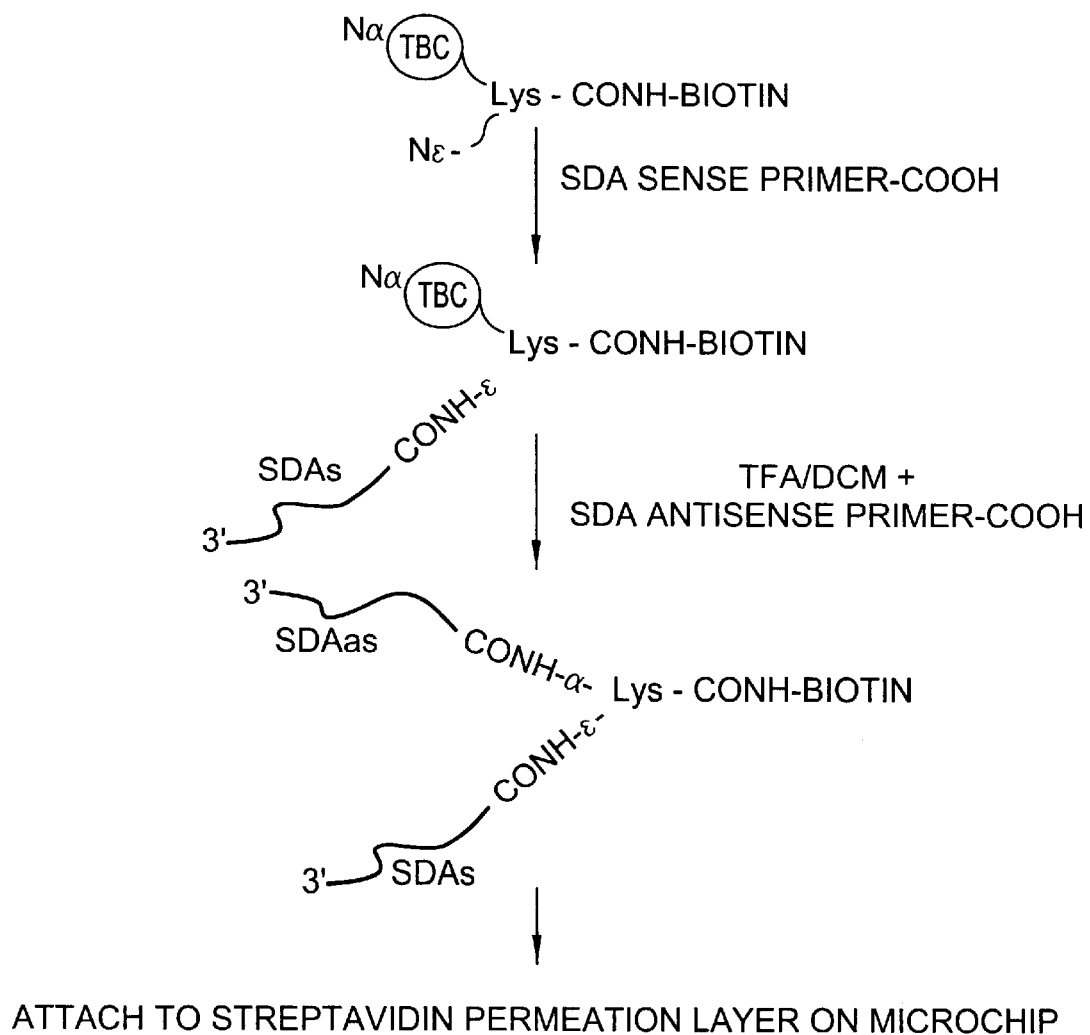
FIG. 22 is a diagram showing a proposed reaction sequence for synthesis of a branched SDA primer pair.

In a second embodiment of this example, the preparation of branched SDA target capture primer pairs may be synthesized by numerous means. In a preferred embodiment, the branched moiety may be produced as described below. First, as depicted in FIG. 22, the starting substrate for Y-primer synthesis is a biotin-conjugated lysine with a tert-butyloxy carbonyl-protected α-amino terminal. The tert-butyloxy carbonyl (TBC) moiety on the α-amino terminal allows selective attachment of the SDA primer arms separately. In this case, the α-amino terminal is protected but the α-amino terminal can react with carboxylic acid, allowing the SDA sense primer to be attached to the α-amino terminal end. The α-amino terminal end can then be deprotected with tri-fluoroacetic acid/dichloromethane (TFA/DCM), which removes the tert-butyloxy carbonyl moiety and allows attachment of the SDA antisense primer via the carboxylic acid terminal. This attachment sequence allows the formation of a Y-primer where both SDA primers are addressed to the branched moiety at their respective 5' ends. The resulting Y-shaped primer pair can then be attached to the streptavidin permeation layer on the microchip.

The synthesis of Y-shaped primer pairs for anchored SDA is intended to increase the overall efficiency of the SDA reaction twofold: 1) by placing the SDA primers in relatively close proximity of each other, thereby increasing the rate of interaction between extended amplicons of one strand and subsequent binding of the cleaved amplicon to the opposite strand primer; and 2) by increasing the density of primers in a given area over conventional oligonucleotide SDA primers. In the synthesis protocol above, the Y-primer is attached to the microchip permeation layer via a streptavidin-biotin bond; however, other amide-bond attachment chemistries can be used, including but not limited to prolinx, R—SH, or any other functional group onto the macromolecule. The branched primer pairs may be used in carrying out SDA reactions as described above.

EXAMPLE 8

Still another example provides an asymmetric amplification method to address the problem of hybridization between sense and antisense amplicons that are generated during SDA. When using SDA, generally, both sense and anti-sense strands are generated in equal amounts. Under typical conditions of amplification, the complementary strands hybridize together. However, hybridization of oligonucleotides to specific sites on a microelectronic array (both for hybridization of amplimers to capture oligonucleotides and detection of hybridized material by fluorescently labeled reporter oligonucleotides) requires generation of single stranded species from the amplicons. Therefore, the complementary strands that are hybridized together must be separated prior to hybridization to captures upon the array and/or prior to detection by labeled reporter unless one strand is amplified more than the other (i.e. unless amplification is asymmetric). This is conventionally done using heat or chemical denaturation before or after electronic addressing. Asymmetric amplification removes the need for such thermocycling step.

A key feature of asymmetric amplification is the generation of a preponderance of one amplicon over its complementary amplicon sequence. In a solution environment, this method is typically accomplished by having a disproportionate ratio of amplifying primers. In the initial stages of the amplification process, the effective concentration of the sense and antisense amplifying primers being in large excess to template produces an environment conducive to exponential amplification of the original double stranded template material. As the reaction proceeds, the amplifying primer originally present in lesser amounts is effectively exhausted thereby leading to conditions of linear amplification by the primer remaining in excess. The particular effect of the polymerase mediated displacement of amplified material during SDA ensures that this linearly amplified material is free in solution and available for hybridization without the necessity for denaturation of double stranded species. With respect to objects of the invention, an alternative approach is to place both primers in solution at the same concentration, but to add a competitor that partially inhibits, or "poisons" generation of one strand. Over time this will also lead to a preponderance of one strand of the amplified target.

Where capture probes are anchored, creation of predominantly one strand can be enhanced by designing anchored capture probes that are complementary to one strand of the amplicons being generated and released free into solution. In a preferred embodiment, the capture probes are different from normal SDA primers in two respects. First, they preferably do not possess a functional restriction site, thereby blocking the endonuclease nicking/polymerase extension-displacement steps. Second, the 3' ends of the capture probes preferably are not suitable for extension by polymerase activity. During SDA this modified capture primers will hybridize to amplicon strands effectively pulling them out of the SDA pathway so that they will not be available for further amplification. The capture of such single strands may be directed to occur at a capture site located at a remote position from the site where SDA is occurring. Thus, a bias in the strandedness of the amplicon population will be generated, which is an effective form of asymmetric amplification due to limiting the quantities of one strand of amplification product.

In another example asymmetric amplification may be enhanced by including in the SDA reaction a competitive inhibitor of one of the primers of a given set of primers. As in the above example, the competitive primer is preferably either non-extendible or non-cleavable. The inclusion of the competitive primer biases the reaction toward the creation of single-strands through a linear reaction process.

Oligonucleotide sequences are rendered non-extendible using various means including blocking the 3' OH end, and mismatching the 3' terminal nucleotides(s) with respect to the template sequence. Oligonucleotide sequences are rendered non-cleavable by modifying the oligonucleotide backbone through the inclusion of modified linkages such as phosphorothioates or more simply by changing the sequence at the restriction endonuclease recognition site. Probes modified as such remain fully competent for hybridization. The sequence of the competitor is preferably identical to (or nearly identical to) that of one of the amplification primers. The competitor can therefore compete with the amplification primer for hybridization with a target sequence. When bound to the target sequence, the competitor either (1) cannot be extended by DNA polymerase, or (2) can be extended to produce a copy of the target sequence. In the case where the competitor is extended, the competitor is modified such that resultant copies of the target sequence cannot be cleaved by a restriction enzyme. Different types of competitors are used depending on the amplification method being used.

In PCR, the competitor is modified such that it cannot be extended. Appropriate modifications are described above. In each cycle of the reaction, the competitor will compete with one of the PCR primers for hybridization to available target sequences. For example, in a reaction where the competitor is added at 10% the concentration of the PCR primer, roughly 10% of hybridization events will be abortive in that an extension product cannot be produced. The opposite PCR primer is free to hybridize to all available target sequences and be extended.

Therefore, a bias of about 10% in the relative number of the two extension products is produced in any given cycle. While a 10% bias in early cycles may not be significant since target concentration is low, such a bias will produce a high concentration of single-stranded material in late stage cycles (where nM quantities or greater of the extension products are being produced).

Figure 14:
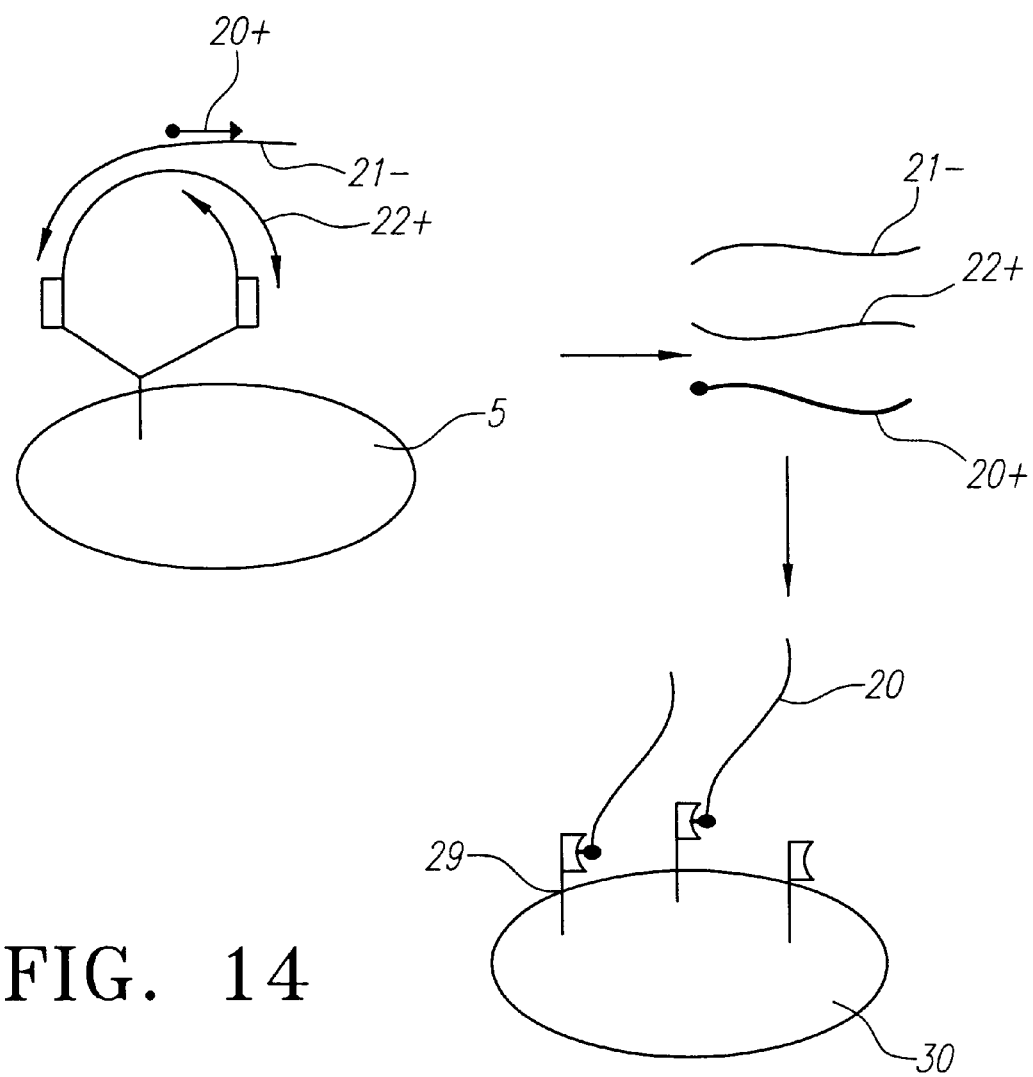
FIG. 14 is a schematic diagram showing the nature of using a signal primer to generate asymmetric ratios of nucleic acid amplicon chains such that the amplicons with signal may be electronically addressed to a capture pad for signal detection.

In SDA, several methods are preferable. Use of a non-extendible competitor will bias the production of double-stranded templates which will allow the nicking and extension reaction to preferentially produce one of the single-stranded displaced products. Use of an extendible, non-cleavable competitor leads to asymmetry by creating double-stranded products that cannot participate in the nicking/displacement reaction. Use of both types of competitors may be optimal as extension products produced from the non-cleavable primer become part of double-stranded molecules when only one strand can be nicked and displaced. (see FIG. 14).

EXAMPLE 9

In this example of the invention, SDA is carried out in conjunction with an electronically addressable microchip wherein the atmospheric pressure of the SDA reaction is elevated.

Where genomic nucleic acid is used, it is preferred that it be cleaved into fragments of between approximately 250–500 bp. This may be done by a restriction enzyme such as HhaI, FokI or DpnI. The selection of the enzyme and the length of the sequence should be such that the target sequence sought will be contained in its entirety within the generated fragments or that at least a sufficient portion of the target sequence will be present in the fragment to provide sufficient binding of SDA amplification primers. Other methods for generating fragments include PCR and sonication.

The primers used in this method generally have a length of 25–100 nucleotides. Primers of approximately 40 nucleotides are preferred. The primer nucleic acid sequence should be substantially homologous to the target sequence such that under high stringency conditions hybridization between primer and template nucleic acid will occur.

Target nucleic acid fragments are denatured to render them single stranded so as to permit binding of the primers to the target strands. Raising the temperature of the reaction to approximately 95° C. is a preferred method for denaturing the nucleic acids. Other methods include raising pH; however, this will require lowering the pH in order to allow the primers to bind to the target. Following the formation of single stranded target molecules, SDA is performed as discussed in the numerous examples discussed herein. Typically, the SDA reaction includes the use of at least one substituted nucleotide during primer extension to facilitate nicking of one strand during amplification. The nuclease may be any nuclease typically useful for SDA as discussed earlier.

In a preferred embodiment of this method, atmospheric pressure is elevated either before or after all the SDA reaction components are combined. The pressure is elevated to reduce star activity to effectively enhance the specificity of the restriction endonuclease for its target. The application of elevated pressure may also increase the specificity of primer interaction with the template nucleic acid and the overall rate of reaction of the enzymes employed, thereby reducing the time required for the SDA reaction while increasing its specificity. By reducing star activity, template independent amplification is decreased thereby reducing the competitive consumption of reagents by non-specific amplification.

Elevated pressure can be supplied during the amplification by various methods. For example, the reactions could be run in high pressure vessels. The reactions may also be run by placing the container in a reaction chamber attached to or part of a high-pressure apparatus (High Pressure Equipment Co., Erie, Pa.). It may be advantageous to overlay the aqueous reaction media with an immiscible phase, such as silicon oil (Sigma) by which pressure can be applied to the aqueous solution containing the target nucleic acid, nucleosidetriphosphates, and enzymes. Preferably, the pressure is elevated in the range of about 100 to about 500 atmospheres.

Polymerases useful in this method include those that will initiate 5'–3' polymerization at a nick site. The polymerase should also displace the polymerized strand downstream from the nick, and, importantly, should also lack any 5'→3' exonuclease activity and be heat stable. Polymerases, such as the large fragment of DNA polymerase I and the exonuclease deficient Klenow fragment of DNA polymerase I and a similar fragment from the Bst polymerase (New England Biochemicals, Beverly, Mass.) are useful. SEQUENASE 1.0 and SEQUENASE 2.0 (U.S. Biochemical), T5 DNA polymerase, and Phi29 DNA polymerases are also useful. Generally, thermophilic DNA polymerases are preferred. The exonuclease deficient thermophilic Klenow fragment of Bst DNA polymerase from *Bacillus stearothermophillus* (New England Biochemicals, Beverly, Mass.) is most preferred.

In this method, a single reaction temperature may be employed after denaturation has occurred, and such temperature should be high enough to set a level of stringency that minimizes non-specific binding but low enough to allow specific hybridization to the target strand. In addition, use of temperature preferably from about 45° C. to about 60° C. should support efficient enzyme activity. Denaturation of the enzymes and nucleic acid is to be avoided.

During the SDA reaction cycles, theoretically about 20 repetitions or cycles will result in about a $10^6$-fold amplification (i.e., SDA×$2^{20}$=$10^6$). Typically, $10^8$-fold or greater amplification is seen in about 30 minutes of amplification.

High pressure SDA is beneficial for various uses including generation of high fidelity single-stranded nucleic acid probes or single-stranded templates for sequencing. Toward this goal, high pressure SDA can be conducted either with a single primer or using two primers wherein one primer is in excess over the other. The result is excess production of one displaced single strand over the other.

The presence of the amplified target then can be detected by any number of methods. One method is to detect reaction products of a specific size by means of gel electrophoresis. This method is particularly useful when the nucleotides used are labeled with a radio-label, such as $^{32}$P. Other methods include labeling the nucleotides with a physical label, such as biotin. Biotin-containing reaction products can then be identified by means of avidin bound to a signal generating enzyme, such as peroxidase. Another method is elongation of a fluorescently labeled internal primer.

Detection systems useful in the practice of this invention comprise homogeneous systems, which do not require separation, and heterogeneous systems. In each system, one or more detectable markers are used and the reaction or emission from the detection system is monitored, preferably by automated means. Examples of homogeneous systems include fluorescence polarization, enzyme mediated immunoassays, fluorescence energy transfer, hybridization protection (e.g., acridinium luminescence) and cloned enzyme donor immunoassays. Examples of heterogeneous systems include enzyme labels (such as peroxidase, alkaline phosphatase and beta-galactosidase), fluorescent labels (such as enzymatic labels and direct fluorescence labels (e.g., fluorescein and rhodamine)), chemiluminescence and bioluminescence. Liposomes or other sac like particles also can be filled with dyes and other detectable markers and used in such detection systems. In these systems, the detectable markers can be conjugated directly or indirectly to a capture moiety or the amplified products can be generated in the presence of a receptor which can be recognized by a ligand for the receptor.

Protocol for Strand-Displacement Amplification (SDA) Under Elevated Pressure

Amplification reactions utilize approximately 100 ng of genomic DNA (Factor V) in a total volume of 50 µl. The genomic DNA (human placental DNA; Becton-Dickinson) is denatured at 95° C. for 5 minutes followed by centrifugation to collect condensate. Next, 1 µl of SDA primer mix is added (50 µM each reaction) and incubated at 60° C. for 5 minutes. SDA mix (40 mM $k_2HPO_4$ pH 7.6, 1.4 mM each dCTPαS, dTTP, dATP and dGTP, 8.3 mM $MgCl_2$, 40 units/rxn BsoBI (New England Biochemicals), 15.6 units/rxn Bst polymerase (New England Biochemicals), and 0.05 µM each SDA bumper primers are added and pre-warmed for 5 minutes at 60° C. followed by addition of the mix to SDA primers and target sample. Silicon oil is added to the top of the reaction tubes and placed in high a pressure chamber. The pressure is elevated to between 100 and 500 atmospheres and incubate at 60° C. for 30 minutes. Following the reaction period, the pressure is reduced to atmospheric pressure and stopped by addition of 10 μl of 100 mM EDTA. SDA products are visualized by electrophoresing on 6% non-denaturing polyacrylamide gels. The gels are stained with ethidium bromide and photographed under UV-fluorescence.

Alternatively, it is possible to use a device wherein the temperature and/or pressure is elevated prior to the addition of the polymerases and/or restriction endonuclease.

The use of elevated pressure can also be used in the performance of anchored SDA, or any SDA procedure as described above. Specifically, when anchored SDA is performed on electronically addressable microchips, elevated pressure should decrease star activity and increase efficiency by reducing primer independent amplification.

EXAMPLE 10

In another example, SDA may be used in conjunction with electronically addressable microchips wherein the SDA reaction is "ligation-dependent" or "ligation-based". This method involves the SDA amplification of a ligated probe using a pair of universal amplification primers. The amplification primers are universal in the sense that they are designed to amplify all ligated probes in a test reaction whether the reaction is multiplexed or directed to a singular target. The ligated probe is formed by ligating together a pair of ligation probes that have hybridized to a target sequence. No bumper primers are necessary.

In another embodiment, a method of ligation-based SDA is provided where the method is unassisted by an electronic microchip. In this embodiment it is not necessary to, inter alia, anchor any primers, which is a procedure that assists in separating primer sets during multiplex amplification, because the primers are universal—there is no need to direct target sequences to specific primers.

The following functional descriptions of the oligonucleotide reagents are not intended to define or limit their actual physical composition. Rather, the description merely demonstrates that each reagent exhibits certain functional characteristics. Thus, it should be noted that the functional regions of a given oligonucleotide reagent may overlap, or in fact be co-extensive, as where a specific nucleic acid sequence is able to accomplish more than one function. Additionally, the individual base sequence in any given oligomer depends upon the target nucleic acid of interest, the restriction enzyme chosen for use in SDA, or an arbitrary sequence chosen for portions of the amplification primers and ligation probes so that a degree of universality can be incorporated into the amplification protocol.

Figure 23A:
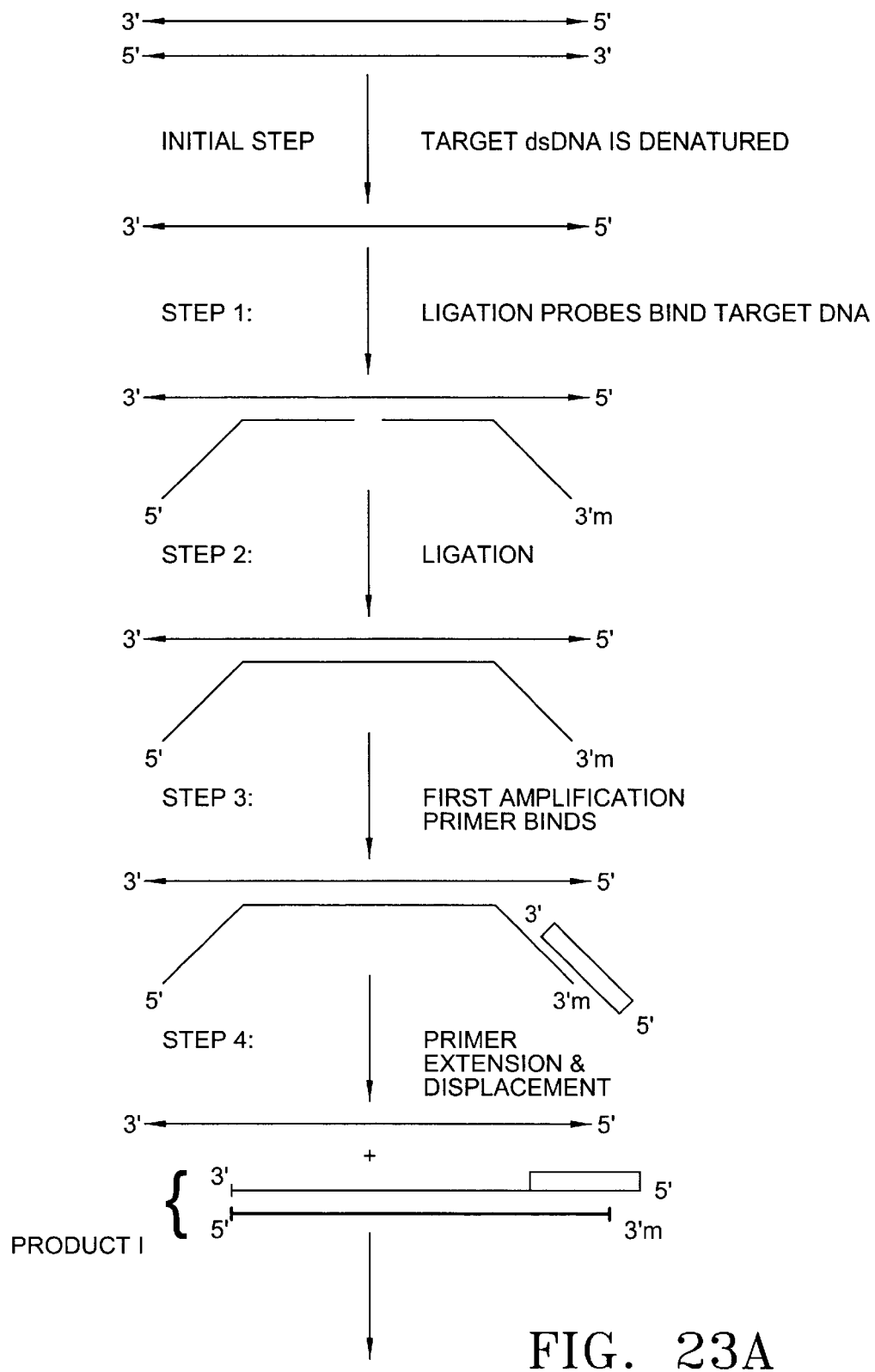
FIG. 23(a) illustrates the ligation probes and amplification primers that would be used to detect the Salmonella spaQ gene present in a sample using the method illustrated in FIG. 23(a–c).
Figure 23B:
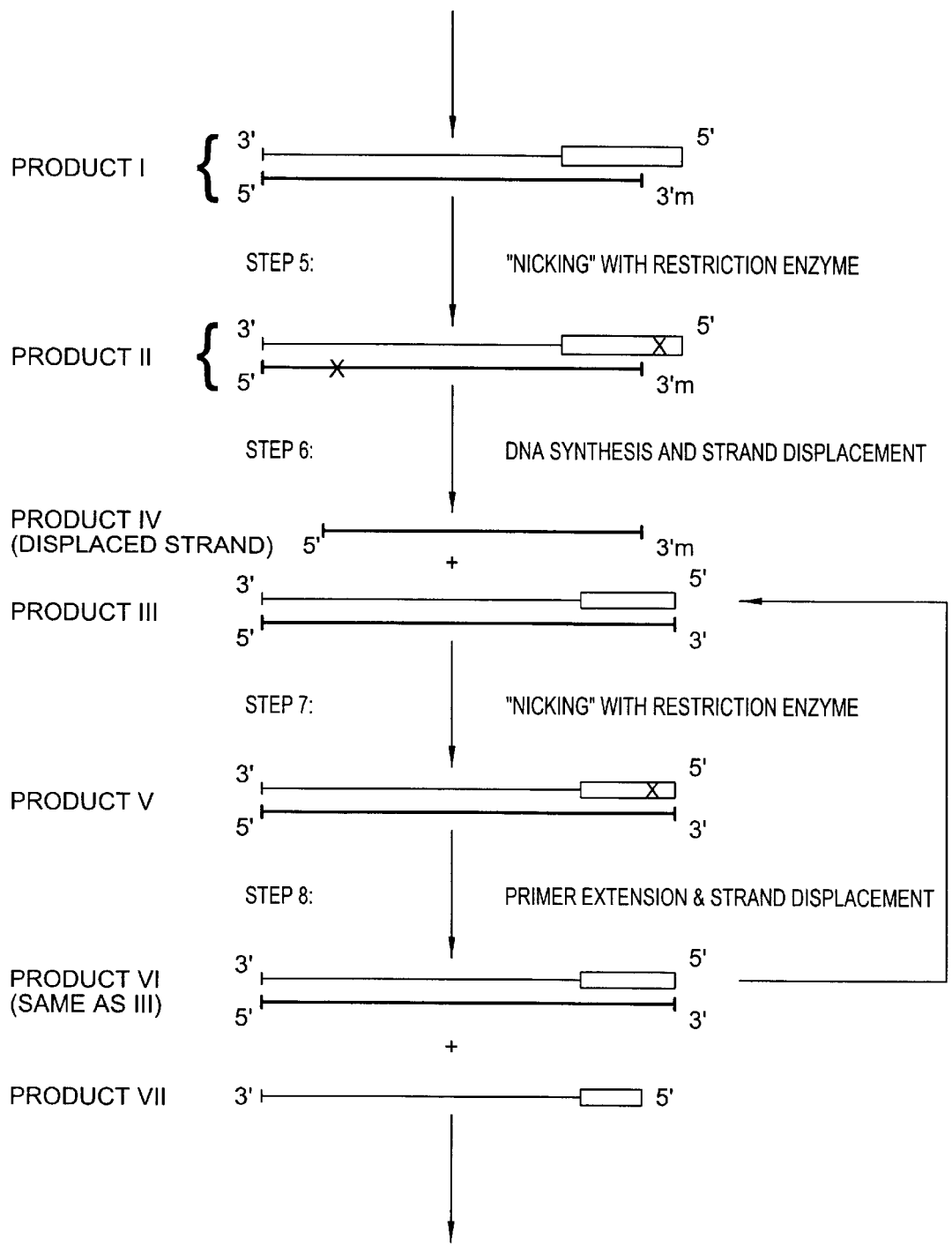
FIGS. 23(a–c) illustrate a reaction pathway for the ligation-dependent amplification of a target nucleic acid sequence.
Figure 23C:
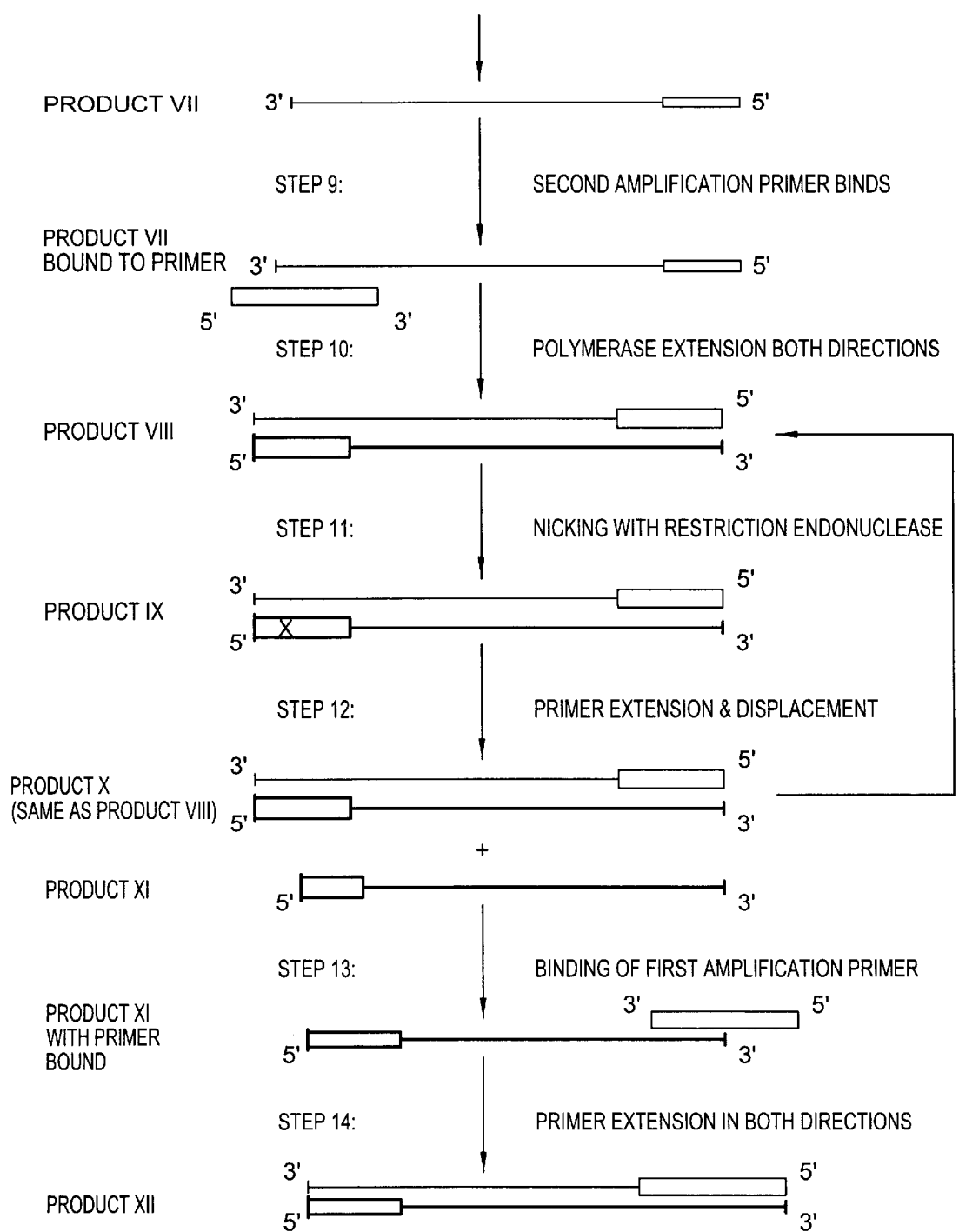

In operation, as illustrated in FIGS. 23(a–c), the ligation-based SDA method uses a pair of ligation probes that anneal to adjacent nucleic acid sequences on a target. Functionally, the pair of ligation probes bind to a target nucleic acid sequence such that they can be ligated together while they are annealed to the target to form a ligated probe template. Ligation will occur only following hybridization of both ligation probes of a ligation probe pair to a target sequence.

The first ligation probe can be divided into three functional regions: a 5' region able to hybridize to target nucleic acid; a middle region; and a 3' region comprising a nucleic acid sequence that is able to hybridize to the first amplification primer. The second ligation probe can also be divided into three functional regions: a 5' region having a nucleic acid sequence identical to nucleic acid sequences found in the second amplification primer and having a restriction endonuclease recognition site; a middle region; and, a 3' region able to hybridize to target nucleic acid.

With respect to the amplification primers, the first amplification primer can be divided into two functional regions: a 5' region containing a restriction endonuclease recognition site and a 3' region that is able to hybridize to the first ligation probe. The second amplification primer can also be divided into two functional regions: a 5' region that contains a recognition site for a DNA restriction endonuclease and a 3' region comprising nucleic acid sequence having the same sequence as the 5' region of the second ligation probe.

The ligation-based SDA reaction comprises a number of component steps. In Step 1, the pair of ligation probes anneal to adjacent sequences of single-stranded target nucleic acid such that the second ligation probe hybridizes to the target strand at a position on the target that is 3' to the hybridization position of the first ligation probe. In Step 2, DNA ligase catalyzes the ligation of the two ligation probes to form the ligated probe template. In a preferred embodiment, the 3' end of the ligated probe template is modified to prevent primer extension from that end (FIGS. 23(a–c)).

In Step 3, the first amplification primer binds to the 3' end of the ligated probe template such that the amplification primers extend beyond the end of the template forming a 5' overhang. In a preferred embodiment, DNA polymerase catalyzes new DNA synthesis from the 3' end of the first amplification primer causing the ligated probe to be displaced from the target nucleic acid. This results in the release of single-stranded target nucleic acid and the creation of double-stranded DNA oligonucleotide having a 5' overhang (labeled Product I, FIG. 23). The release of single-stranded target nucleic acid and the creation of the double-stranded oligonucleotide occurs without the assistance of bumper primers. Moreover, the target single strand becomes available for further binding of unligated first and second ligation probes.

Product I thus comprises a first strand having a sequence from 5' to 3' corresponding to the ligated probe template, and a second strand complementary to the ligated probe template strand with an additional nucleic acid sequence at its 5' end corresponding to the 5' end of the first amplification primer. This double stranded DNA molecule is capable of undergoing a series of SDA reactions that produce single stranded DNA molecules able to be bound and amplified by the universal amplification primers. The double stranded DNA molecules that result from these reactions are also susceptible to amplification. Nicking by a restriction endonuclease, followed by primer extension and strand displacement, substantially regenerates the double stranded DNA starting material. Together, these ligation-dependent SDA reactions ultimately amplify oligonucleotide sequences corresponding to the ligated probe, thereby allowing the detection of the target sequence. These reactions are described in detail below.

In Step 5, Product I is nicked by a restriction enzyme to create Product II. In Step 6, Product II undergoes primer extension and strand displacement from the nick, resulting in Product III and Product IV. Product III is essentially the same as Product I except that the first strand of Product III (which corresponds to the first strand of Product I) contains an additional sequence at its 3' end complementary to the 5' end of the first amplification primer. Product IV is a single-stranded molecule with a sequence comprising the first strand of Product II located 3' to where this strand was nicked by the restriction endonuclease.

In Step 7, Product III is nicked by a restriction endonuclease to create Product V. In Step 8, Product V undergoes primer extension and strand displacement to create Product VI and Product VII. Product VI is essentially the same as Product III. Product VII is a single stranded DNA molecule comprising the nicked strand of Product V located 3' to the nick site.

In Step 9, the second amplification primer binds to Product VII. In Step 10, Product VII undergoes a primer extension reaction in both directions to create Product VIII. Product VIII is a double stranded nucleic acid molecule, the first strand having a sequence corresponding to product VII plus an additional 3' sequence that is complementary to the 5' region of the second amplification primer, and a second strand that is complementary to the first strand. In Step 11, Product VIII is nicked with a restriction endonuclease to create Product IX. Product IX is essentially the same as Product VIII except that the 5' end of Product IX contains a nick in the nucleic acid corresponding to the 5' region of the second amplification primer. In Step 12, Product IX undergoes primer extension and strand displacement to create Products X and XI. Product X is the same as Product VIII. Product XI is a single stranded nucleic acid molecule with a sequence corresponding to the sequence 3' of the nick, on the nicked strand of Product IX. In Step 13, Product XI is bound by the first amplification primer and in step 14, primer extension in both directions results in Product XII. Product XII is a double stranded nucleic acid molecule similar to Product III in the sense that it can enter the above described reaction pathway following step 6 and prior to step 7. Thus, an initial reaction product of the ligation-dependent SDA pathway is ultimately substantially regenerated.

As described earlier, the SDA reaction may be carried out using anchored probes. With regard to ligation-based SDA, the anchored probes are preferably either one or both of the amplification primers or one or both of the ligation probes.

Experimental Data for Example 10
Experiment 1
In this example, a general protocol for the preferred ligation-based SDA of a target nucleic acid is provided. Concentrations and volumes of reaction components, and time and temperature profiles may be adjusted as necessary. Volumes assume a 25 µl ligation reaction volume and a 50 µl final reaction volume for SDA.

In a 250 µl microcentrifuge tube, a 5 µl aliquot of an aqueous ligation probe solution is added such that the final concentration of each probe in a 25 µl ligation reaction volume will be 5 nM. Next, 10 µl of a solution of non-specific (carrier) DNA (e.g., Calf thymus DNA is added to a final concentration of 20–100 µl/ml. Next, 5 µl of the sample containing the template nucleic acid (e.g. Cell lysate or purified genomic DNA) at an appropriate concentration is added and the tube is placed at 60° C. for 3 minutes to allow temperature equilibration. Following equilibration, 5 µl of a solution containing a thermostable DNA ligase is added along with sufficient 5×strength mixture of buffer components necessary to allow function of the DNA ligase, and to allow probe hybridization. See Table IV.

The 25 µl ligation reaction is incubated at 60° C. for 15 minutes and then 20 µl of an SDA stock mix containing additional buffer components, dNTPs, and amplification primers, is added to give final reaction concentrations (in 50 µl) as shown in Table V. In one embodiment an additional step is included where the reaction is heated to 95° C. for 3 minutes to denature the ligated probes from the template and then the tube is equilibrated at 60° C. for 3 minutes. To this reaction mixture 5 µl of liquid containing the SDA enzymes is added to give the following final concentrations in a 50 µl final reaction volume:

BSOB1 restriction enzyme: 0.8 enzyme units/µl (40 U/rxn)

Bst DNA polymerase: 0.32 enzyme units/µl (16 U/rxn)

The reaction mixture is incubated at 60° C. for 30 minutes then the reaction is stopped by placing the reaction mixture on ice.

TABLE IV

| Buffer Component | Final Concentration in Reaction for Each Ligase | |
|---|---|---|
| | Taq DNA ligase (1 U/rxn) | Pfu DNA ligase (0.2 U/rxn) |
| Tris-HCl pH 7.6 | 10 mM | 10 mM |
| Potassium Acetate | 25 mM | 25 mM |
| Magnesium Acetate | 10 mM | 10 mM |
| Dithiothreitol | 1 mM | 1 mM |
| Nicotinamide adenine dinucleotide | 1 mM | NONE |
| Adenosine triphosphate | NONE | 10 µM |

TABLE V

| SDA Component | Final Concentrations in 50 µL Reaction (Note: includes contribution from ligation reaction) |
|---|---|
| Potassium phosphate | 35 mM |
| Bovine serum albumin | 80 µg/ml |
| Magnesium acetate | 10 mM |
| Deoxynucleotide triphosphates (equal mixture of dATP, dC$_\alpha$STP, dGTP, TTP) | 1.4 mM |
| Amplification primers (S1 and S2) | 250 nM |

Experiment 2
In this further example, the Salmonella spaQ gene (a portion of which is indicated on FIG. 23d and designated SEQ. ID. No. 41) potentially present in a sample is amplified. The reaction protocol as described in Experiment 1 is followed using the ligation probes LP1 (SEQ. ID. No. 37) and LP2 (SEQ. ID. No. 38) and amplification primers S1 (SEQ. ID. No. 39) and S2 (SEQ. ID. No. 40) which are illustrated in FIG. 23(d). The example described in Experiment 2 is intended to have general applicability. One could create different target-specific ligation probes for use with the amplification primers S1 and S2 by replacing the sequences of ligation probes L1 and L2 complementary to the spaQ gene with sequences complementary to another target nucleic acid of interest. Moreover, amplification primers S1 and S2, such as those depicted in FIG. 23(d) may be used in a multiplex amplification of more than one target nucleic acid.

Experiment 3
At high concentrations of ligation probe, ligase may catalyze the ligation of the ligation probes in a target-independent manner. The resulting ligated probe can support SDA and may thus create a false positive signal. In this further example, a preferred aspect of ligation-dependent SDA is described where this problem is overcome by rendering the ligation probes initially incapable of being ligated together by ligase. In this embodiment, a pair of unligateable probes is rendered ligateable to allow target-specific, ligation-dependent SDA.

Generally, the amplification of a background molecule that is target independent may be prevented by modifying the ends of the ligation probes that are involved within the ligation junction. This can take place in several ways. One such modification involves the modification (including removal, blocking, etc.) of the 3' hydroxyl group present on the 3' terminal nucleotide of the second ligation probe (the upstream probe). Another such modification involves the modification (including removal, blocking, etc.) of the 5' phosphate group present on the 5' terminal nucleotide of the first ligation probe (the downstream probe). Various methods have been and can be devised wherein the removal and or alteration of these modifications occurs preferentially in the presence of target DNA.

Specifically, one aspect of this example provides for modifying the 3' hydroxyl group present on the 3' terminal nucleotide of the second ligation probe (the upstream probe) to prevent blunt end ligation between the ligation probes. The modified unligateable probe is rendered ligation competent using an endonuclease, preferably Endonuclease IV. This reagent is able to excise 3' terminal nucleotides from oligonucleotides and thus is used to excise the 3' terminal nucleotide of the second ligation probe to reveal a new 3' terminal nucleotide with a 3' hydroxyl group. This reaction is more preferred when the ligation probe substrate is associated with target DNA and less preferred when the ligation probe substrate is unassociated with other DNA molecules. Consequently, once the ligation probes are bound to target DNA, the endonuclease (preferably Endonuclease IV) is able to excise the 3' terminal nucleotide of the second ligation probe to reveal a new 3' terminal nucleotide with a 3' hydroxyl group. The free 3' hydroxyl group of the second ligation probe, along with the free 5' phosphate group of the first ligation probe, are now substrates for ligation by DNA ligase.

Since endonuclease tends to operate more efficiently when the substrate oligonucleotide is double stranded it will preferentially excise the 3' terminal nucleotide of the second ligation probe when this probe is bound to target DNA, not when it is free in solution. Because the endonuclease preferentially renders the initially ligation-incompetent ligation probes ligation-competent when they are in the presence of target DNA, the target independent amplification of background molecules is decreased.

Another aspect of this example provides for the modification (including removal, blocking, etc.) of the 5' phosphate group present on the 5' terminal nucleotide of the first ligation probe (the downstream probe) to prevent blunt end ligation between the ligation probes. The modified unligateable probe is rendered ligation-competent using a DNA polymerase with exonuclease activity. This reagent will allow DNA polymerization (new DNA synthesis) to occur from the 3' end of the upstream probe (the second ligation probe) into the 5' end of the downstream (first ligation) probe. When the polymerase contacts the 5' end of the first ligation probe it will begin to excise nucleotides from the 5' end. As it excises nucleotides from the first ligation probe, nucleotides are added to the 3' end of the second ligation probe. In essence, this moves the "gap" between the first and second ligation probes, the junction to be ligated by ligase, from 5' to 3'. By controlling the amount and/or type of free nucleotide present in solution, the degree of excision and replacement can be limited. Following dissociation of the polymerase the junction contains a free 3' hydroxyl group and a free 5' phosphate group, both of which are substrates for ligation by DNA ligase. As indicated above, this reaction is more preferred when the ligation probe substrate is associated with target DNA and less preferred when the ligation probe substrate is unassociated with other DNA molecules. Again, this is because the reaction that renders the ligation probes ligateable prefers that the ligation probes be annealed forming dsDNA. As is understandable to one skilled in the art, such annealing is preferred for target DNA rather than annealing to non-target DNA. Thus, independent amplification of background molecules is decreased.

Yet another aspect of this example provides for blocking ligation using base-paring mismatching. Here, ligation is prevented between the first and second ligation probes by having the 5' end of the downstream (first) probe contain one or more mismatched bases. If a probe is said to contain a mismatched base, it should be understood to mean that the probe contains a nucleotide that is not complementary to target DNA sequences, in a region of the probe otherwise complementary to the target DNA. Mismatched bases prevent ligation by DNA ligase until the mismatched bases are excised, as in the above stated example, with DNA polymerase.

To demonstrate the exonuclease/ligase-dependent SDA (XL-SDA) aspect of this invention, as described in this further example, the nine sets of ligation probes shown in Table VI were synthesized. These probes were designed to identify the various bacterial species shown. The probes have regions complementary to the specific bacterial genes and regions designed for SDA amplification primer binding.

TABLE VI

| Bacterial gene, product | Genus/Species/Serotype identified | Ligation probe 1 (5'–3') | Ligation probe 2 (5'–3') |
|---|---|---|---|
| stx1, Shiga-like toxin-I | Shiga toxin-producing E. coli (STEC) and Shigella dysenteriae type I | GAGGGCGGTTTAATAA TCTACGGTGGTCGAGT ACGCCTTAA (SEQ. ID. No. 45) | CGATTCCGCTCCAGACTT CTCGGGTGTACTGAGATC CCCTTGTCAGAGGGATAG ATCCAGAGG (SEQ. ID. No. 46) |
| stx2, Shiga-like toxin-II | STEC | GATGGAGTTCAGTGGT AATACAATGTGGTCGA GTACGCCTTAA (SEQ. ID. No. 47) | CGATTCCGCTCCAGACTT CTCGGGTGTACTGAGATC CCCTGGTTTCATCATATCT GGCGTT (SEQ. ID. No. 48) |
| eaeA, intimin | E. Coli 0157:H7 | GACGCTGCTCACTAGA TGTCTAGGTCGAGTAC GCCTTAA | CGATTCCGCTCCAGACTT CTCGGGTGTACTGAGATC CCCTGGTTATAAGTGCTT |

TABLE VI-continued

| Bacterial gene, product | Genus/Species/Serotype identified | Ligation probe 1 (5'—3') | Ligation probe 2 (5'—3') |
|---|---|---|---|
| spa Q, surface antigen-presenting protein | Salmonella species | GATGATGTCATGTTGC AATGTCCTGGTCGAGT ACGCCTTAA (SEQ. ID. No. 51) | (SEQ. ID. No.49) GATACTCCAG (SEQ. ID. No. 50) CGATTCCGCTCCAGACTT CTCGGGTGTACTGAGATC CCCTCATTTAACTATCCC GTCTCGT (SEQ. ID. No. 52) |
| gnd, 6-phosphogluconate dehydrogenase | Salmonella typhi, Salmonella paratyphi | GAGTAATTACCGTCTT CATCTTTTTTTGGTCGA GTACGCCTTAA (SEQ. ID. No. 53) | CGATTCCGCTCCAGACTT CTCGGGTGTACTGAGATC CCCTGGCTTCATCAAGAA TAACATCTATC (SEQ. ID. No.54) |
| ipaH, pathogenicity-associated gene | Shigella species and enteroinvasive E. coli | GATTTACGGACTGGTT CTCCCTTGGTCGAGTA CGCCTTAA (SEQ. ID. No. 55) | CGATTCCGCTCCAGACTT CTCGGGTGTACTGAGATC CCCTTCAGAAGCCGTGAA GAGAATG (SEQ. ID. No. 56) |
| sodB, superoxide dismutase | Campylobacter species | GACCAAAACCATCCTG AACCATGGTCGAGTAC GCCTTAA (SEQ. ID. No.57) | CGATTCCGCTCCAGACTT CTCGGGTGTACTGAGATC CCCTTTCTAGTTTTTGATT TTTAGTATTATA (SEQ. ID. No. 58) |
| asd, aspartate semialdehyde dehydrogenase | Vibrio species | GAGTAGAGGTATGTGA TGAGCCAATGGTCGAG TACGCCTTAA (SEQ. ID. No. 59) | CGATTCCGCTCCAGACTT CTCGGGTGTACTGAGATC CCCTCTTTGGCTAAACTC GGTTTTC (SEQ. ID. No. 60) |
| lcrV, Yersinia V-antigen | Yersinia species | GATTAGCTGAGCTTAC CGCCGTGGTCGAGTAC GCCTTAA (SEQ. ID. No. 61) | CGATTCCGCTCCAGACTT CTCGGGTGTACTGAGATC CCCTCCGTAGCAAGTTGC GTGAAG (SEQ. ID. No. 62) |

The probes were added to identical sets of ligation-SDA reaction such that the number of ligation probe sets in the reactions increased in the order: 1 set (spaQ), 5 sets (spaQ, $stx_1$, $stx_2$, sodB, ipaH), 6 sets (as 5+lcrV), 7 sets (as 6+asd), 8 sets (as 7+eaeA), 9 sets (as 8+gnd), and such that the final concentration of each probe was 5 nM.

A total extract of *Salmonella enteritidis* genomic DNA was added as a template such that the estimated number of genome equivalents was either $10^5$, $10^4$, $10^3$ or zero as a negative control. XL-SDA reactions were performed as described below, and the reaction products analyzed by both acrylamide gel electrophoresis and electronic hybridization on a microelectrode array.

XL-SDA reactions were performed as follows although the concentrations and volumes of reaction components and time/temperature profiles may be adjusted as necessary. The volumes used assume a 25 μl ligation reaction volume and a 50 μl final reaction volume for SDA.

In a 250 μl microcentrifuge tube, solutions of the following reagents were combined to give the final concentrations shown: (1) two (or more) target-specific ligation probes (e.g. probe exo-LP1 having a 5' sequence substantially complimentary to a portion of the target sequence of interest and a 3' sequence complimentary to a universal amplification primer and probe exo-LP2 having a 3' end sequence substantially complementary to a portion of the target sequence located downstream of LP1 and a 5' end sequence identical to a second universal amplification primer) to give probe concentrations of 5 nM of each probe; and, (2) a solution containing the template DNA of interest.

The exonuclease/ligation reaction was initiated by the addition of the following: a thermostable DNA ligase (such as Taq DNA ligase or Pfu DNA ligase); a thermostable DNA polymerase having 5'-3' exonuclease activity, (such as Taq DNA polymerase); buffer salts to give final concentrations shown in Table VII below; and dATP at 2.8 mM in a 25 μl reaction.

TABLE VII

| Buffer Component | Final concentration in reaction for each ligase | |
|---|---|---|
| | Taq DNA ligase (1 U/rxn) | Pfu DNA ligase (0.2 U/rxn) |
| Tris-HCl pH 7.6 | 10 mM | 10 mM |
| Potassium Acetate | 25 mM | 25 mM |
| Magnesium Acetate | 10 mM | 10 mM |
| Dithiothreitol | 1 mM | 1 mM |
| Nicotinamide adenine dinucleotide | 1 mM | NONE |
| Adenosine triphosphate | NONE | 10 μM |

The ligation/exonuclease reaction was incubated at 60° C. for 15–30 minutes. Then, 20 μl of an SDA stock mix containing additional buffer components, a mixture of dNTPs such that the final reaction contains all four dNTPs, and amplification primers, is added to give the final reaction concentrations (in 50 μl) shown in Table VIII.

TABLE VIII

| SDA Component | Final Concentrations in 50 μl reaction |
|---|---|
| Potassium phosphate | 35 mM |
| Bovine serum albumin | 80 μg/ml |
| Magnesium acetate | 10 mM |

TABLE VIII-continued

| SDA Component | Final Concentrations in 50 μl reaction |
| --- | --- |
| Deoxynucleotide triphosphates (dGTP, dC$_{\alpha S}$TP, TTP) | 1.4 mM |
| Amplification primers (S1 and S2) | 250 nM |

Then, 5 μl's of a solution containing the SDA enzymes is added to give the following final concentrations: BsoB1 restriction enzyme at 0.8 enzyme units/μl (40 U/rxn) and Bst DNA polymerase at 0.32 enzyme units/μl (16 U/rxn). This reaction mixture is then incubated at 60° C. for 30 minutes to allow the SDA reaction to proceed. The reaction is stopped by placing it on ice and the amplified products are detected.

Figure 24:
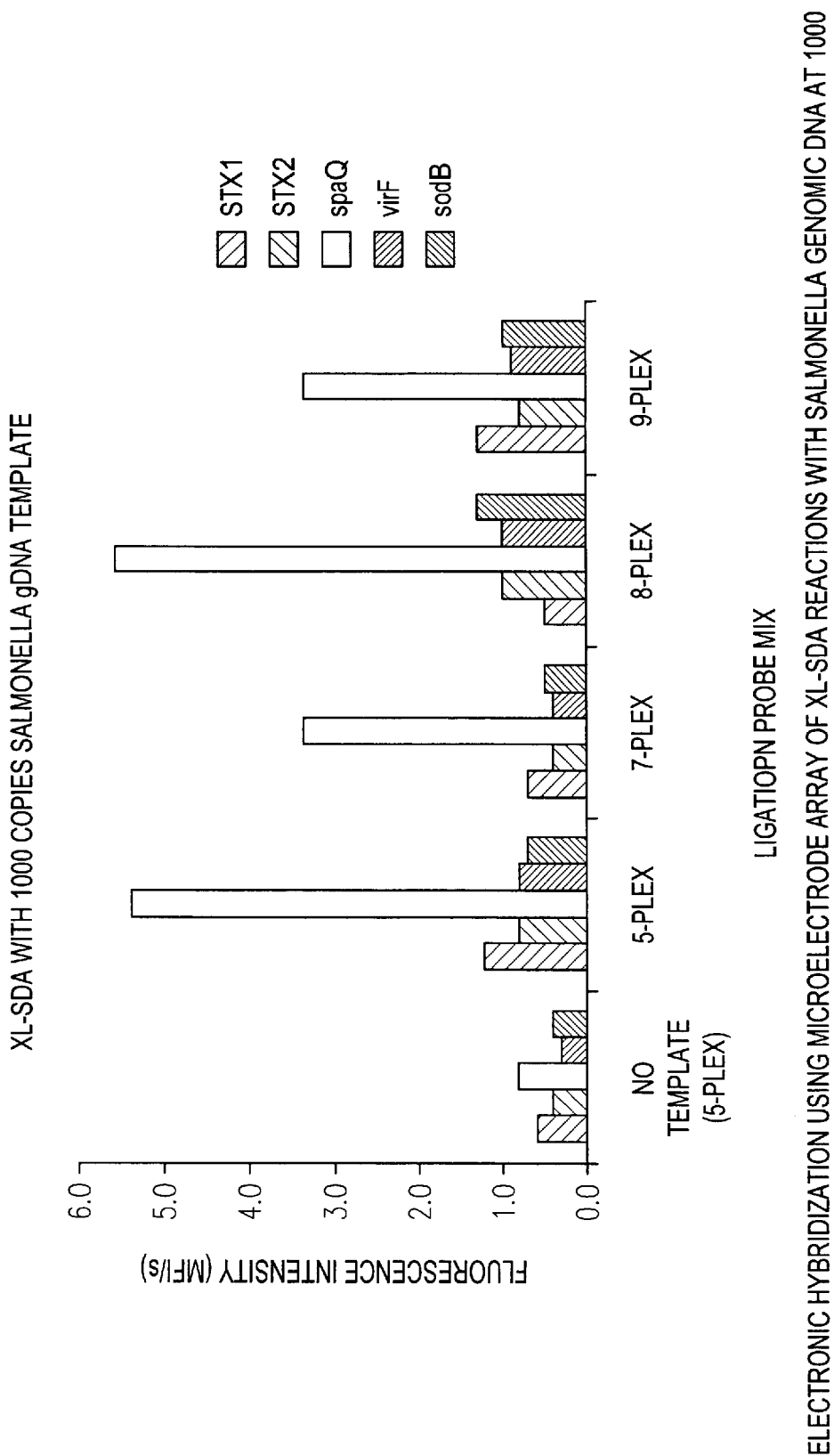
FIG. 24 is a graph showing specific amplification using the exonuclease ligation dependent SDA aspect of this invention, as explained in Example 10, in conjunction with a microelectrode array having capture probes for five bacterial genes pre-arranged at discrete locations.

The reaction products generated were analyzed by both acrylamide gel electrophoresis and electronic hybridization on a microelectrode array. An analysis of 5 μl of the XL-SDA reactions by acrylamide gel electrophoresis demonstrated that specific amplification product is made in a template concentration-dependent manner in all combinations of ligation probes. To demonstrate specific amplification of the *Salmonella enteritidis* spaQ gene sequence, the ligation-SDA reaction products were analyzed on a microelectrode array where specific capture probes for five of the bacterial genes are pre-arranged at discrete locations. FIG. 24 shows that in all samples analyzed, the spaQ sequence was detected.

The foregoing is intended to be illustrative of the embodiments of the present invention, and are not intended to limit the invention in any way. Numerous variations and modifications of the present invention may be effected without departing from the true spirit and scope of the invention. As is understandable to one of ordinary skill in the art, each of the embodiments as disclosed above may be used together in any combination. For example, SDA may be carried out in connection with an electronically addressable microchip wherein amplification primers specific for a target nucleic acid (such as branched or unbranched primer pairs having complementary sequence to ligation probes or other target nucleic acids of interest) are anchored to an electronically addressable capture pad, target nucleic acid is electronically addressed to such capture pads, and SDA is performed under high pressure. In another example, SDA may be carried out in connection with an electronically addressable microchip wherein allele-specific amplification primers (such as branched or unbranched primer pairs) are anchored to an electronically addressable capture pad, target nucleic acid is electronically addressed to such capture pads, and SDA is performed under high pressure or in the alternative at atmospheric pressure. In still another combination example, SDA may be carried out in connection with an electronically addressable microchip wherein the SDA reaction is carried out using noncleaveable primers or under asymmetric amplification conditions. Additionally, other combinations may include ligation-based SDA in combination with the electronically addressable microchip either under elevated or normal atmospheric pressures. As is understandable to one of ordinary skill in the art, many other combinations are possible.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein.

All publications and patent applications are herein incorporated by reference to the same extent as if each individual publication or patent application was specifically and individually indicated to be incorporated by reference.

What is claimed is:

1. A method for the amplification of one or more target nucleic acids of interest in one or more samples using a bioelectronic microchip comprising:

a) introducing at least one of the target nucleic acids onto a bioelectronic microchip having a plurality of electronically addressable capture sites;

b) electronically addressing the target nucleic acid to at least one capture site which has attached thereto at least a first NASBA oligonucleotide primer, wherein the first NASBA primer comprises a sequence specific for the target nucleic acid to be amplified;

c) hybridizing the target nucleic acid to be amplified to the first NASBA primer at the capture site;

d) contacting the hybridized target nucleic acid with enzymes and reagents necessary to support NASBA, including a Reverse Transcriptase activity, an RNA Polymerase activity, and an RNAse H activity, wherein the hybridized target nucleic acid is also contacted with a second NASBA oligonucleotide primer, wherein the second NASBA, primer comprises a sequence specific for the target nucleic acid sequence, and wherein at least one of the first and second NASBA primers comprises an RNA polymerase recognition sequence; and e) amplifying the target nucleic acid by NASBA to produce amplicon species.

2. The method of claim 1, further comprising an electronic washing step before step (d).

3. The method of claim 1, further comprising the passing of a sufficient negative charge through the electrode associated with the capture site to create electronically induced stringency to remove mis-matched hybridized target nucleic acids formed in step (c).

4. The method of claim 1 wherein at least a portion of the amplicons produced are anchored to the capture site.

5. The method of claim 1, further comprising a step (f) detecting at least one amplicon species.

6. The method of claim 5 wherein the detection in step (f) is by hybridization of a labeled oligonucleotide probe to the amplicon species.

7. The method of claim 6 wherein the probe is labeled with a labeling moiety selected from the group consisting of fluorescent moieties, chemiluminescent moieties, and electrochemiluminescent moieties.

8. The method of claim 7 wherein the labeling moiety is a fluorescent moiety selected from the group consisting of Bodipy-derivatives, Cyanine-derivatives, fluorescein-derivatives and rhodamine-derivatives.

9. The method of claim 6, further comprising the step of thermally denaturing any double stranded amplicon species after step (e).

10. The method of claim 6, further comprising the step of electronically denaturing any double stranded amplicon species after step (e).

11. The method of claim 5 wherein the detection in step (f) is by staining with ethidium bromide.

12. The method of claim 5 wherein the detection in step (f) is by the incorporation of a labeled nucleotide into the amplicon.

13. The method of claim 12 wherein the nucleotide is labeled with a labeling moiety selected from the group consisting of fluorescent moieties, chemiluminescent moieties, and electrochemiluminescent moieties.

14. The method of claim 13 wherein the labeling moiety is a fluorescent moiety selected from the group consisting of Bodipy-derivatives, Cyanine-derivatives, fluorescein-derivatives and rhodamine-derivatives.

15. The method of claim 5 wherein the detection in step (f) occurs simultaneously with the amplification of the target nucleic acid.

16. The method of claim 1 wherein the first NASBA primer is anchored to the capture site through a biotin/streptavidin interaction.

17. The method of claim 1 wherein the first NASBA primer is anchored to the capture site through a covalent linkage.

18. The method of claim 1 wherein the second NASBA primer is anchored to the capture site.

19. The method of claim 1 wherein the second NASBA primer is non-anchored.

20. The method of claim 1 wherein the target nucleic acid is further contacted with non-anchored first NASBA primers in step (d).

21. The method of claim 1 wherein more than one target nucleic acid is amplified simultaneously with the first target nucleic acid, and wherein more than one target nucleic acid is introduced onto the bioelectronic microchip in step (a), the method comprising the additional steps of:

b') electronically addressing each additional target nucleic acid to at least one capture site which has attached thereto at least a first NASBA oligonucleotide primer, wherein the first NASBA primer comprises a sequence specific for the additional target nucleic acid to be amplified;

c') hybridizing the additional target nucleic acid to be amplified to the first NASBA primer at the capture site;

d') contacting the hybridized target nucleic acid with enzymes and reagents necessary to support NASBA, including a Reverse Transcriptase activity, an RNA Polymerase activity, and an RNAse H activity, wherein the hybridized target nucleic acid is also contacted with a second NASBA oligonucleotide primer, wherein the second NASBA primer comprises a sequence specific for the additional target nucleic acid sequence, and wherein at least one of the first and second NASBA primers comprises an RNA polymerase recognition sequence; and e') amplifying the target nucleic acid by NASBA to produce amplicon species.

22. The method of claim 21, further comprising an electronic washing step before step (d').

23. The method of claim 21 wherein addressing steps (b) and (b'), hybridizing steps (c) and (c'), contacting steps (d) and (d'), and amplification steps (e) and (e') occur simultaneously.

24. The method of claim 21, further comprising the passing of a sufficient negative charge through the electrode associated with the capture site to create electronically induced stringency to remove mismatched hybridized target nucleic acids formed in the hybridization steps.

25. The method of claim 21 wherein at least a portion of the amplicons produced are anchored to the capture site.

26. The method of claim 21, further comprising a step (f) detecting at least one amplicon species.

27. The method of claim 26 wherein the detection in step (f) is by hybridization of a labeled oligonucleotide probe to the amplicon species.

28. The method of claim 27 wherein the probe is labeled with a labeling moiety selected from the group consisting of fluorescent moieties, chemiluminescent moieties, and electrochemiluminescent moieties.

29. The method of claim 28 wherein the labeling moiety is a fluorescent moiety selected from the group consisting of Bodipy-derivatives, Cyanine-derivatives, fluorescein-derivatives and rhodamine-derivatives.

30. The method of claim 27, further comprising the step of thermally denaturing any double stranded amplicon species after step (e).

31. The method of claim 27, further comprising the step of electronically denaturing any double stranded amplicon species after step (e).

32. The method of claim 26 wherein the detection in step (f) is by staining with ethidium bromide.

33. The method of claim 26 wherein the detection in step (f) is by the incorporation of a labeled nucleotide into the amplicon.

34. The method of claim 33 wherein the nucleotide is labeled with a labeling moiety selected from the group consisting of fluorescent moieties, chemiluminescent moieties, and electrochemiluminescent moieties.

35. The method of claim 34 wherein the labeling moiety is a fluorescent moiety selected from the group consisting of Bodipy-derivatives, Cyanine-derivatives, fluorescein-derivatives and rhodamine-derivatives.

36. The method of claim 26 wherein the detection in step (f) occurs simultaneously with the amplification of the target nucleic acid.

37. The method of claim 19 wherein the first NASBA primer is anchored to the capture site through a biotin/streptavidin interaction.

38. The method of claim 19 wherein the first NASBA primer is anchored to the capture site through a covalent linkage.

39. The method of claim 21 wherein the second NASBA primer is anchored to the capture site.

40. The method of claim 21 wherein the second NASBA primer is non-anchored.

41. The method of claim 21 wherein the target nucleic acid is further contacted with non-anchored first NASBA primers in step (d).

42. The method of claim of claim 1 wherein target nucleic acids from more than one sample are amplified, further comprising subjecting the target nucleic acids of each additional sample to steps a) through e).

43. The method of claim 42 wherein contacting step d) and amplification step e) are simultaneous for the target nucleic acids of more than one sample.

44. The method of claim 42, further comprising an electronic washing step before step (d).

45. The method of claim 42, further comprising the passing of a sufficient negative charge through the electrode associated with the capture site to create electronically induced stringency to remove mis-matched hybridized target nucleic acids formed in step (c).

46. The method of claim 42 wherein at least a portion of the amplicons produced are anchored to the capture site.

47. The method of claim 42, further comprising a step (f) detecting at least one amplicon species.

48. The method of claim 47 wherein the detection in step (f) is by hybridization of a labeled oligonucleotide probe to the amplicon species.

49. The method of claim 48 wherein the probe is labeled with a labeling moiety selected from the group consisting of fluorescent moieties, chemiluminescent moieties, and electrochemiluminescent moieties.

50. The method of claim 49 wherein the labeling moiety is a fluorescent moiety selected from the group consisting of Bodipy-derivatives, Cyanine-derivatives, fluorescein-derivatives and rhodamine-derivatives.

51. The method of claim 48, further comprising the step of thermally denaturing any double stranded amplicon species after step (e).

52. The method of claim 48, further comprising the step of electronically denaturing any double stranded amplicon species after step (e).

53. The method of claim 47 wherein the detection in step (f) is by staining with ethidium bromide.

54. The method of claim 47 wherein the detection in step (f) is by the incorporation of a labeled nucleotide into the amplicon.

55. The method of claim 54 wherein the nucleotide is labeled with a labeling moiety selected from the group consisting of fluorescent moieties, chemiluminescent moieties, and electrochemiluminescent moieties.

56. The method of claim 55 wherein the labeling moiety is a fluorescent moiety selected from the group consisting of Bodipy-derivatives, Cyanine-derivatives, fluorescein-derivatives and rhodamine-derivatives.

57. The method of claim 47 wherein the detection in step (f) occurs simultaneously with the amplification of the target nucleic acid.

58. The method of claim 42 wherein the first NASBA primer is anchored to the capture site through a biotin/streptavidin interaction.

59. The method of claim 42 wherein the first NASBA primer is anchored to the capture site through a covalent linkage.

60. The method of claim 42 wherein the second NASBA primer is anchored to the capture site.

61. The method of claim 42 wherein the second NASBA primer is non-anchored.

62. The method of claim 42 wherein the target nucleic acid is further contacted with non-anchored first NASBA primers in step (d).

63. The method of claim 1 wherein the RNAse H activity in step d) is provided by an RNAse H enzyme.

64. The method of claim 1 wherein the RNA polymerase activity in step d) is provided by T7 RNA polymerase, and wherein the RNA polymerase recognition sequence in step d) is recognized by T7 RNA polymerase.

* * * * *